United States Patent
Son et al.

(10) Patent No.: US 12,180,508 B2
(45) Date of Patent: Dec. 31, 2024

(54) METHOD OF PREPARING IN VITRO-MATURED HUMAN INTESTINAL ORGANOIDS AND USE THEREOF

(71) Applicant: KOREA RESEARCH INSTITUTE OF BIOSCIENCE AND BIOTECHNOLOGY, Daejeon (KR)

(72) Inventors: Mi Young Son, Daejeon (KR); Janghwan Kim, Daejeon (KR); Soo Jin Oh, Daejeon (KR); Cho Rok Jung, Daejeon (KR); Hyun Soo Cho, Daejeon (KR); Hana Lee, Daejeon (KR); Kwang Bo Jung, Daejeon (KR)

(73) Assignee: KOREA RESEARCH INSTITUTE OF BIOSCIENCE AND BIOTECHNOLOGY, Daejeon (KR)

( * ) Notice: Subject to any disclaimer, the term of this patent is extended or adjusted under 35 U.S.C. 154(b) by 430 days.

(21) Appl. No.: 16/598,425

(22) Filed: Oct. 10, 2019

(65) Prior Publication Data

US 2020/0115683 A1     Apr. 16, 2020

Related U.S. Application Data

(63) Continuation-in-part of application No. PCT/KR2018/004301, filed on Apr. 12, 2018.

(51) Int. Cl.
*C12N 5/071* (2010.01)
*A61K 35/38* (2015.01)
*G01N 33/50* (2006.01)

(52) U.S. Cl.
CPC ............ *C12N 5/0679* (2013.01); *A61K 35/38* (2013.01); *G01N 33/5082* (2013.01); *C12N 2501/2301* (2013.01); *C12N 2501/2302* (2013.01); *C12N 2501/2308* (2013.01); *C12N 2501/25* (2013.01); *C12N 2501/60* (2013.01); *C12N 2502/1114* (2013.01); *C12N 2506/02* (2013.01); *C12N 2506/45* (2013.01); *C12N 2513/00* (2013.01)

(58) Field of Classification Search
CPC .......... C12N 5/0679; C12N 2501/2301; C12N 2501/2302; C12N 2501/2308; C12N 2501/25; C12N 2501/60; C12N 2502/1114; C12N 2506/02; C12N 2506/45; C12N 2513/00; A61K 35/38; G01N 33/5082
USPC .................... 435/377, 77; 424/93.7
See application file for complete search history.

(56) References Cited

U.S. PATENT DOCUMENTS

2016/0067348 A1* 3/2016 Fiorina ................ A61K 31/402
                                                    424/178.1
2016/0287670 A1   10/2016 van den Brink et al.
2016/0312191 A1* 10/2016 Spence ................ C12N 5/0688

FOREIGN PATENT DOCUMENTS

WO      2017/048193 A1    3/2017

OTHER PUBLICATIONS

Zachos et al ("Human Enteroids/Colonoids and Intestinal Organoids Functionally Recapitulate Normal Intestinal Physiology and Pathophysiology," Journal of Biological Chemistry 291(8): 3759-3766 (2019)) (Year: 2019).*

(Continued)

*Primary Examiner* — Valarie E Bertoglio
(74) *Attorney, Agent, or Firm* — Morgan, Lewis & Bockius LLP

(57) ABSTRACT

Provided are a method of preparing in vitro-matured intestinal organoids, and intestinal organoids prepared by the method.

14 Claims, 67 Drawing Sheets

Specification includes a Sequence Listing.

(56) References Cited

OTHER PUBLICATIONS

Zeng et al (" mTOR signaling and transcrioptional regulation in T lymphocytes," Transcription 5:2 1254-1264 2014) (Year: 2014).*
Nozaki et al ("Co-culture with intestinal epithelial organoids allows efficient expansion and motility analysis of intraepithelial lymphocytes," J Gastroenterol (2016) 51:206-213) (Year: 2016).*
Fung et al ("IL-2 activation of a PI3K-dependent STAT3 serine phosphorylation pathway in primary human T cells," Cellular Signalling 15 (2003) 625-636). (Year: 2003).*
Lindemans et al., "Interleukin-22 promotes intestinal-stem-cell-mediated epithelial regeneration," Nature, 528(7583):560-564 (2015).
Kretzschmar et al., "Organoids: Modeling Development and the Stem Cell Niche in a Dish," Developmental Cell, 38:590-600 (2016).
Liu et al., "Drug discovery via Human-Derived Stem Cell Organoids," Frontiers in Pharmacology, 7: 334 (2016).
Finkbeiner et al., "Generation of tissue-engineered small intestine using embryonic stem cell-derived human intestinal organoids," Biology Open, 4: 1462-1472 (2015).
Hibiya et al., "Long-term Inflammation Transforms Intestinal Epithelial Cells of Colonic Organoids," Journal of Crohn's and Colitis, 621-530 (2016).
Forster et al., "Human Intestinal Tissue with Adult Stem Cell Properties Derived from Pluripotent Stem Cells," Stem Cell Reports, 2 (6):838-852 (2014).
Dedhia et al., "Organoid Models of Human Gastrointestinal Development and Disease," Gastroenterology, 150 (5):1098-1112 (2016).
Spence et al., "Directed differentiation of human pluripotent stem cells into intestinal tissue in vitro," Nature, 470 (7332): 105-109 (2011).
Yoon et al., "Novel TRAIL Sensitizer Taraxacum Officinale F.H. Wigg Enhances TRAIL-Inducted Apoptosis in Huh7 Cells," Molecular Carcinogenesis, 55: 387-396 (2015).
Son et al., "Proteomic and network analysis of proteins regulated by REX1 in human embryonic stem cells," Proteomics 15: 2220-2229 (2015).
Cho et al., "Direct regulation of E-cadherin by targeted histone methylation of TALE-SET fusion protein in cancer cells," Oncotarget, 6 (27): 23837-23844 (2015).
Kwak et al., "Biochemical and molecular characterization of novel mutations in GLB1 and NEU1 in patient cells with ysosomal storage disorders," Biochemical and Biophysical Research Communications, 457: 554-560 (2015).
Son et al., "Comparative receptor tyrosine kinase profiling identifies a novel role for AXL in human stem cell pluripotency," Human Molecular Genetics, 23 (7): 1802-1816 (2014).
Watson et al., "An in vivo model of human small intestine using pluripotent stem cells," Nature Medicine, 20 (11): 1310-1314 (2014).
International Search Report issued in corresponding International Patent Application No. PCT/KR2018/004301 dated Jul. 30, 2018.

* cited by examiner

[FIG. 1a]
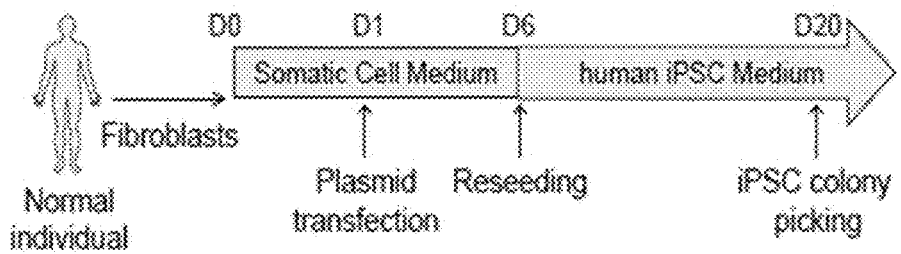
[FIG. 1b]
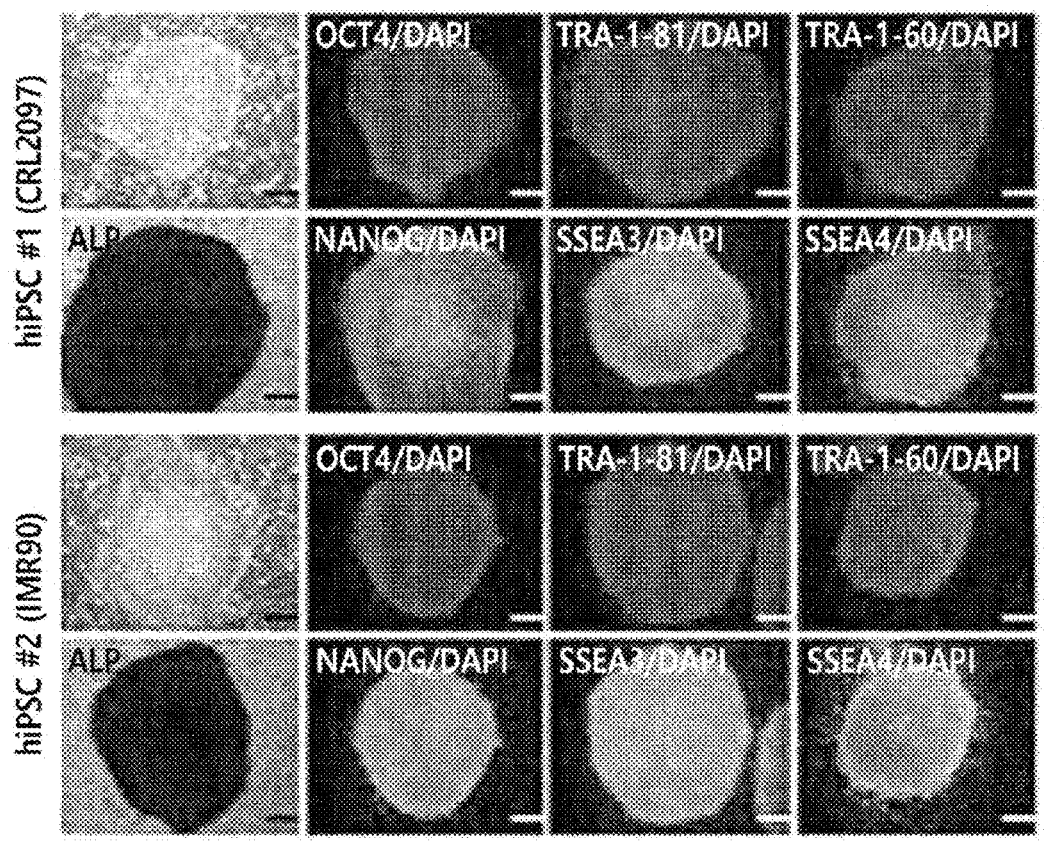

[FIG. 1c]
| Locus/Clone | CRL2097 | | | | IMR90 | | | |
|---|---|---|---|---|---|---|---|---|
| | Fibroblast | | hiPSC #1 | | Fibroblast | | hiPSC #2 | |
| D8S1179 | 12 | 12 | 12 | 12 | 13 | 14 | 13 | 14 |
| D21S11 | 29 | 31.2 | 29 | 31.2 | 30.2 | 31 | 30.2 | 31 |
| D7S820 | 12 | 12 | 12 | 12 | 9 | 12 | 9 | 12 |
| CSF1PO | 12 | 13 | 12 | 13 | 11 | 13 | 11 | 13 |
| D3S1358 | 15 | 15 | 15 | 15 | 14 | 15 | 14 | 15 |
| TH01 | 6 | 9.3 | 6 | 9.3 | 8 | 9.3 | 8 | 9.3 |
| D13S317 | 11 | 12 | 11 | 12 | 11 | 13 | 11 | 13 |
| D16S539 | 9 | 11 | 9 | 11 | 10 | 13 | 10 | 13 |
| D2S1338 | 20 | 23 | 20 | 23 | 19 | 25 | 19 | 25 |
| D19S433 | 13 | 15 | 13 | 15 | 10 | 13 | 10 | 13 |
| vWA | 17 | 18 | 17 | 18 | 16 | 19 | 16 | 19 |
| TPOX | 10 | 11 | 10 | 11 | 8 | 9 | 8 | 9 |
| D18S51 | 13 | 18 | 13 | 18 | 17 | 17 | 17 | 17 |
| D5S818 | 11 | 12 | 11 | 12 | 22 | 13 | 22 | 13 |
| FGA | 24 | 26 | 24 | 26 | 25 | 28 | 25 | 28 |
| Gender | XY | | XY | | XX | | XX | |
[FIG. 1d]
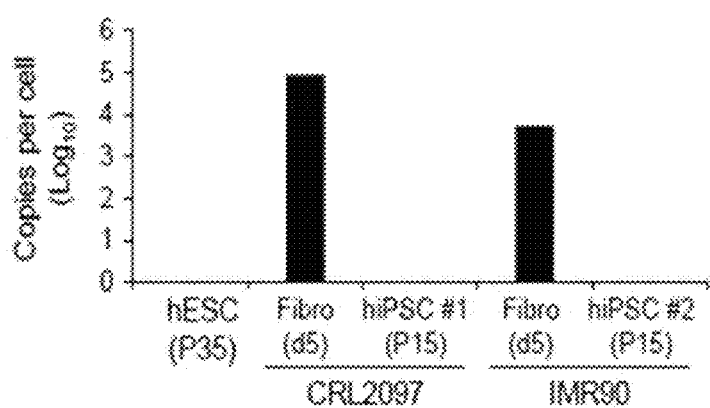

[FIG. 1e]
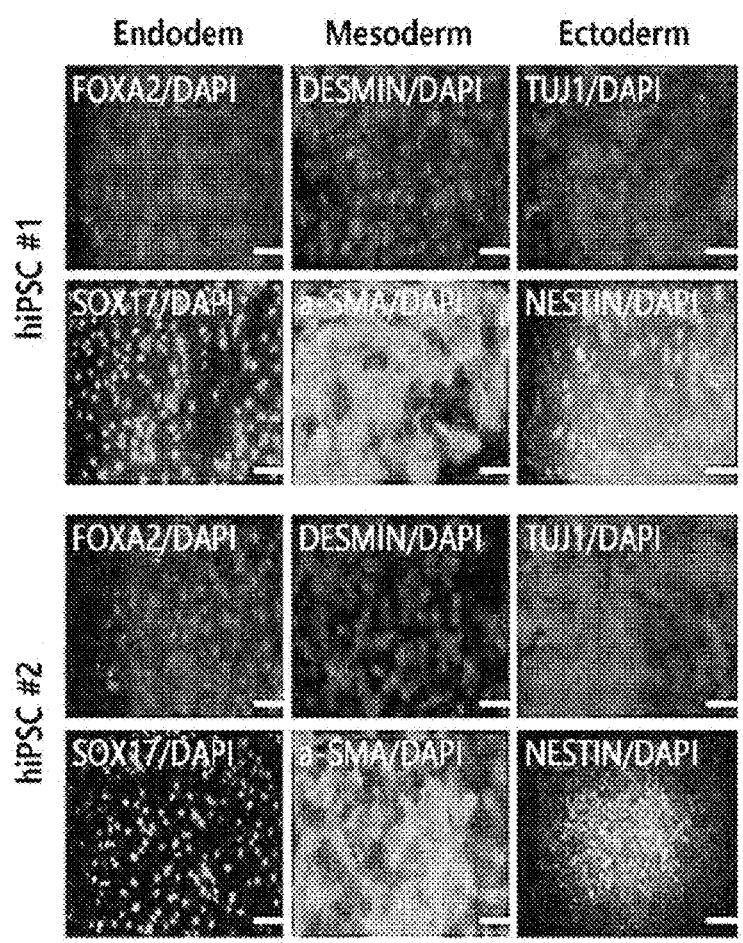

[FIG. 1f]
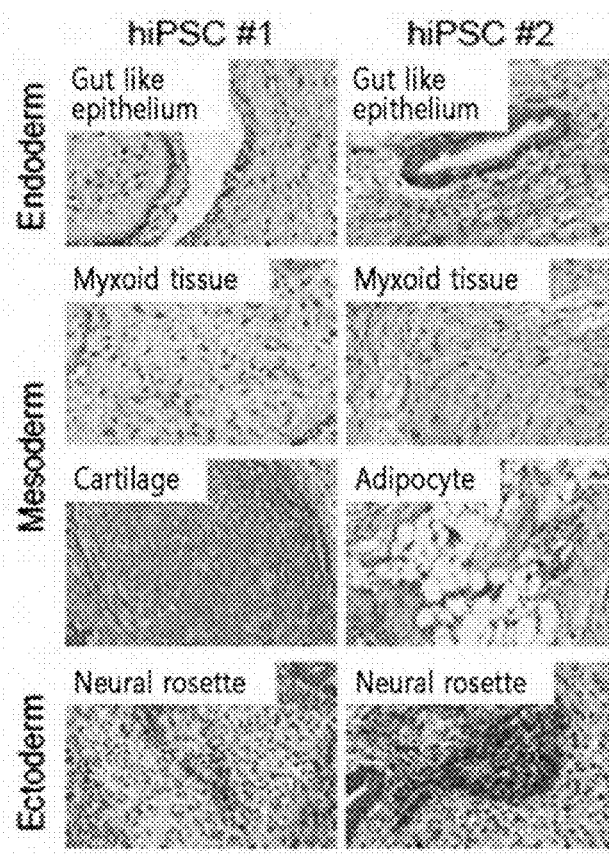

[FIG. 1g]
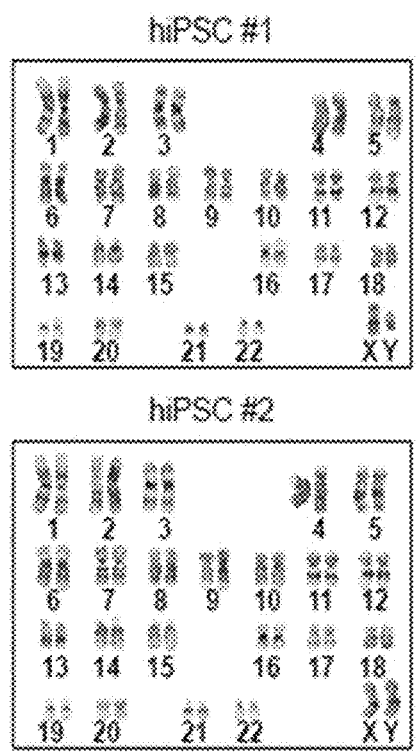
[FIG. 2a]
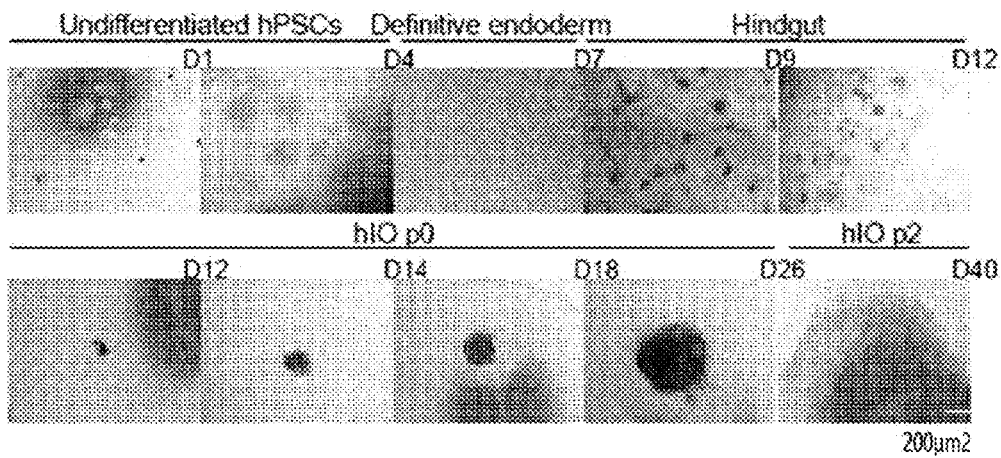

[FIG. 2b]
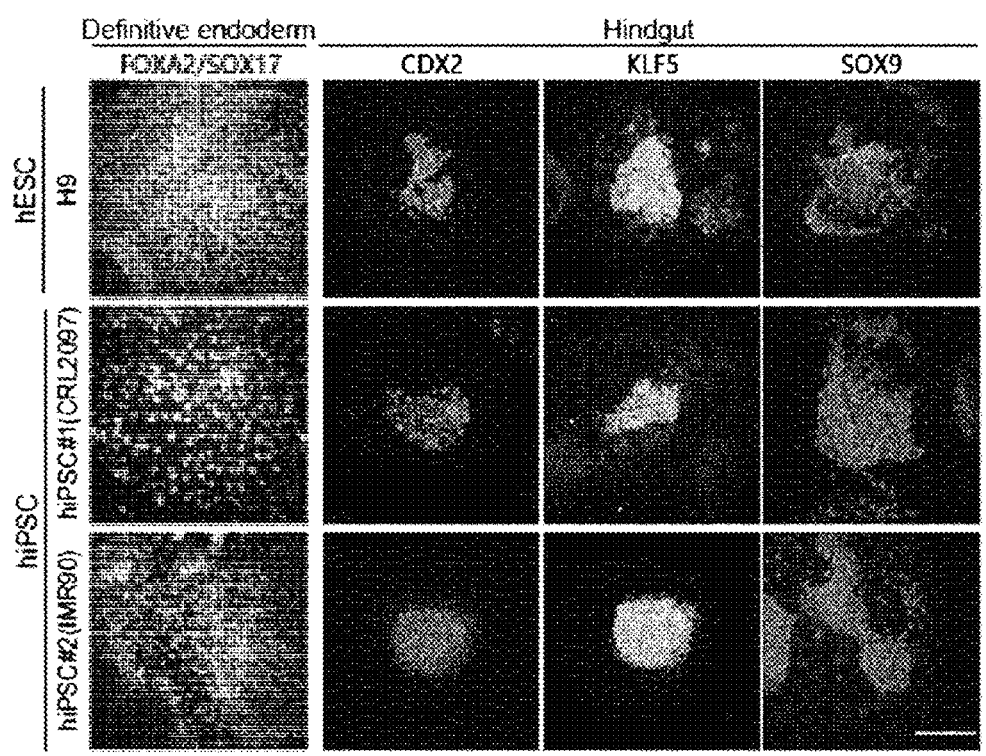

[FIG. 2c]
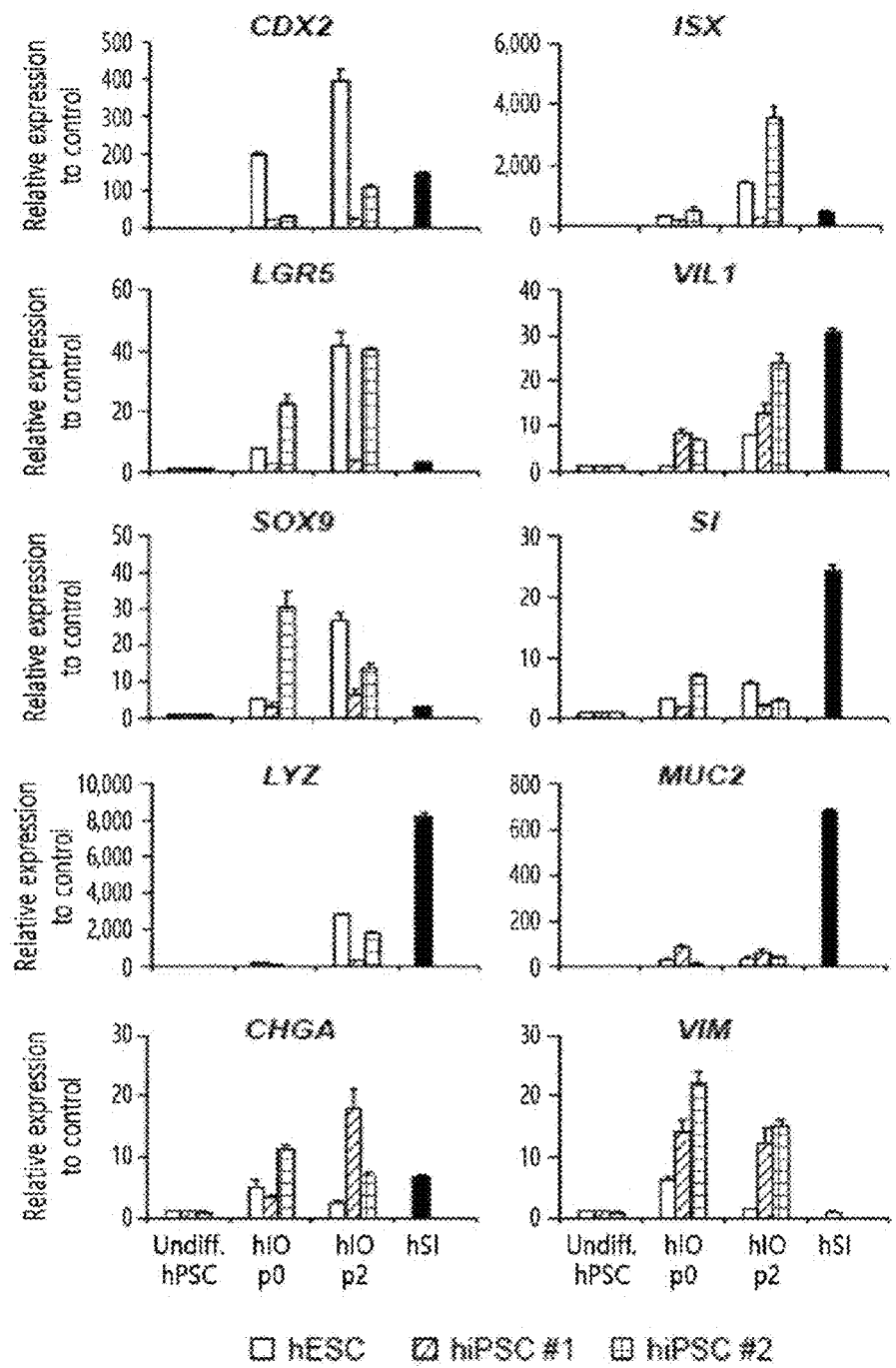

[FIG. 3a]
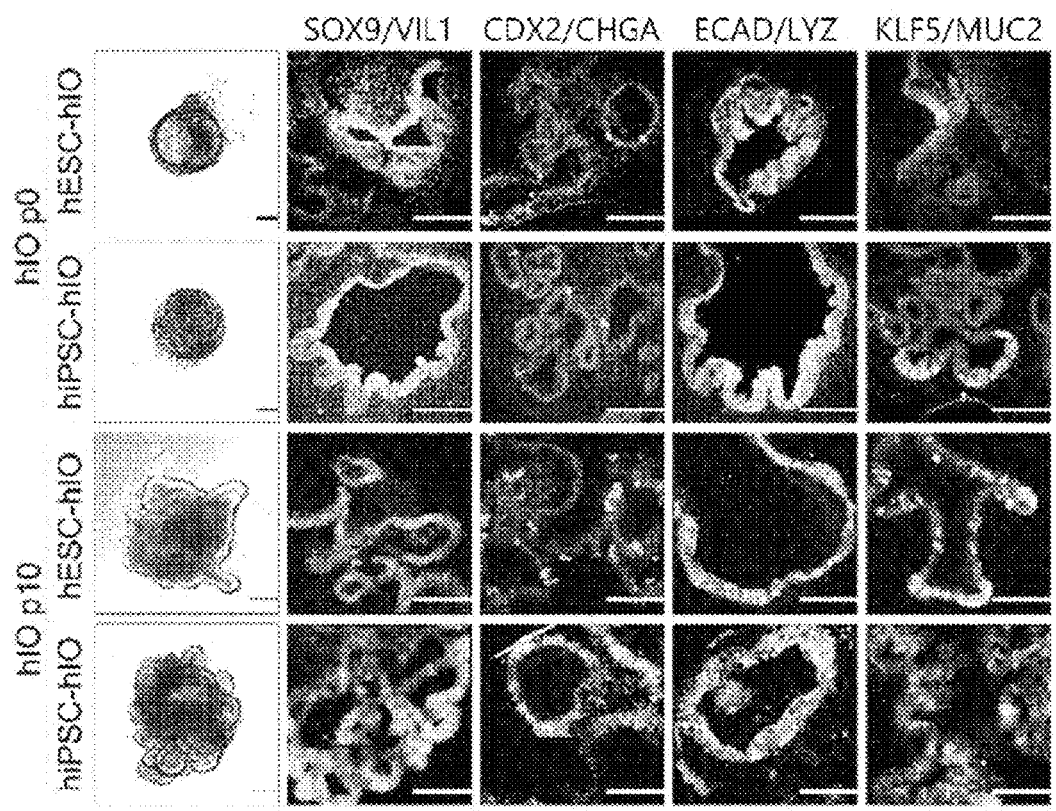
[FIG. 3b]
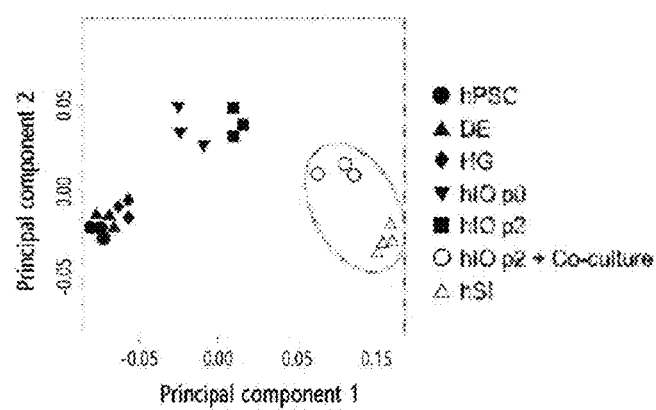

[FIG. 3c]
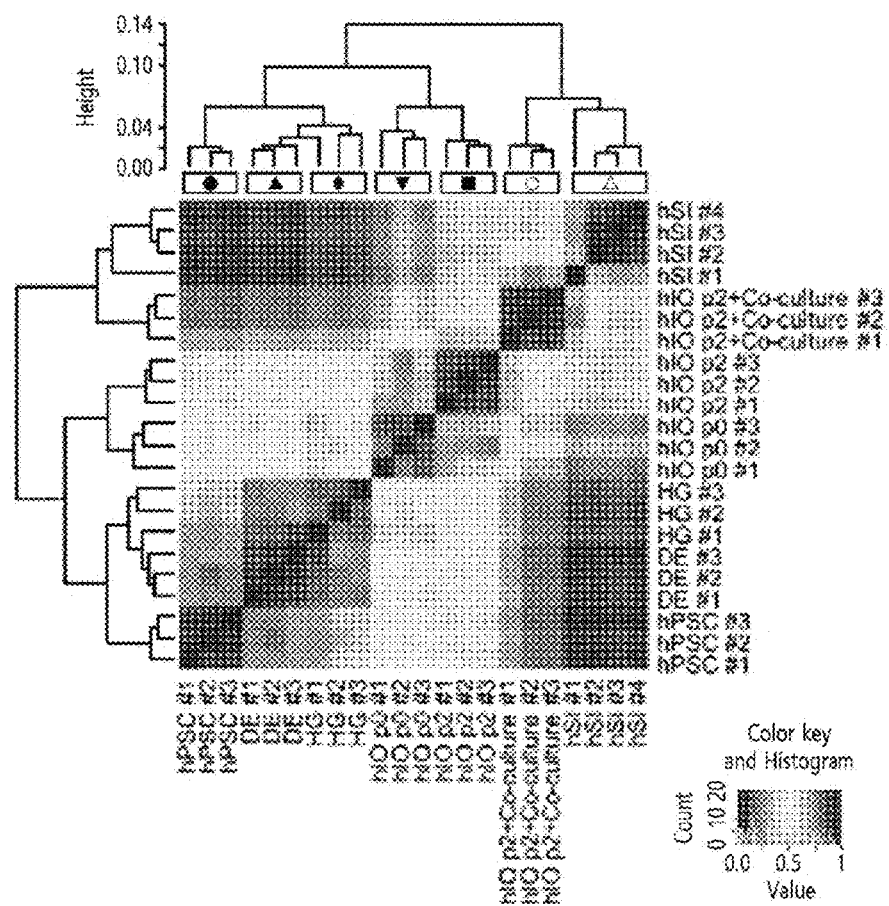

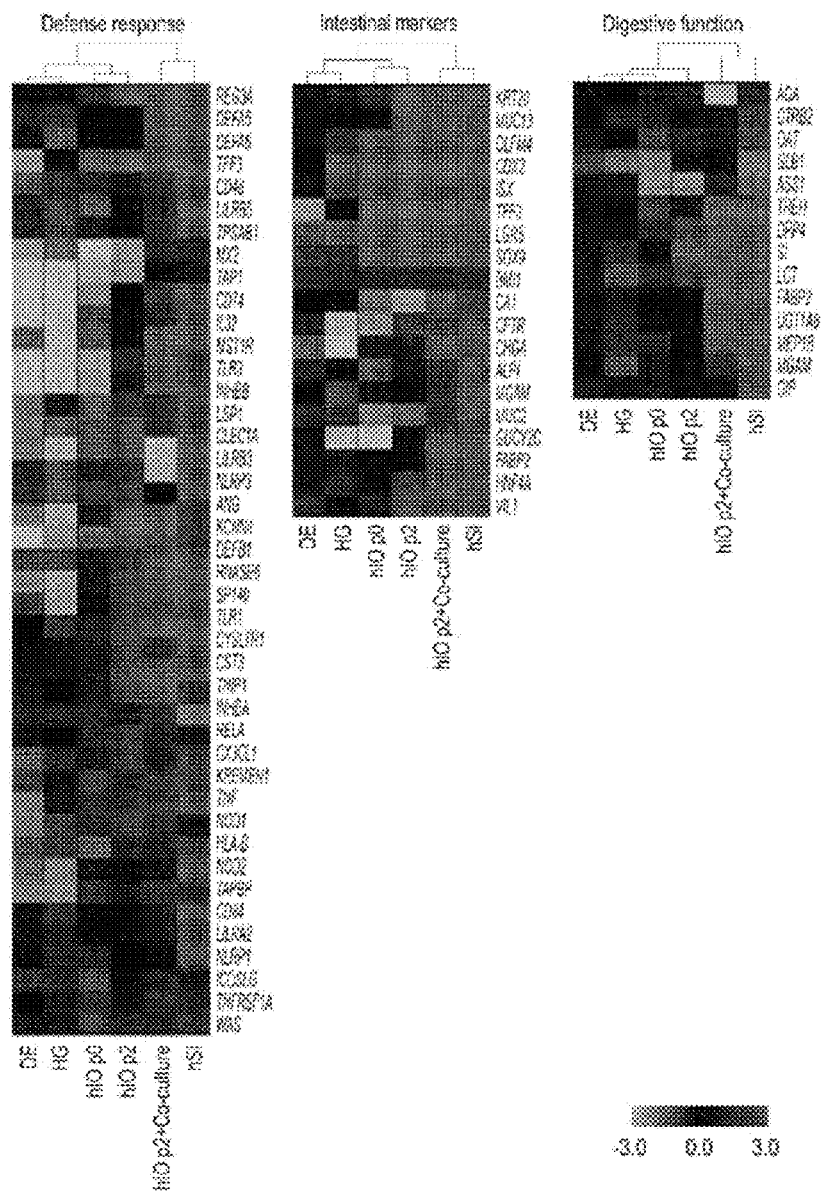
[FIG. 3d]

[FIG. 3e]
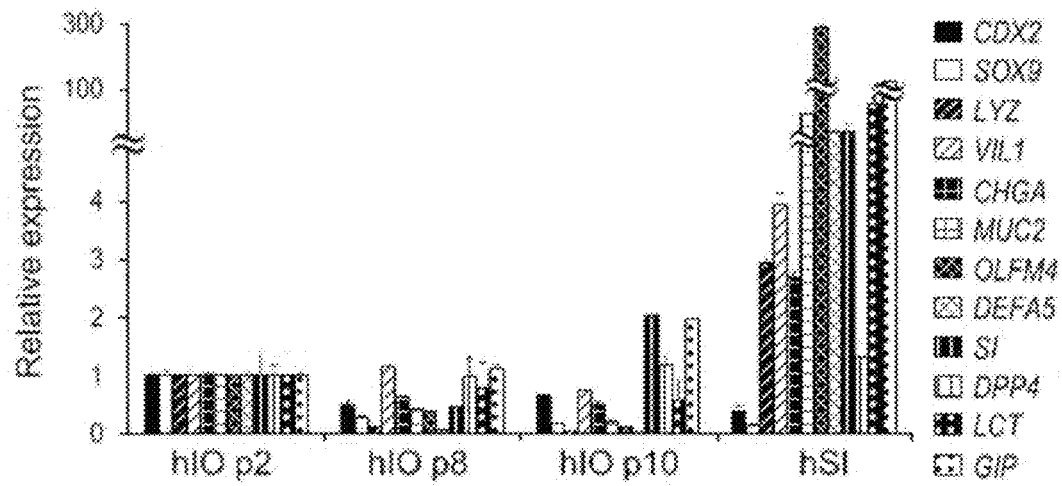
[FIG. 3f]
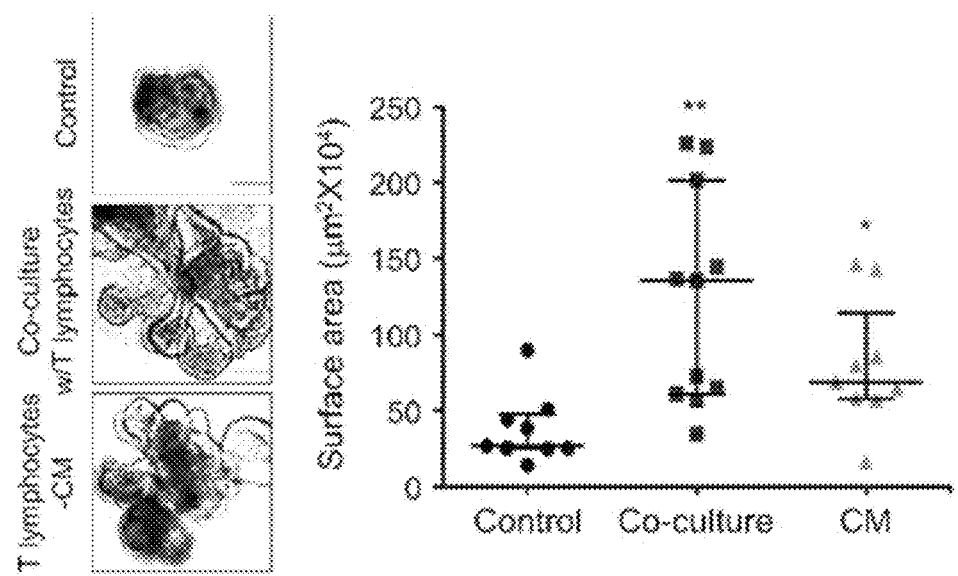

[FIG. 4a]
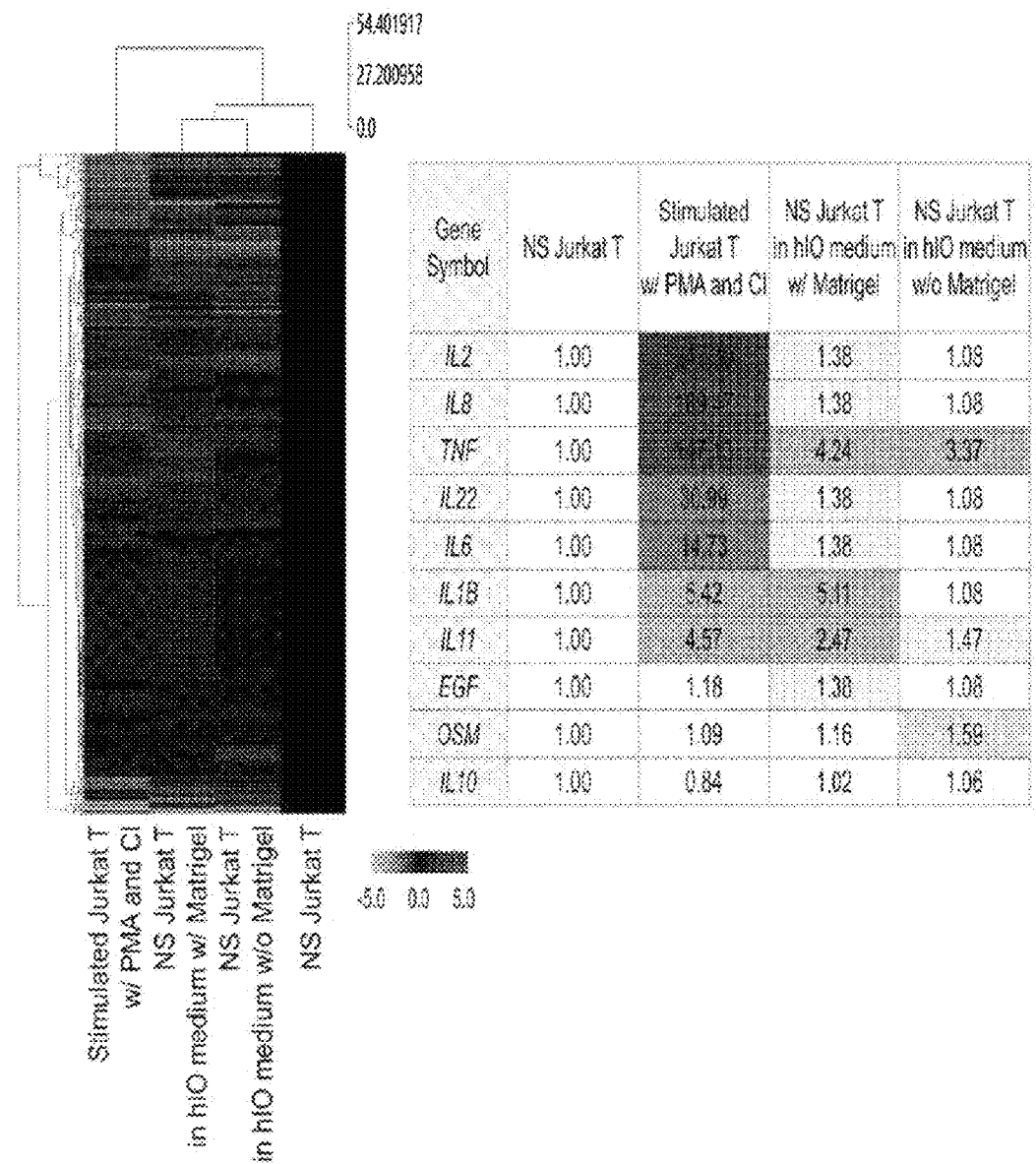

[FIG. 4b]

| Cytokines | Cytokine expression levels (pg/ml) | | | | | |
|---|---|---|---|---|---|---|
| | Jurkat T medium | NS Jurkat T | Stimulated Jurkat T w/ PMA and CI | hIO medium | NS Jurkat T in hIO medium w/ Matrigel | NS Jurkat T in hIO medium w/o Matrigel |
| IL-2 | ND | 2.00 ± 0.01 | 1003.59 ± 14.08 | ND | 1.00 ± 0.34 | 1.00 ± 0.51 |
| IL-8 | ND | 5.86 ± 2.46 | 160.38 ± 23.41 | ND | 4.29 ± 1.43 | 2.86 ± 0.70 |
| TNFα | 1.88 ± 0.78 | 8.75 ± 2.50 | 36.88 ± 6.87 | 1.88 ± 0.07 | 5.00 ± 0.58 | 3.13 ± 0.63 |
| IL-22 | 2.38 ± 0.83 | 3.33 ± 2.381 | 4.29 ± 2.38 | 2.38 ± 0.85 | 2.86 ± 0.95 | 3.33 ± 1.44 |
| IL-6 | ND | ND | ND | ND | ND | ND |
| IL-1β | 2.80 ± 2.00 | 2.20 ± 0.60 | 3.80 ± 0.60 | 5.00 ± 2.60 | 4.80 ± 0.80 | 4.40 ± 1.62 |
| IL-11 | 7.22 ± 1.67 | 1.67 ± 0.67 | 8.33 ± 0.56 | 8.89 ± 4.41 | 6.11 ± 1.67 | 3.33 ± 0.47 |
| EGF* | ND | ND | ND | 93941.40 ± 411.76 | 64882.5 ± 1823.53 | 57706.10 ± 1705.88 |
| OSM | 7.36 ± 0.47 | 6.27 ± 0.31 | 13.53 ± 1.17 | 8.38 ± 0.08 | 9.31 ± 0.23 | 7.59 ± 0.54 |
| IL-10 | ND | ND | ND | ND | ND | ND |

All data are represented as mean ± SEM.
NS, non-stimulated
ND, not detectable release.
* Cytokine included in hIO medium at concentrations of 100 ng/ml.

[FIG. 5a]
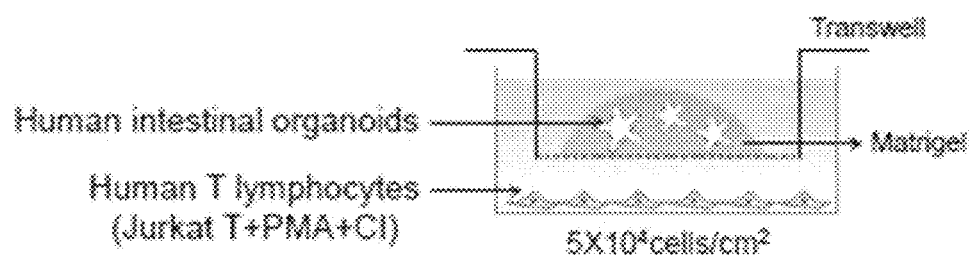
[FIG. 5b]
Co-culture
Control     NS Jurkat T     Stimulated Jurkat T
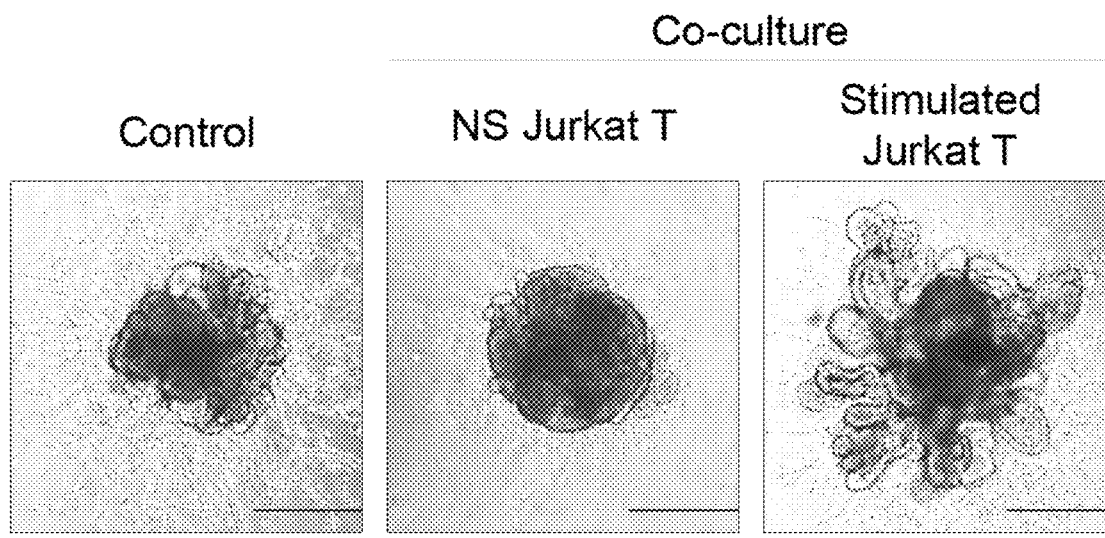

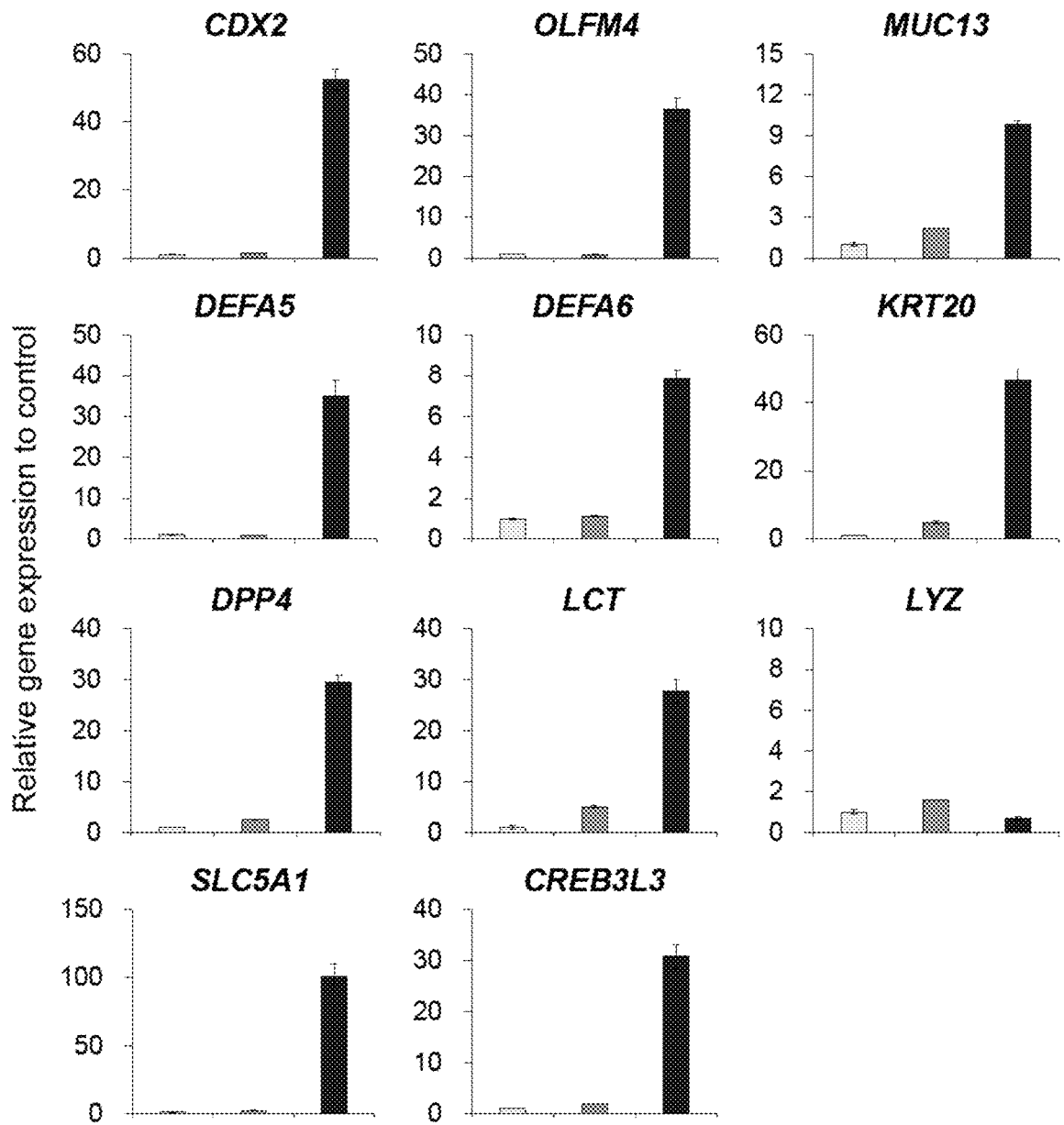
[FIG. 5c]

[FIG. 6a]
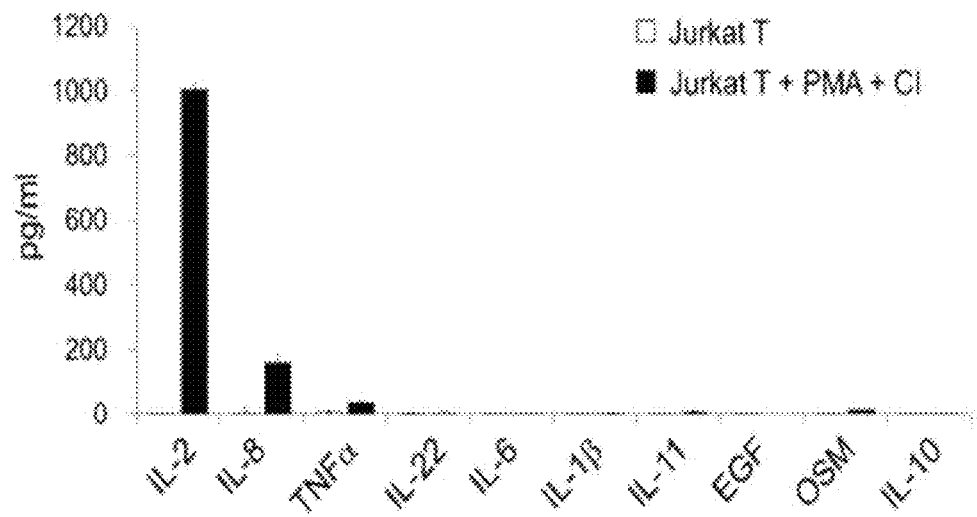
[FIG. 6b]
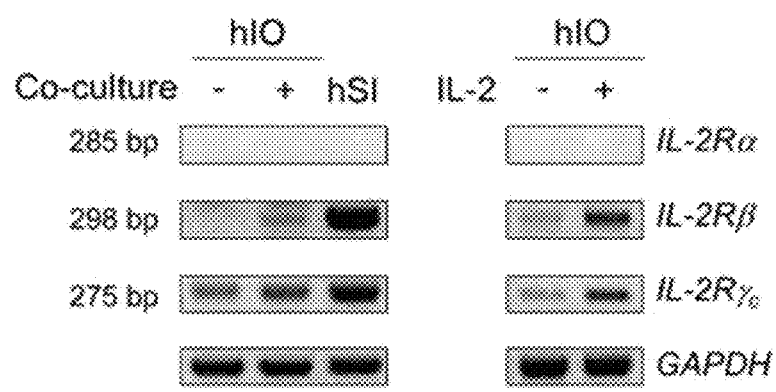

[FIG. 6c]
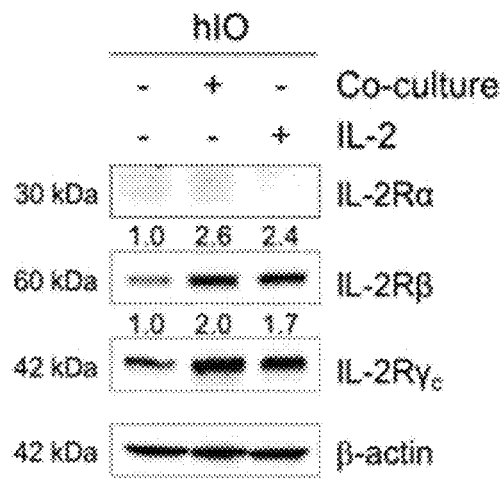
[FIG. 6d]
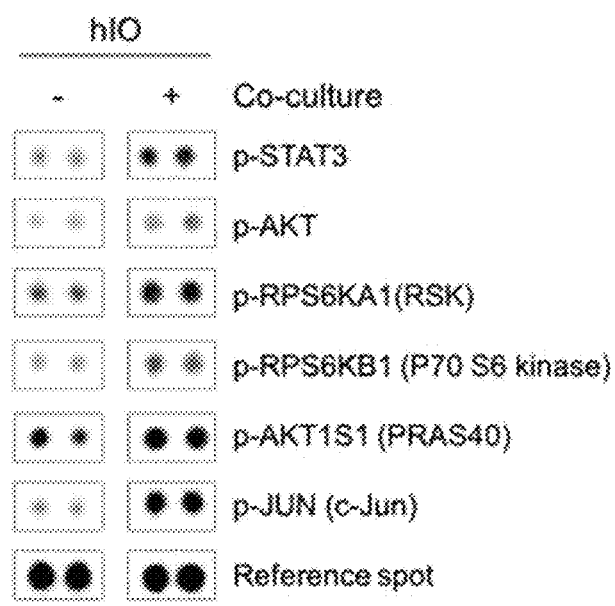

[FIG. 6e]
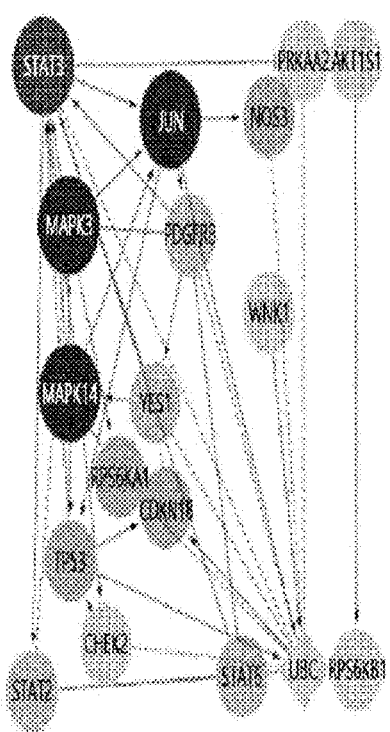

[FIG. 7a]
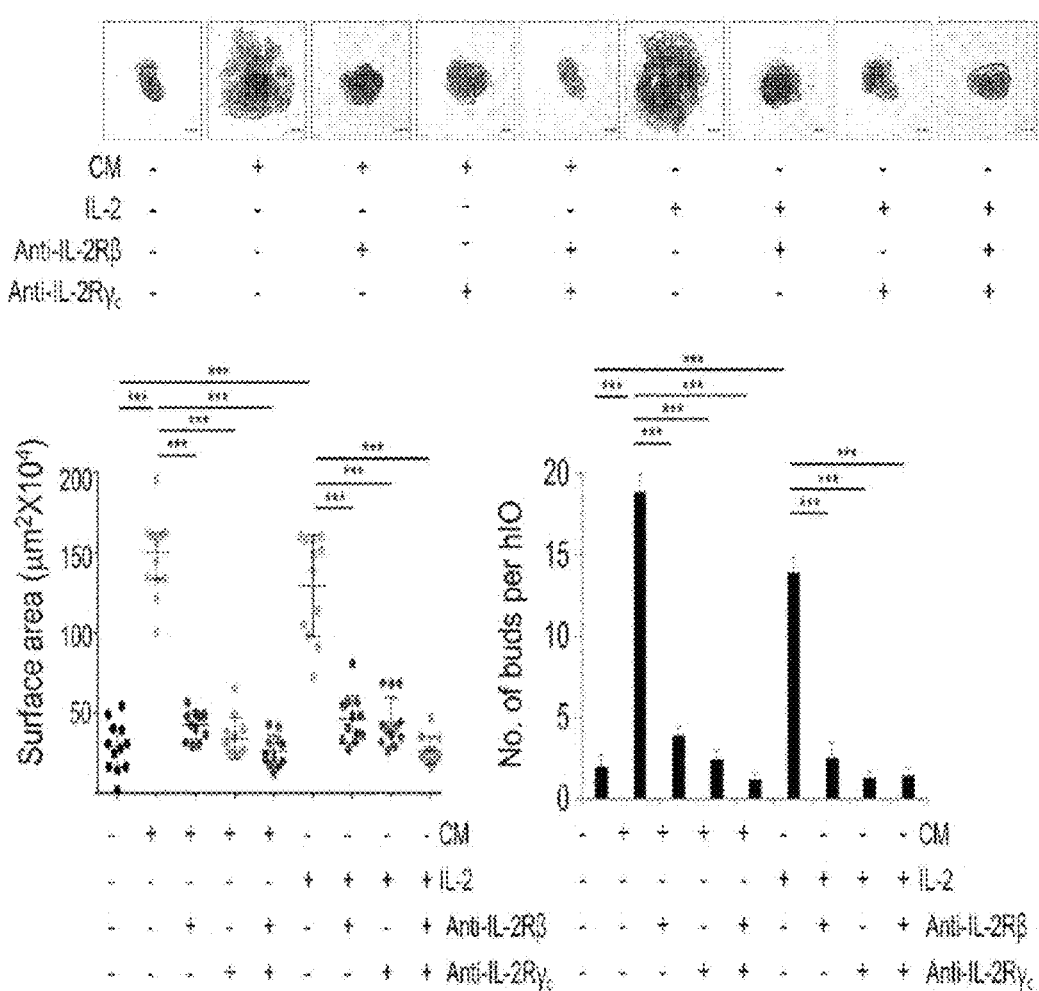

[FIG. 7b]
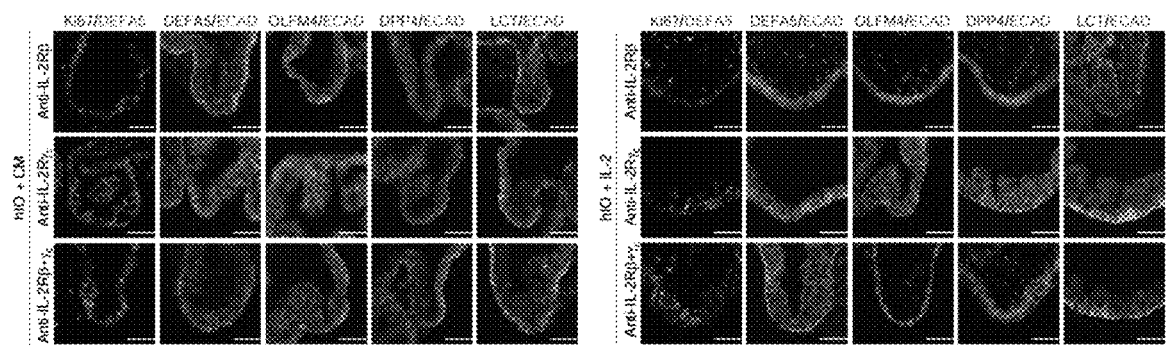
[FIG. 7c]
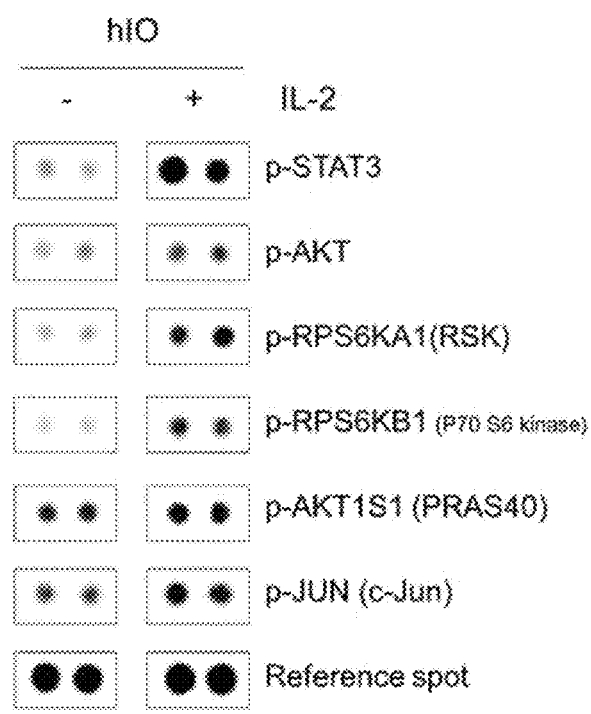

[FIG. 7d]
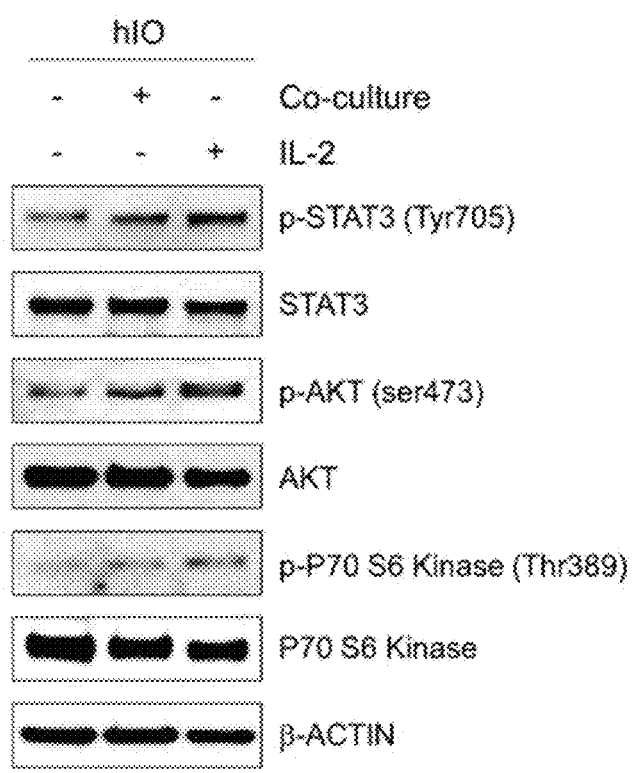

[FIG. 7e]

| Pathway in network | | |
|---|---|---|
| GeneSet | FDR | Nodes |
| mTOR signaling pathway(K) | 3.33E-04 | AKT1S1,RPS6KA1, RPS6KB1 |
| Ras Pathway(P) | 4.00E-04 | RPS6KA1,JUN, STAT3 |
| Signaling by SCF-KIT(R) | 5.00E-04 | AKT1S1,CDKN1B, YES1,STAT3 |
| Epstein-Barr virus infection(K) | 5.00E-04 | CDKN1B,JUN, HSPB1,STAT3 |
| Regulation of Telomerase(N) | 5.71E-04 | CDKN1B,JUN, RPS6KB1 |
| CDC42 signaling events(N) | 6.25E-04 | JUN,RPS6KB1, YES1 |
| Senescence-Associated Secretory Phenotype | 1.00E-03 | CDKN1B,RPS6KA1, JUN,STAT3 |
| ErbB signaling pathway(K) | 1.11E-03 | CDKN1B,JUN, RPS6KB1 |
| Signaling by NGF(R) | 1.40E-03 | AKT1S1,CDKN1B, RPS6KA1,STAT3 |
| HIF-1 signaling pathway(K) | 1.64E-03 | CDKN1B,RPS6KB1, STAT3 |

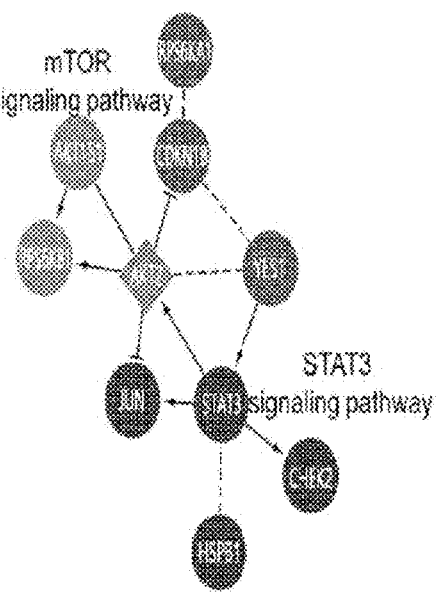

[FIG. 7f]
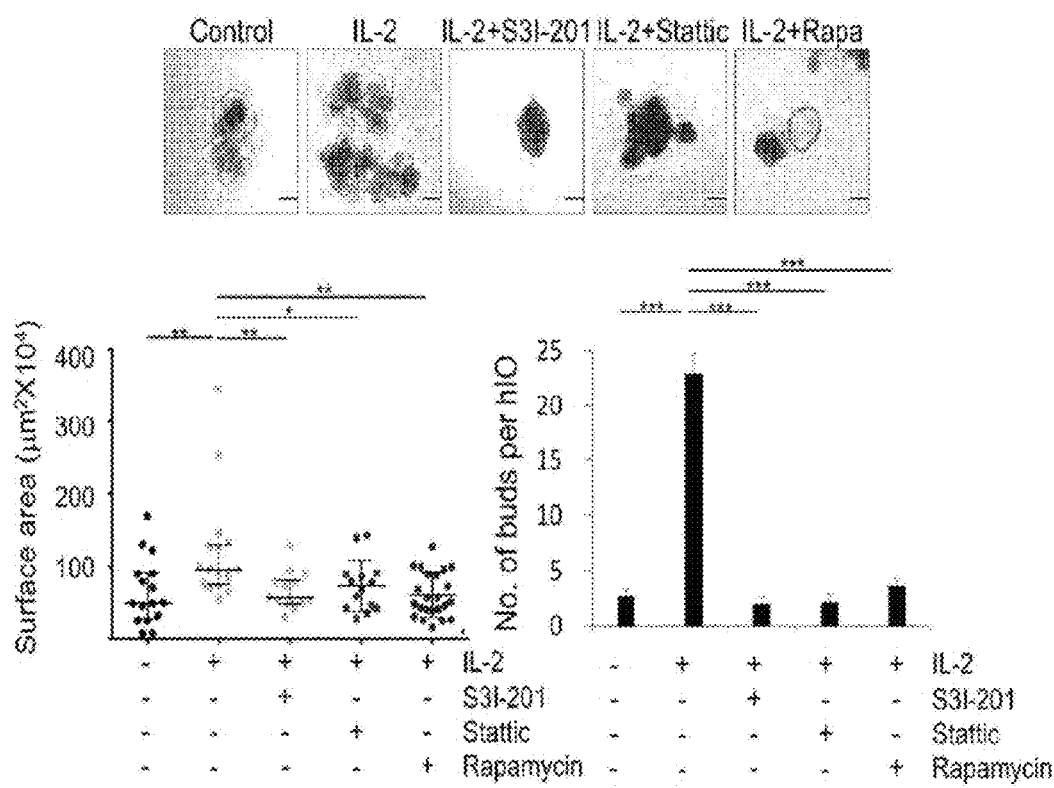

[FIG. 7g]
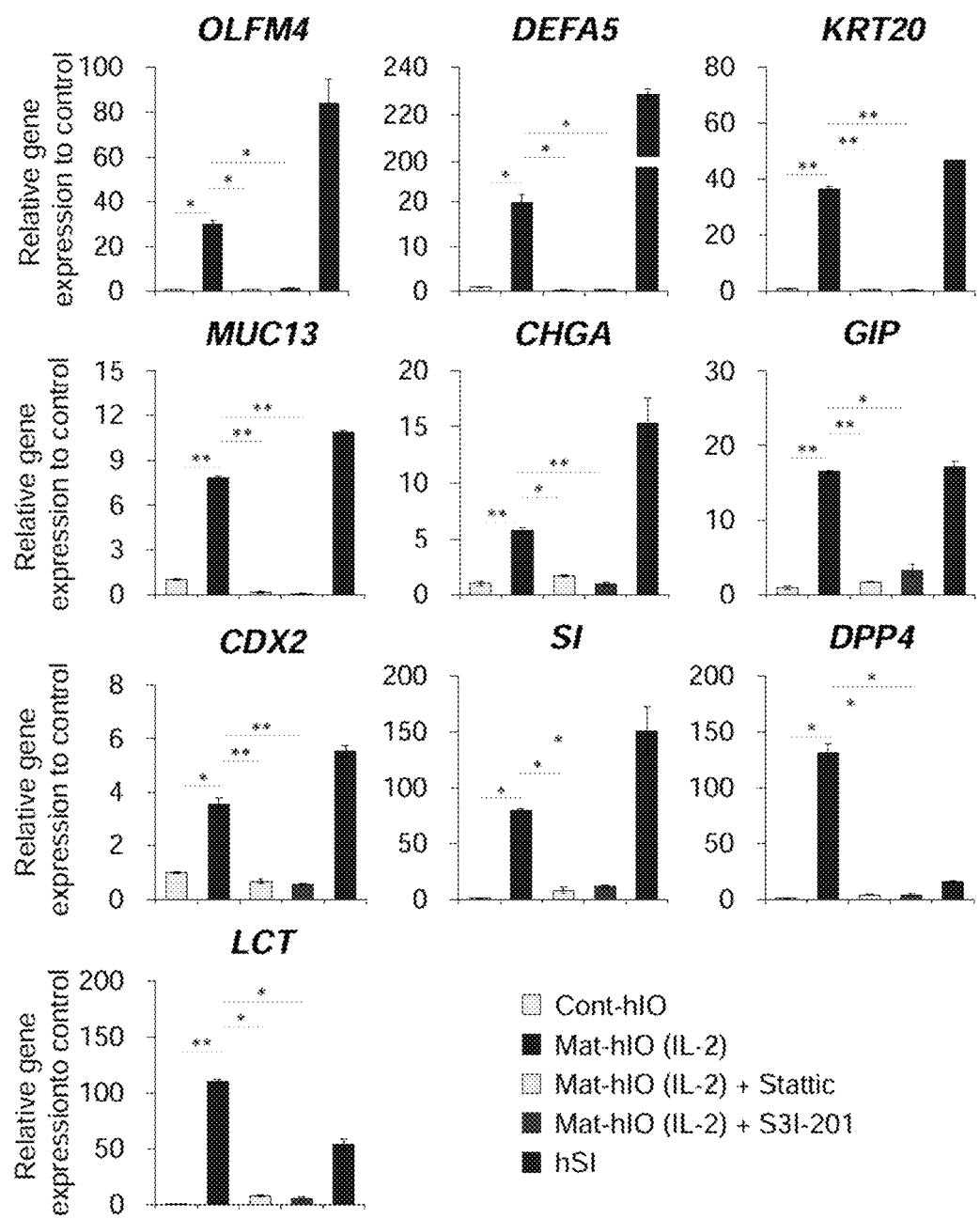

[FIG. 8a]
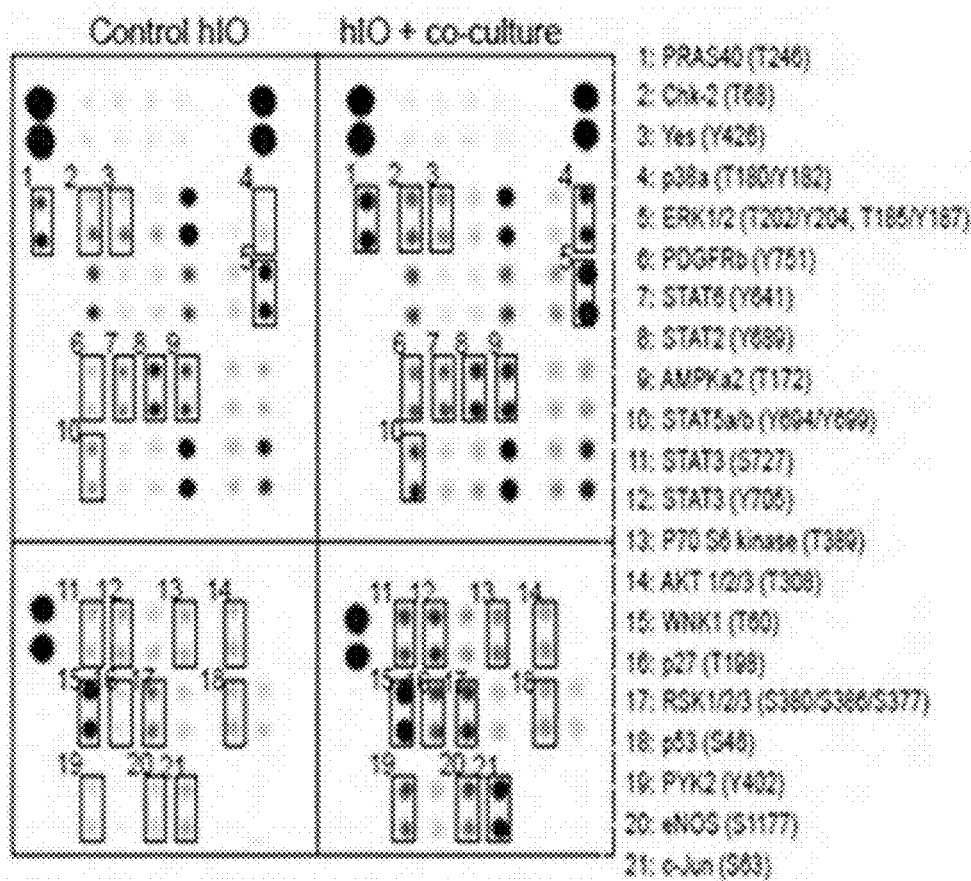

[FIG. 8b]
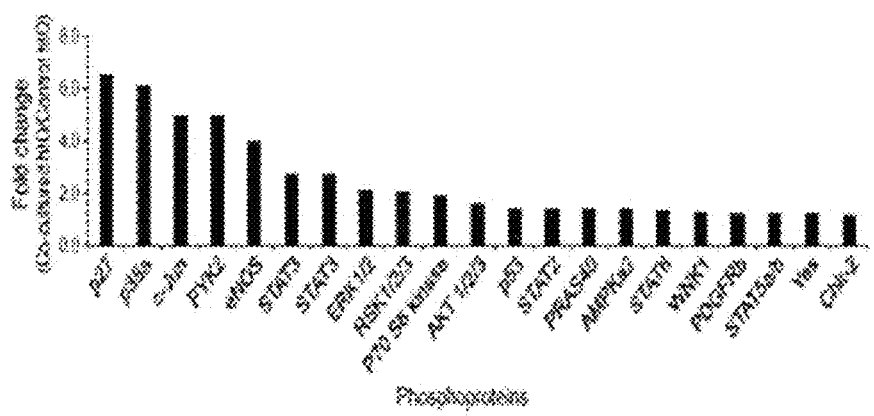

[FIG. 8c]
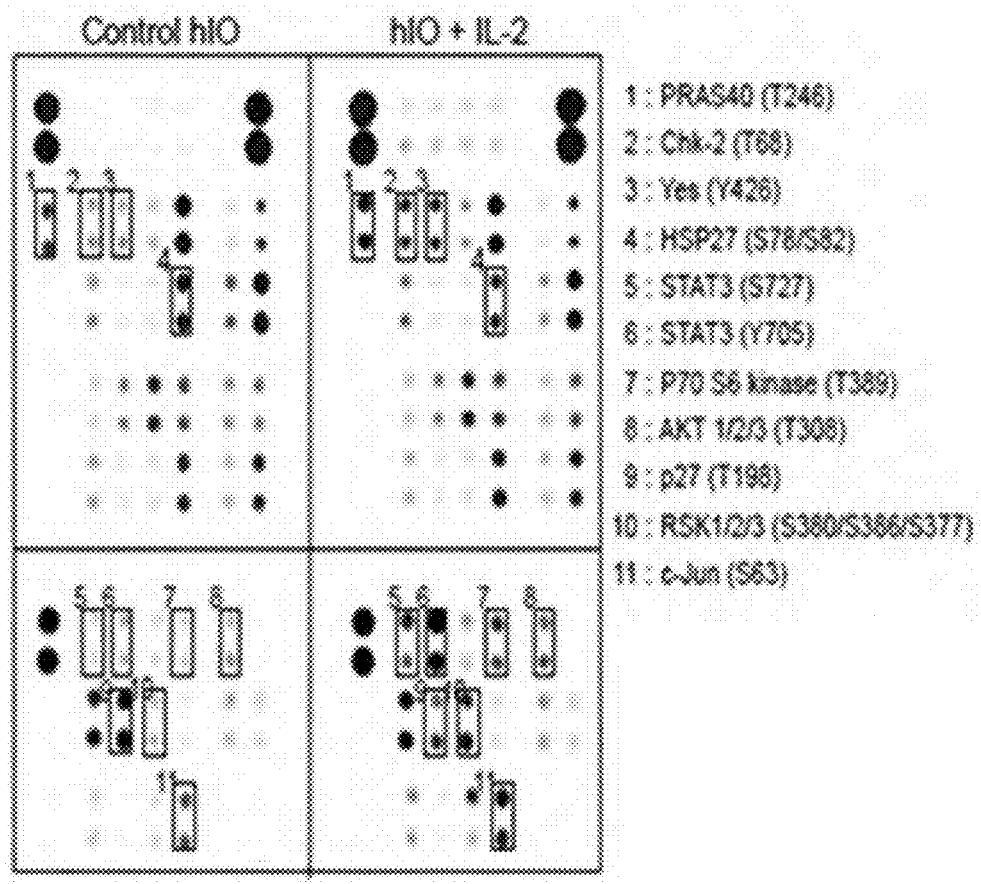

[FIG. 8d]
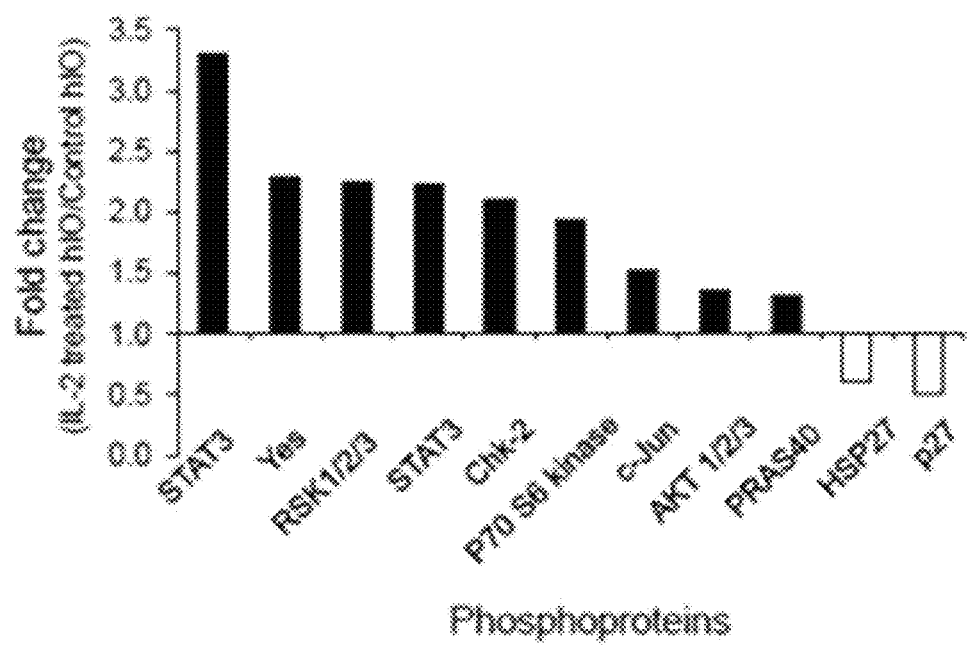

[FIG. 9]
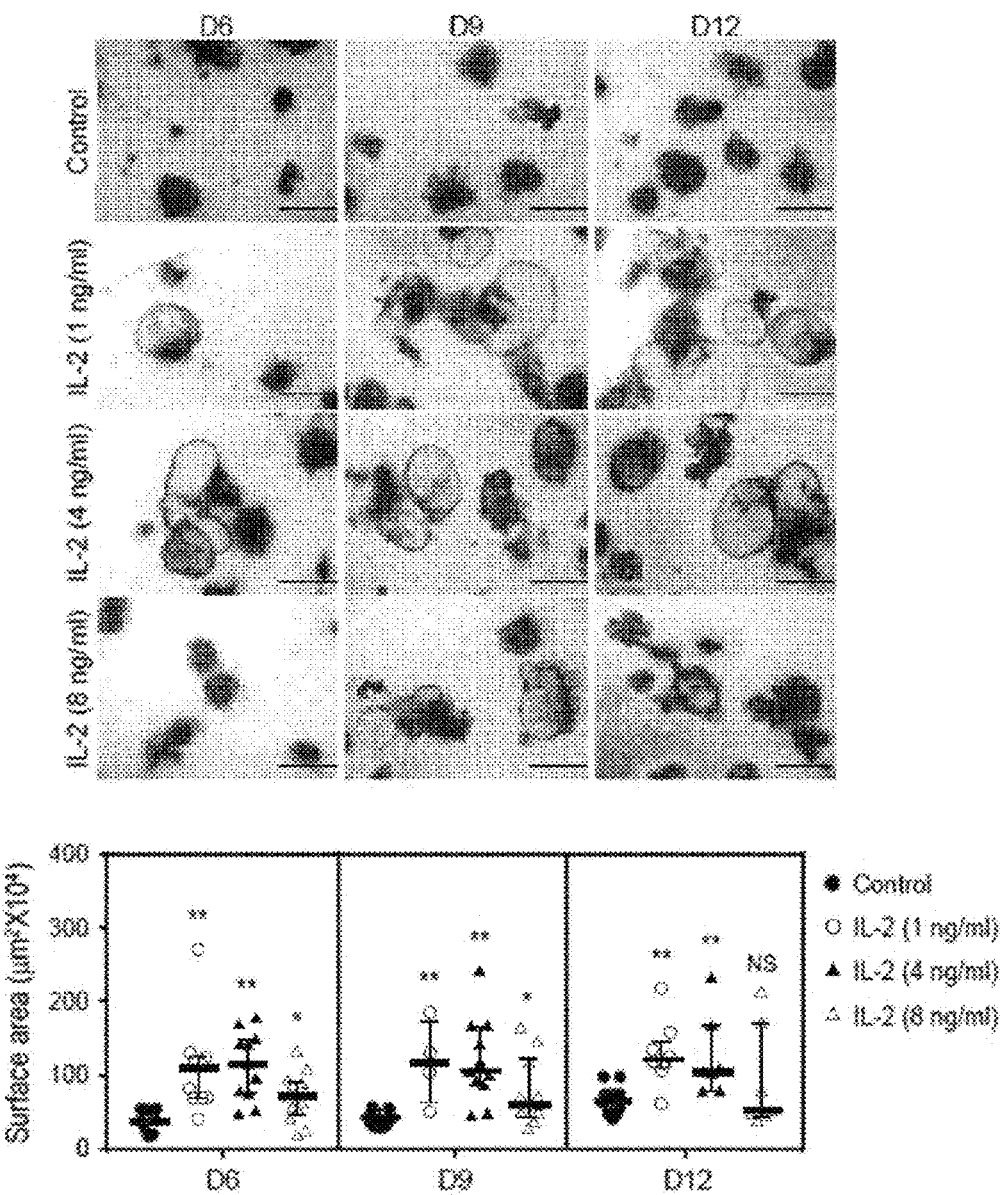

[FIG. 10a]
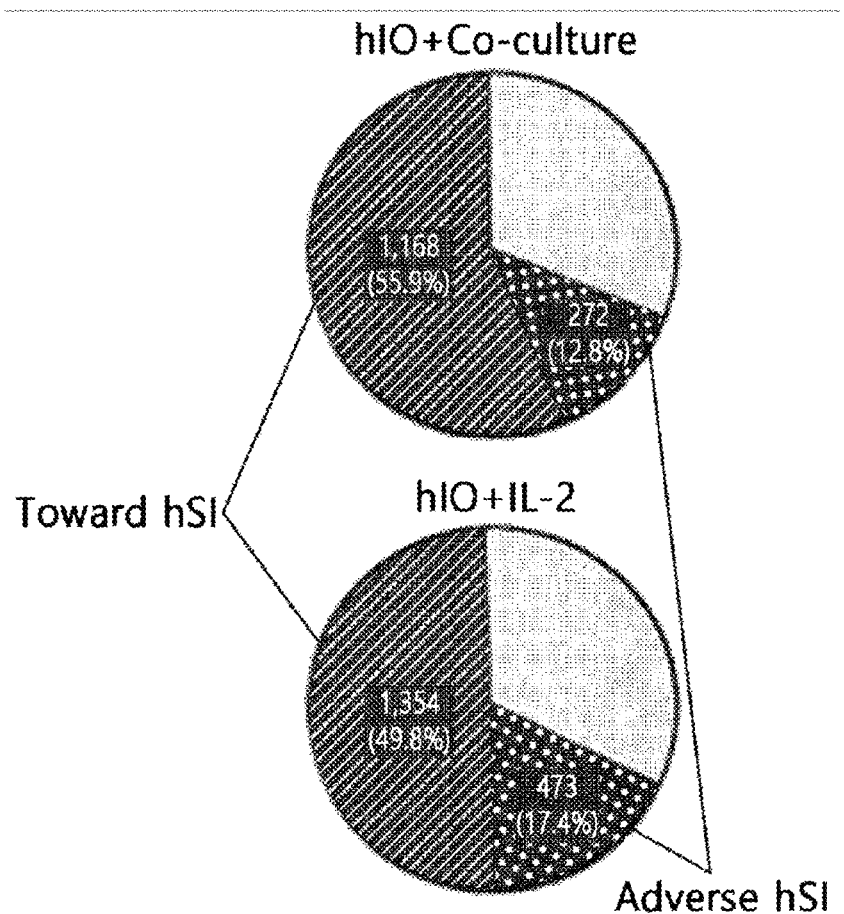

[FIG. 10b]
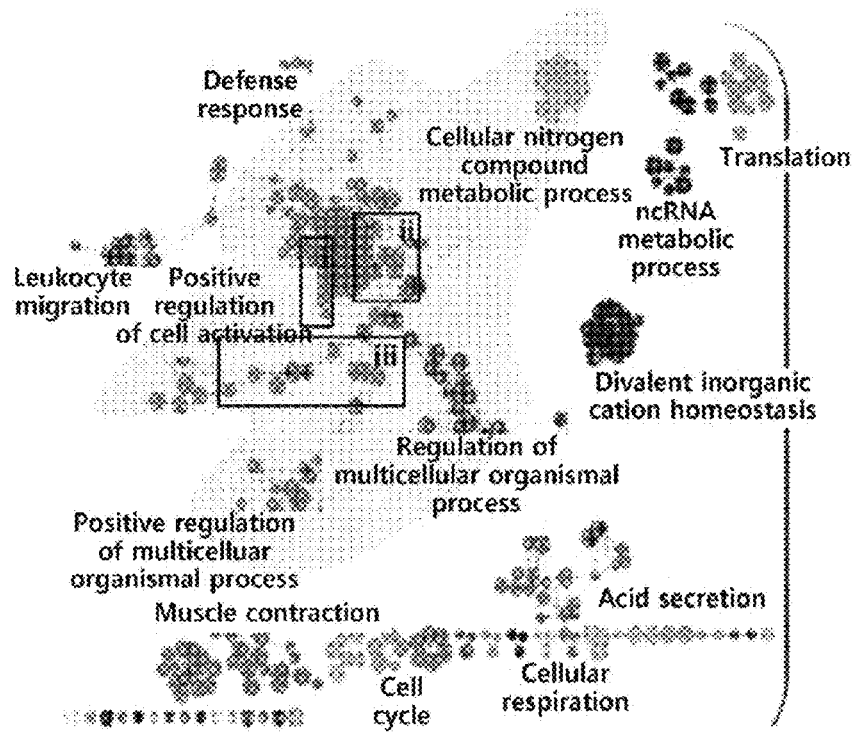

[FIG. 10c]
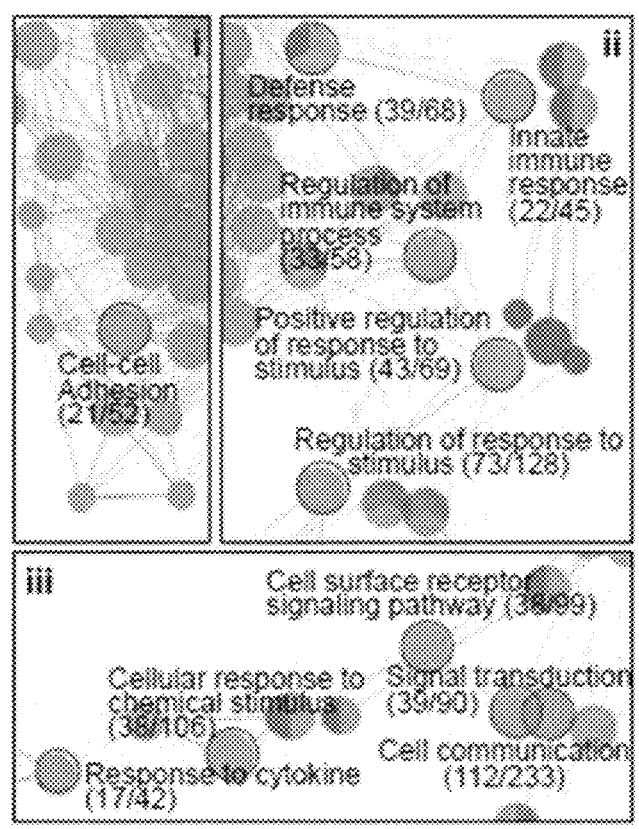

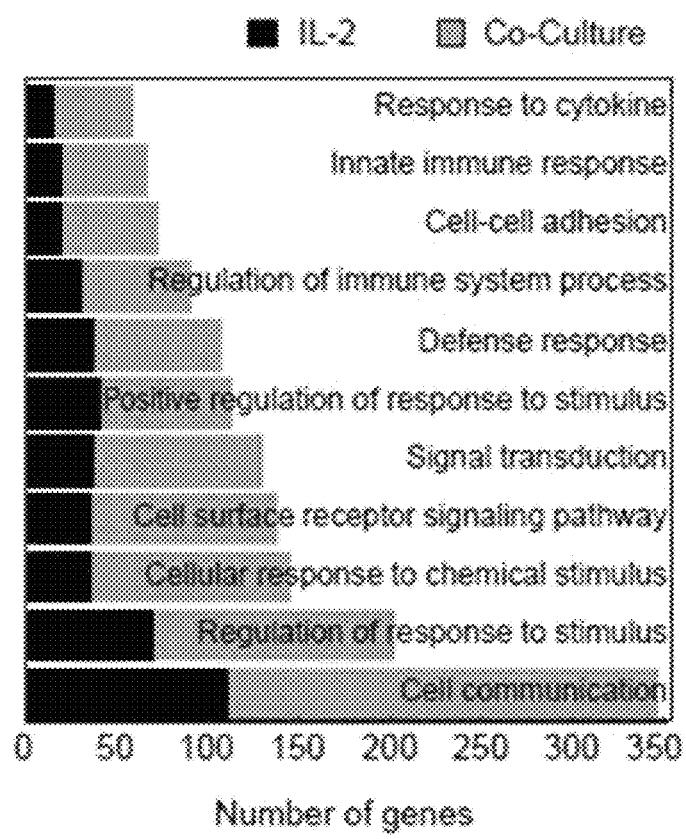
[FIG. 10d]

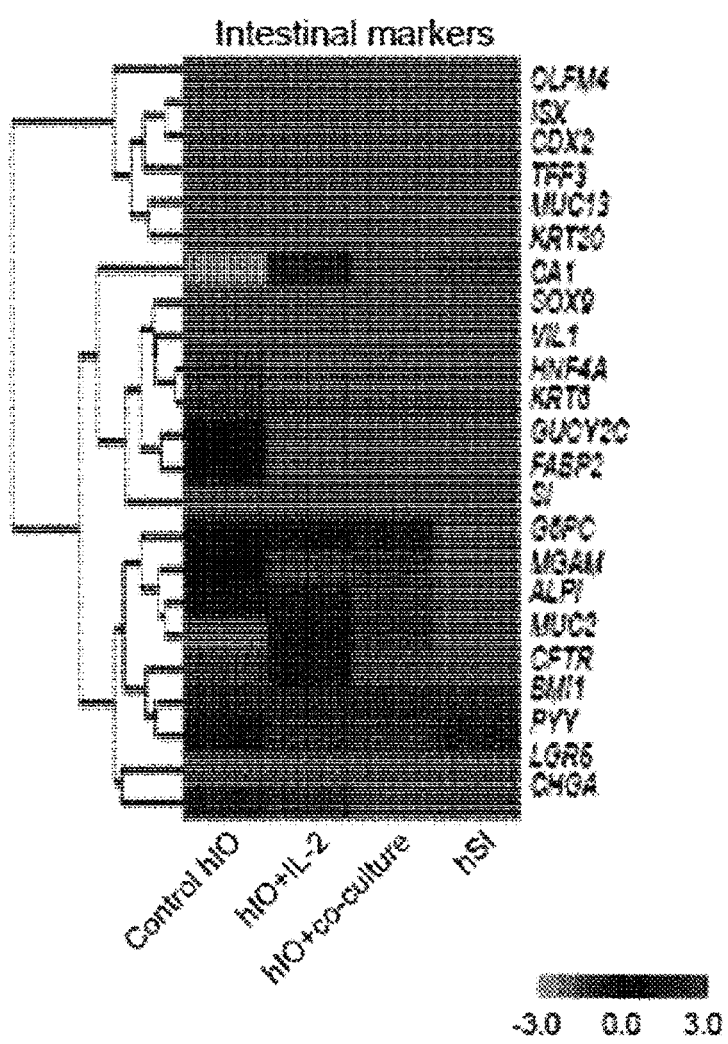
[FIG. 10e]

[FIG. 10f]
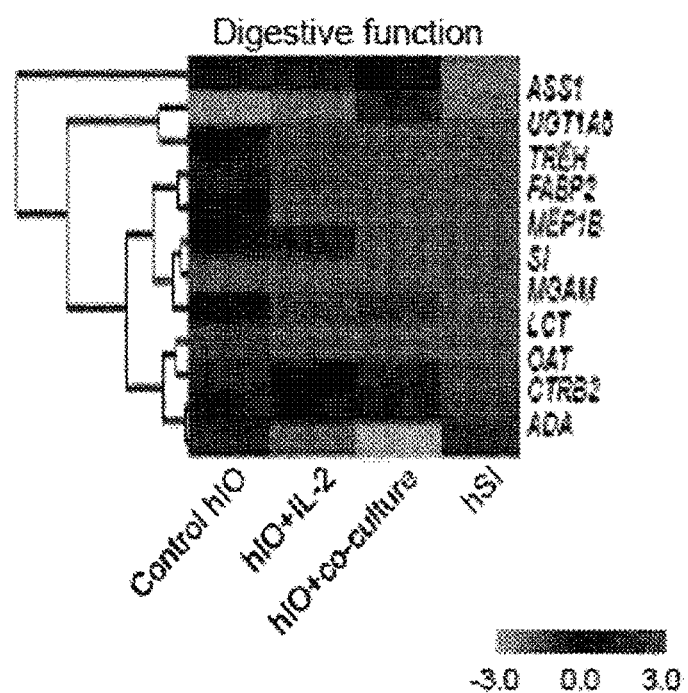

[FIG. 10g]
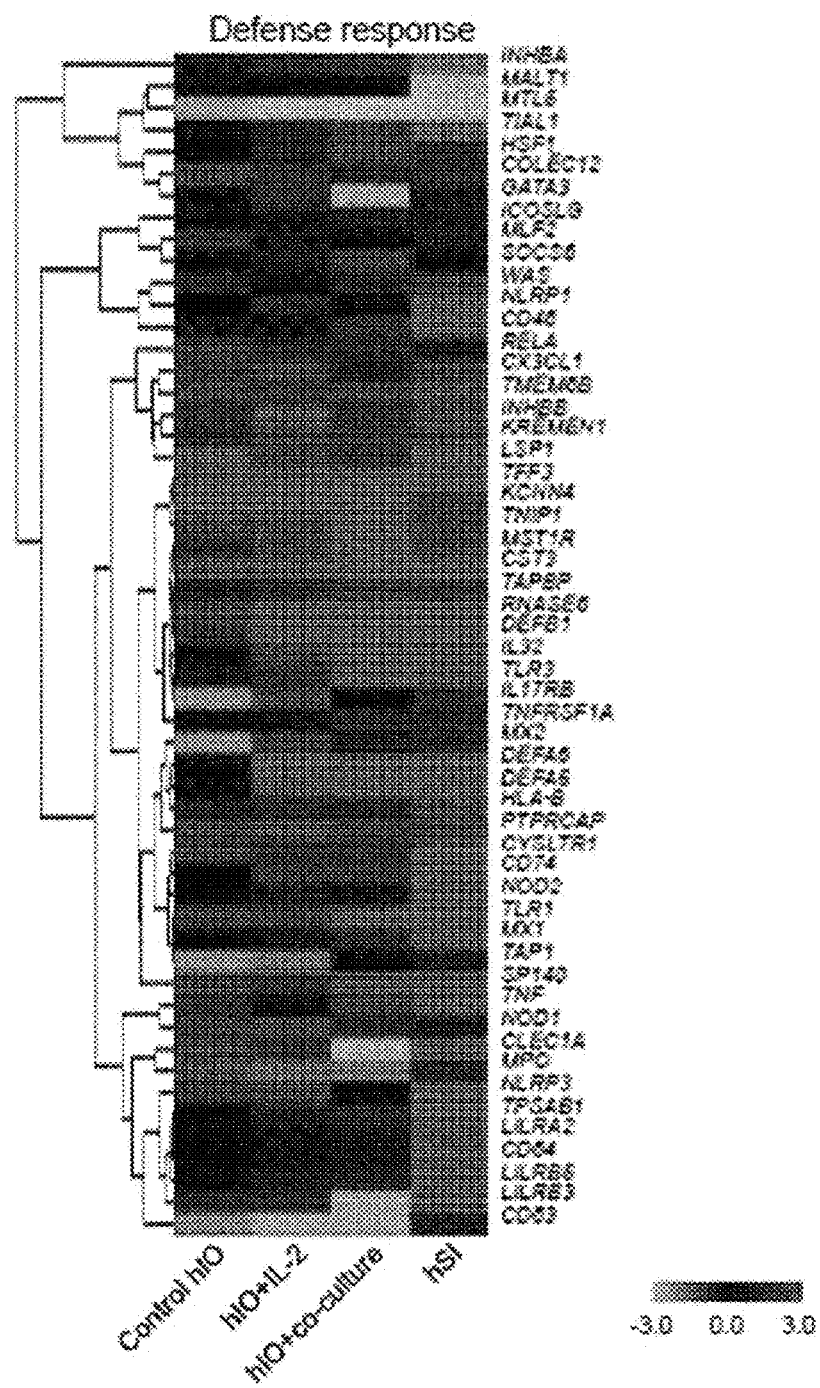

[FIG. 11a]
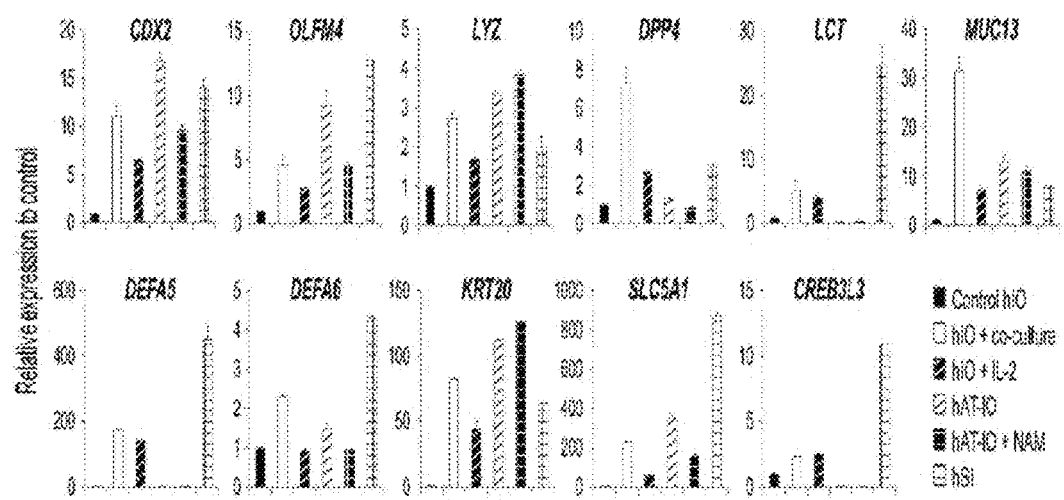
[FIG. 11b]
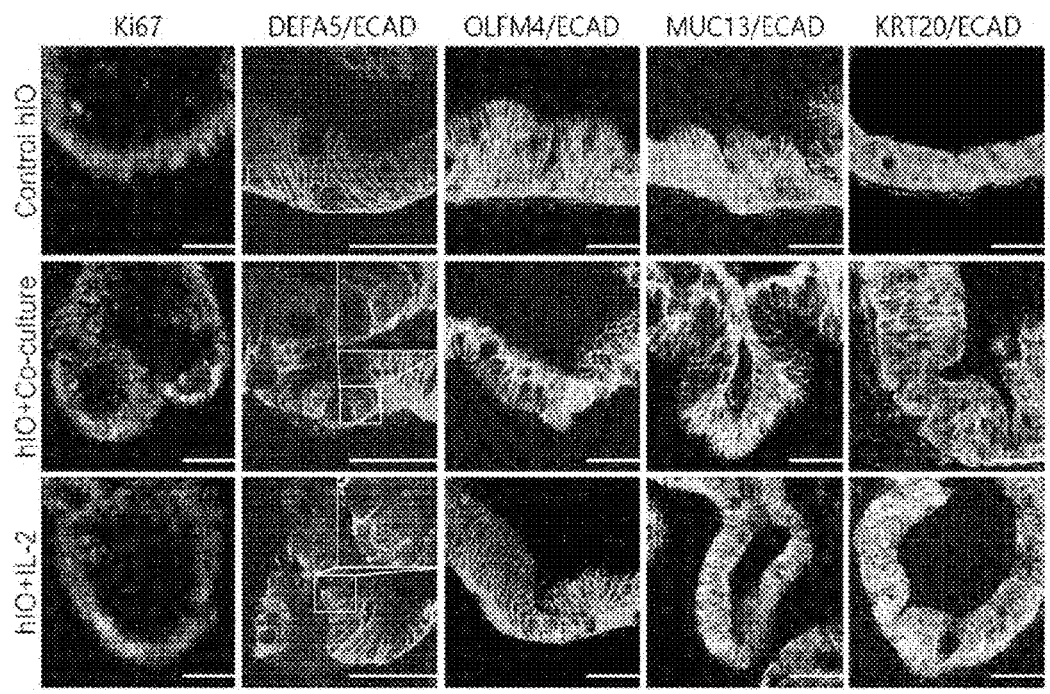

[FIG. 11c]
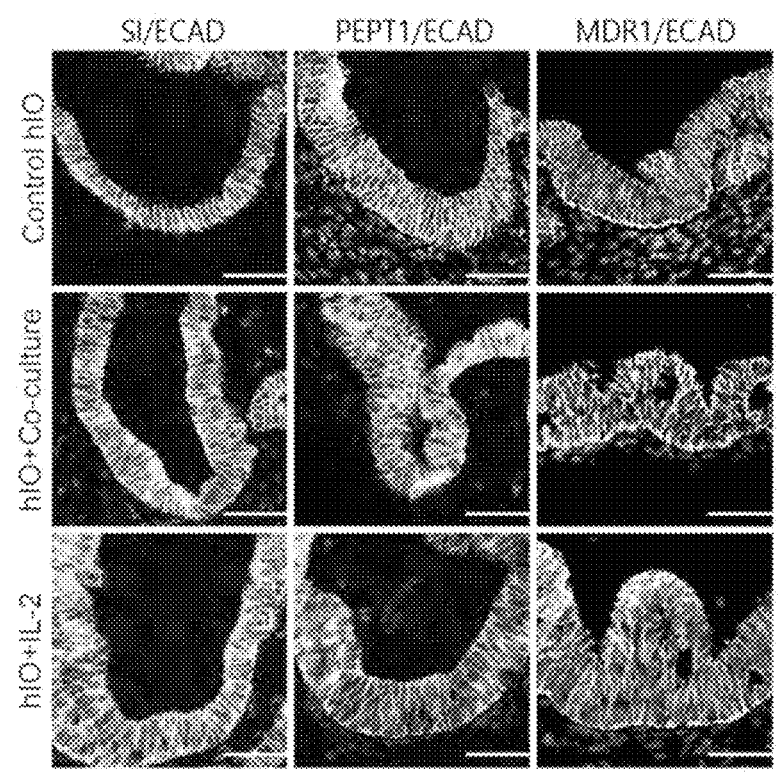

[FIG. 11d]
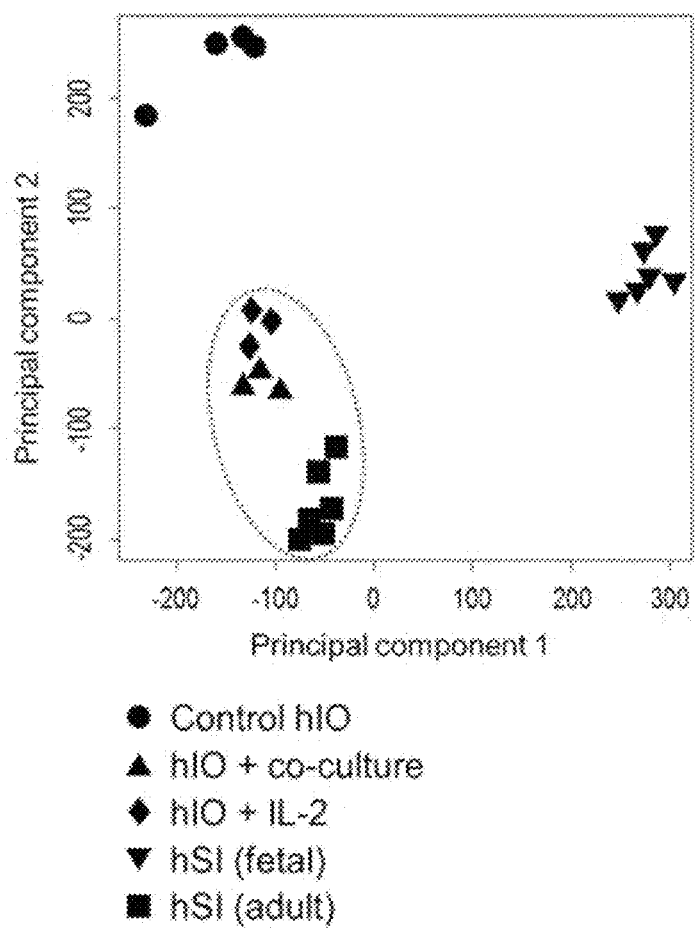

[FIG. 11e]
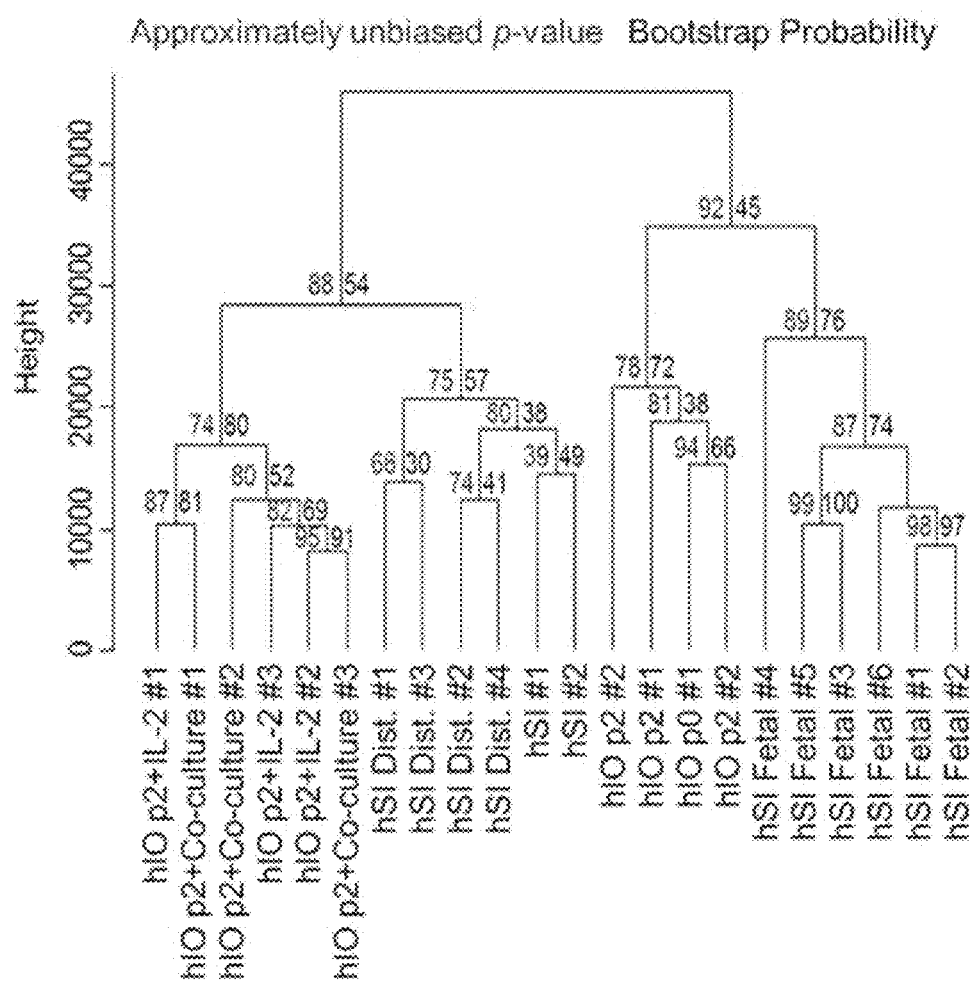

[FIG. 11f]
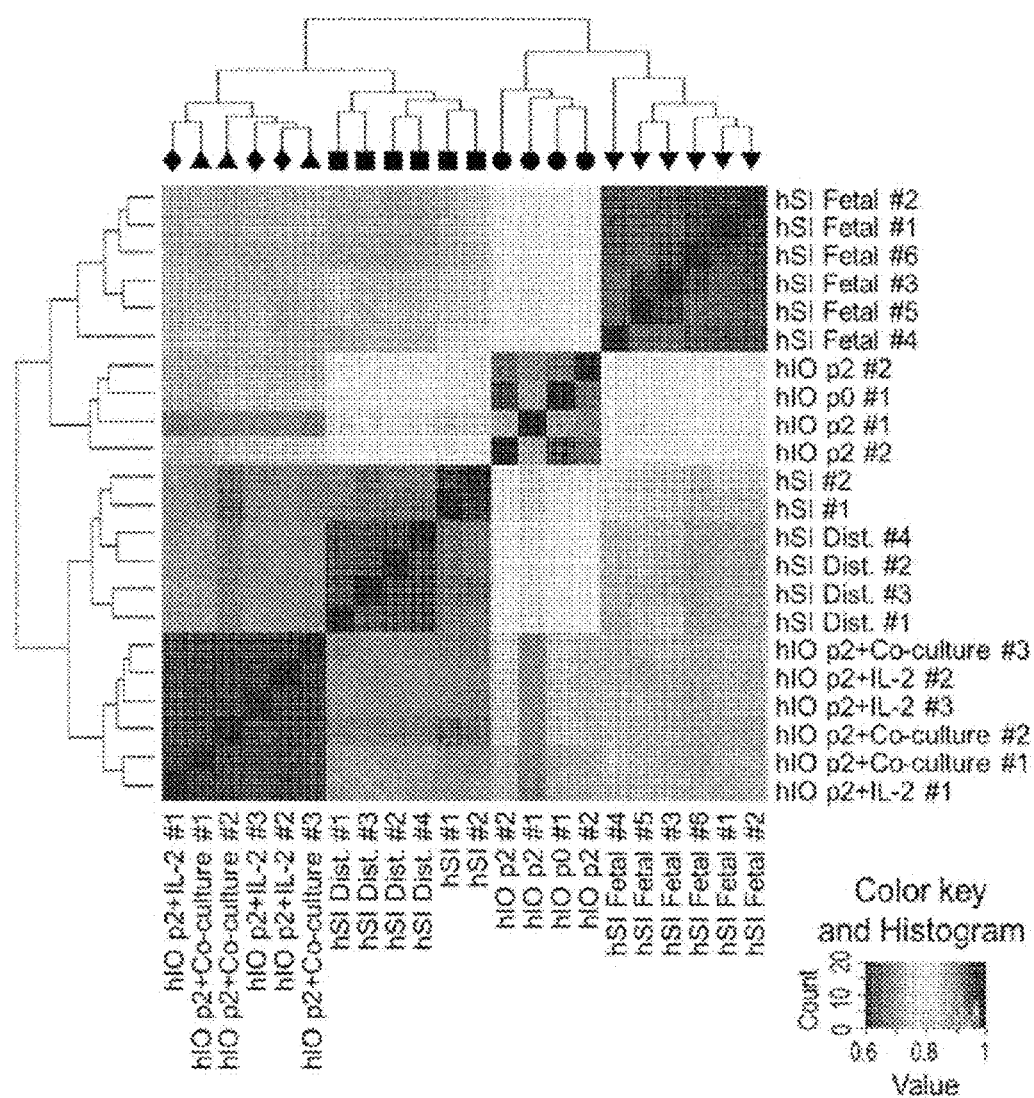

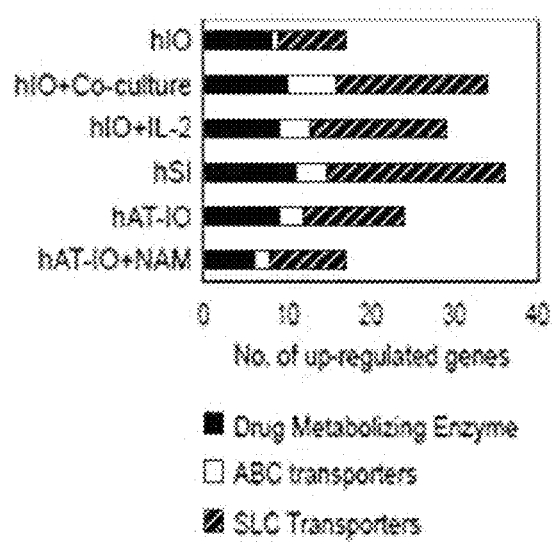
[FIG. 12a]

[FIG. 12b]
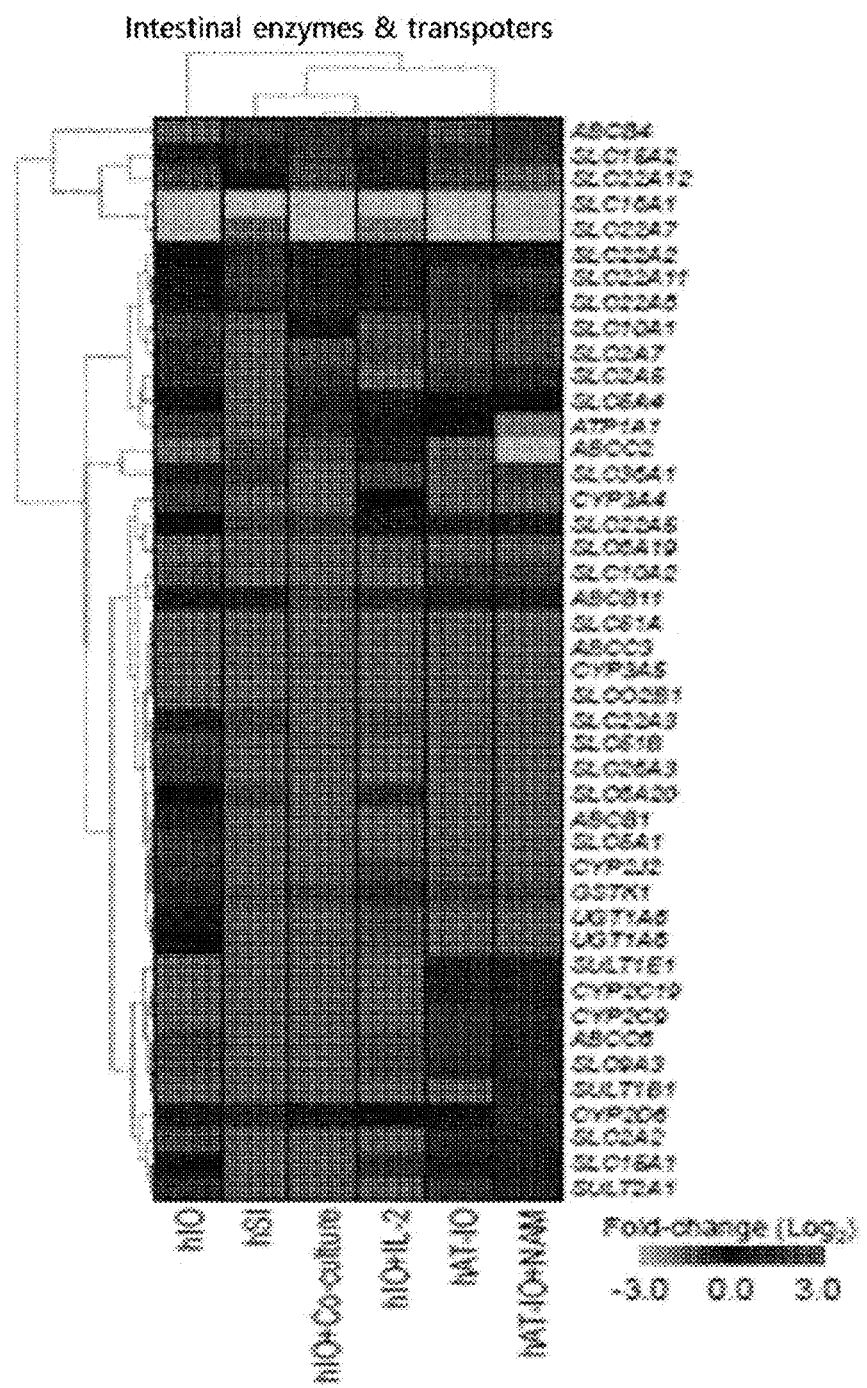

[FIG. 12c]
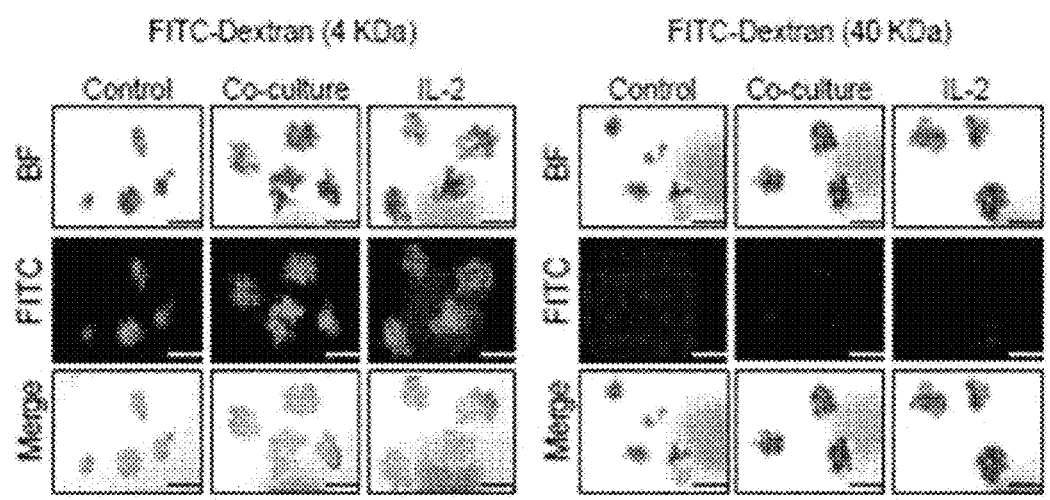

[FIG. 12d]
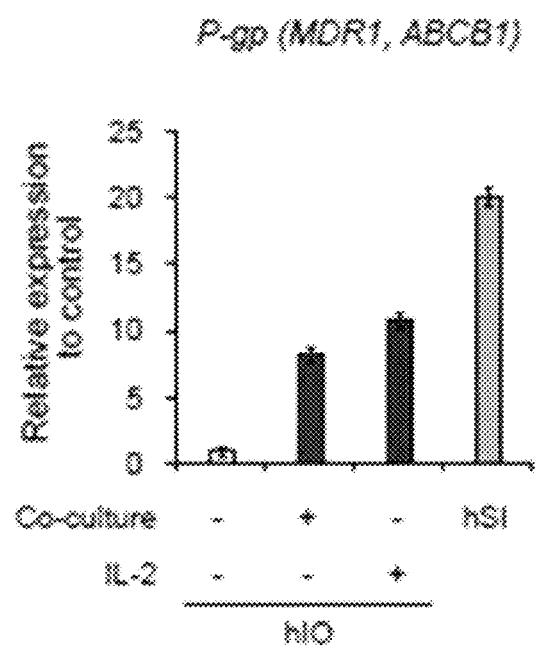

[FIG. 12e]
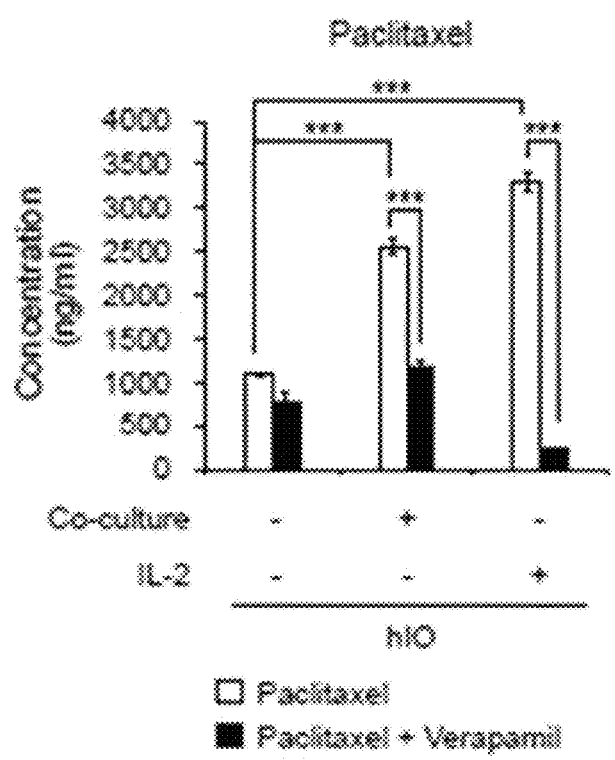

[FIG. 12f]
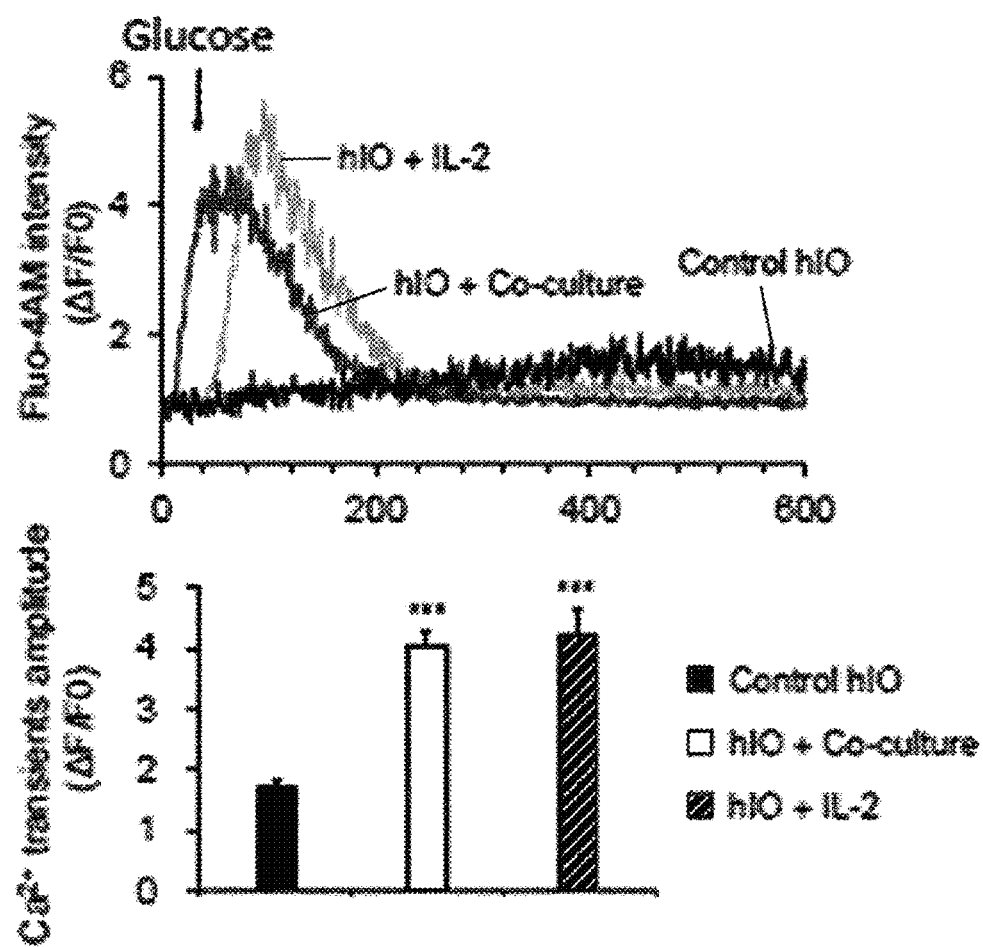

[FIG. 12g]
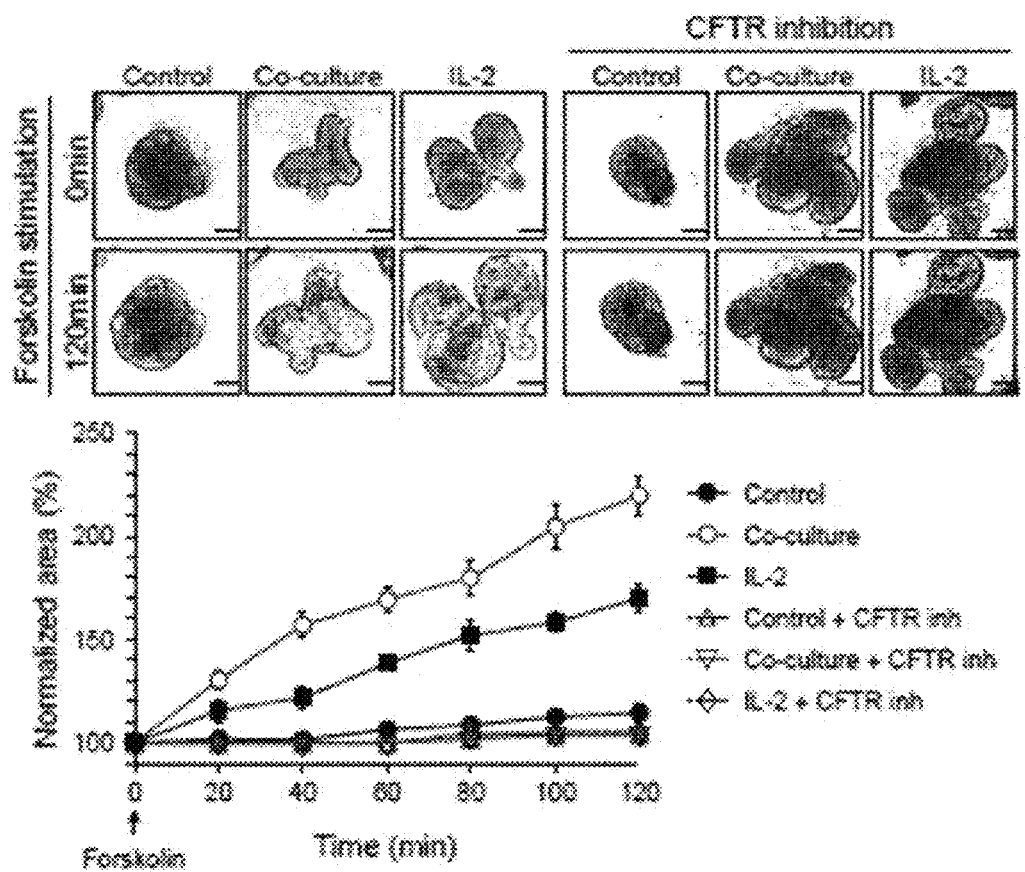

[FIG. 12h]
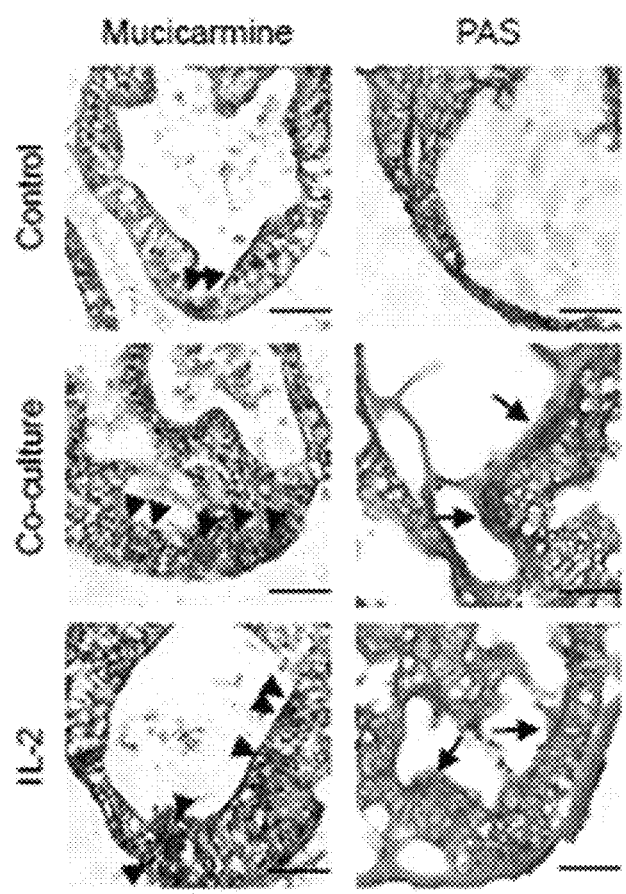

[FIG. 12i]
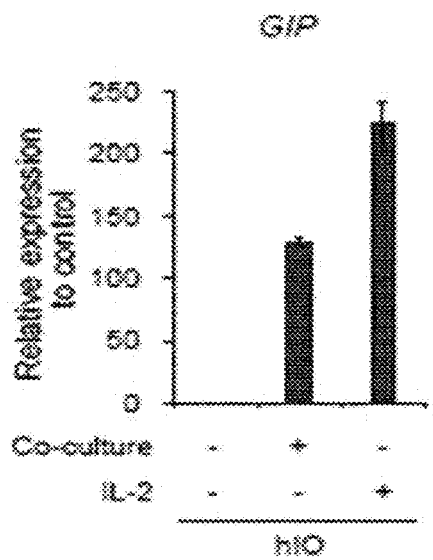
[FIG. 12j]
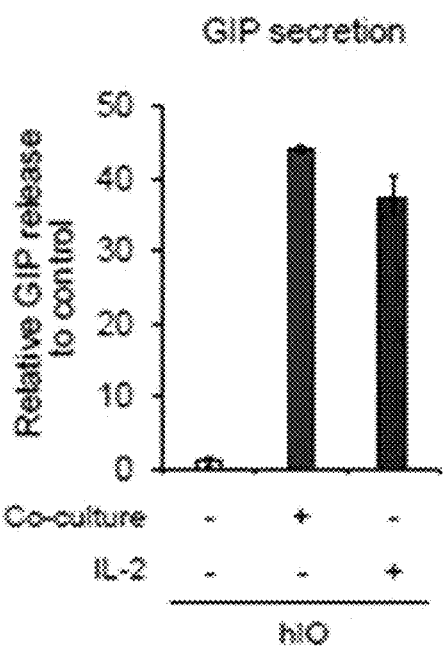

[FIG. 13a]
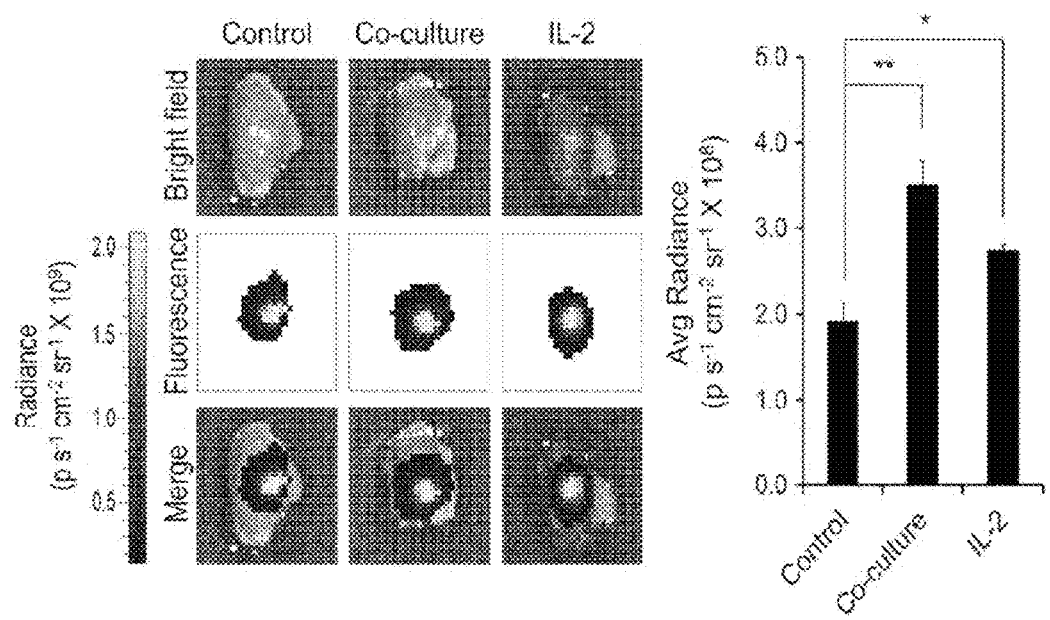
[FIG. 13b]
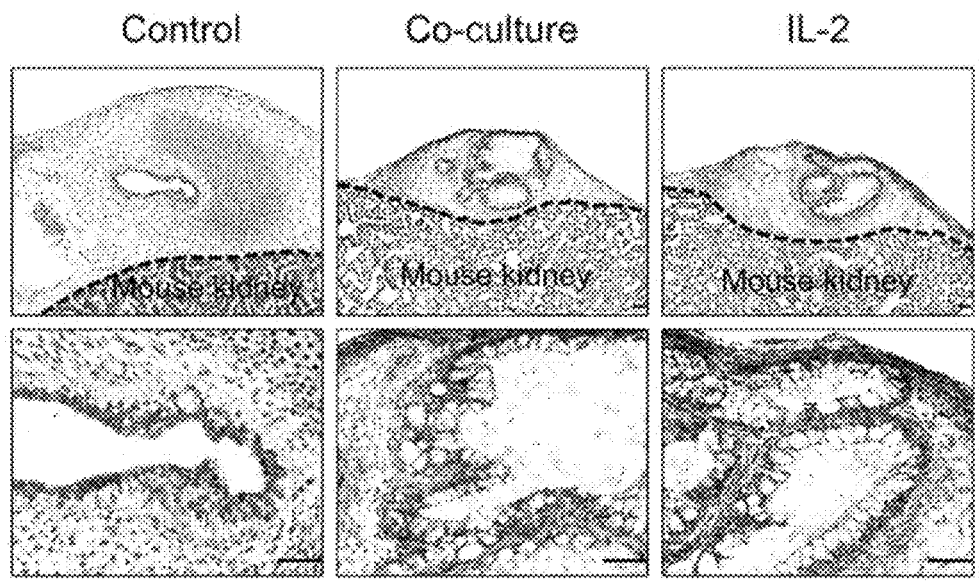

[FIG. 13c]
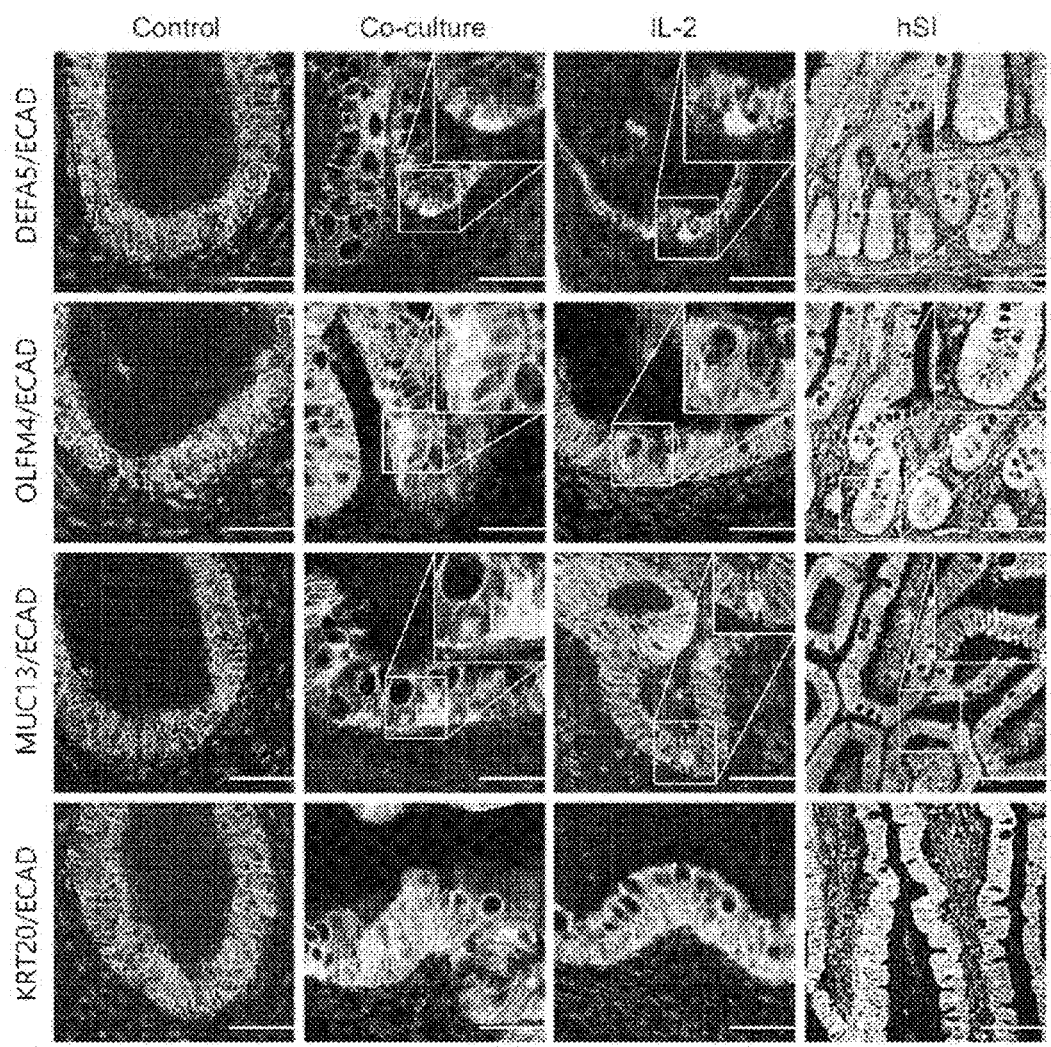

[FIG. 13d]
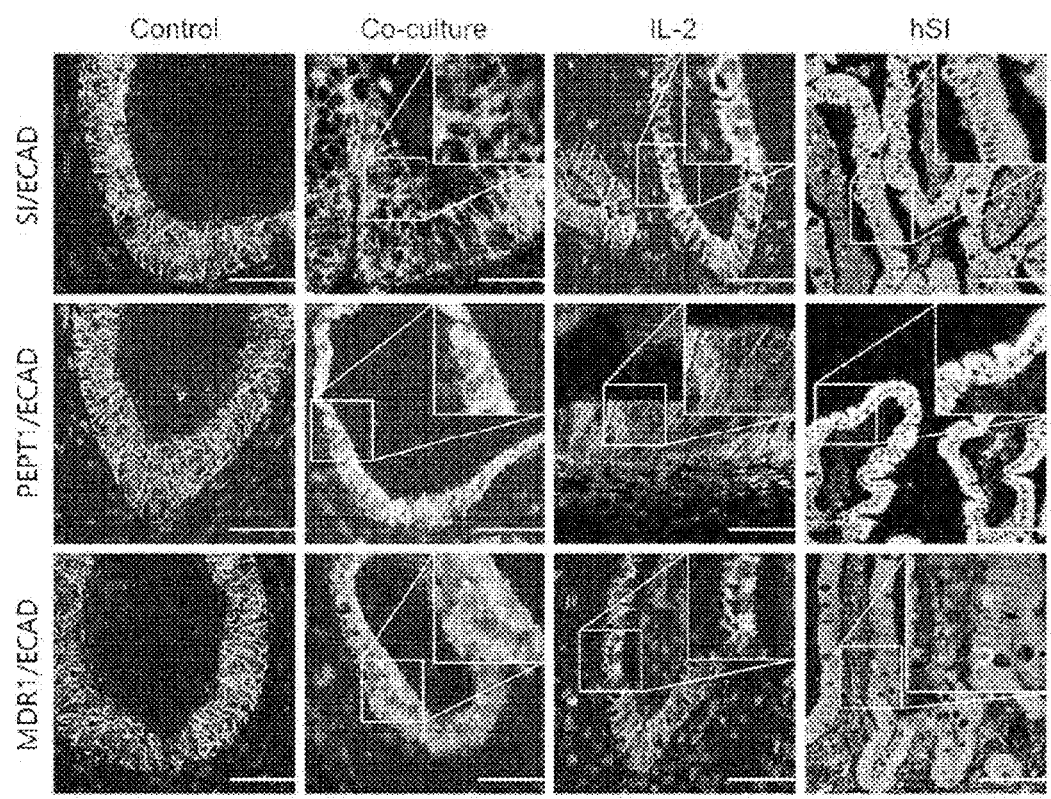

[FIG. 13e]
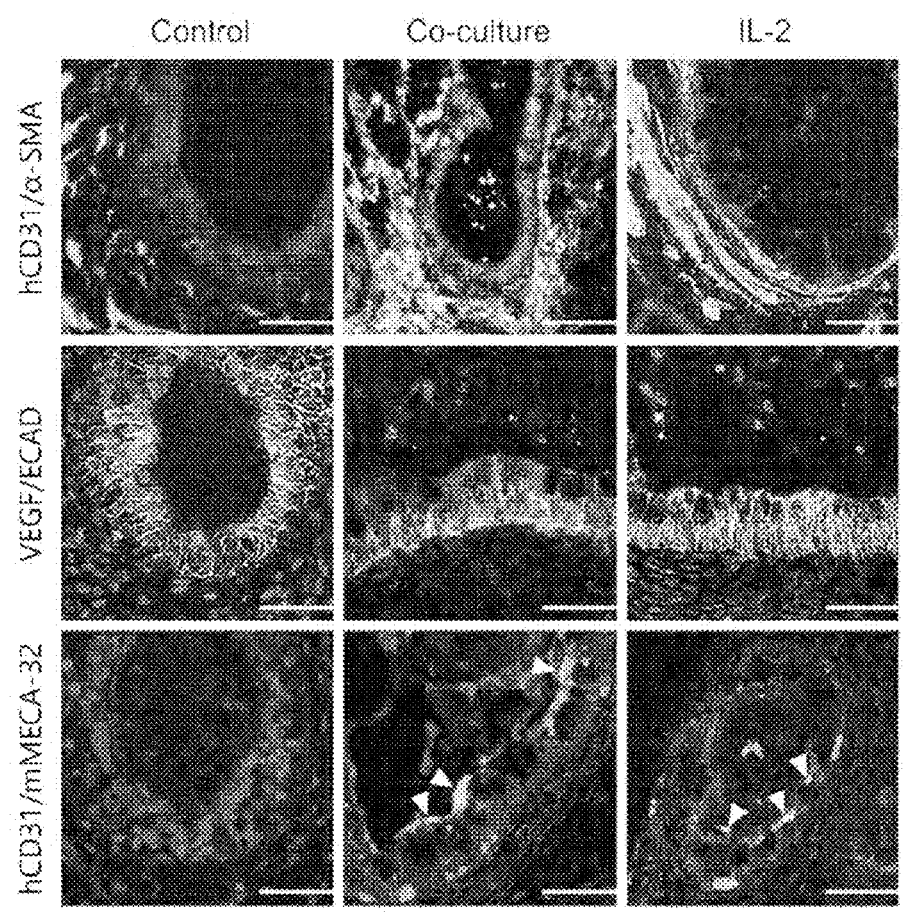

[FIG. 14a]
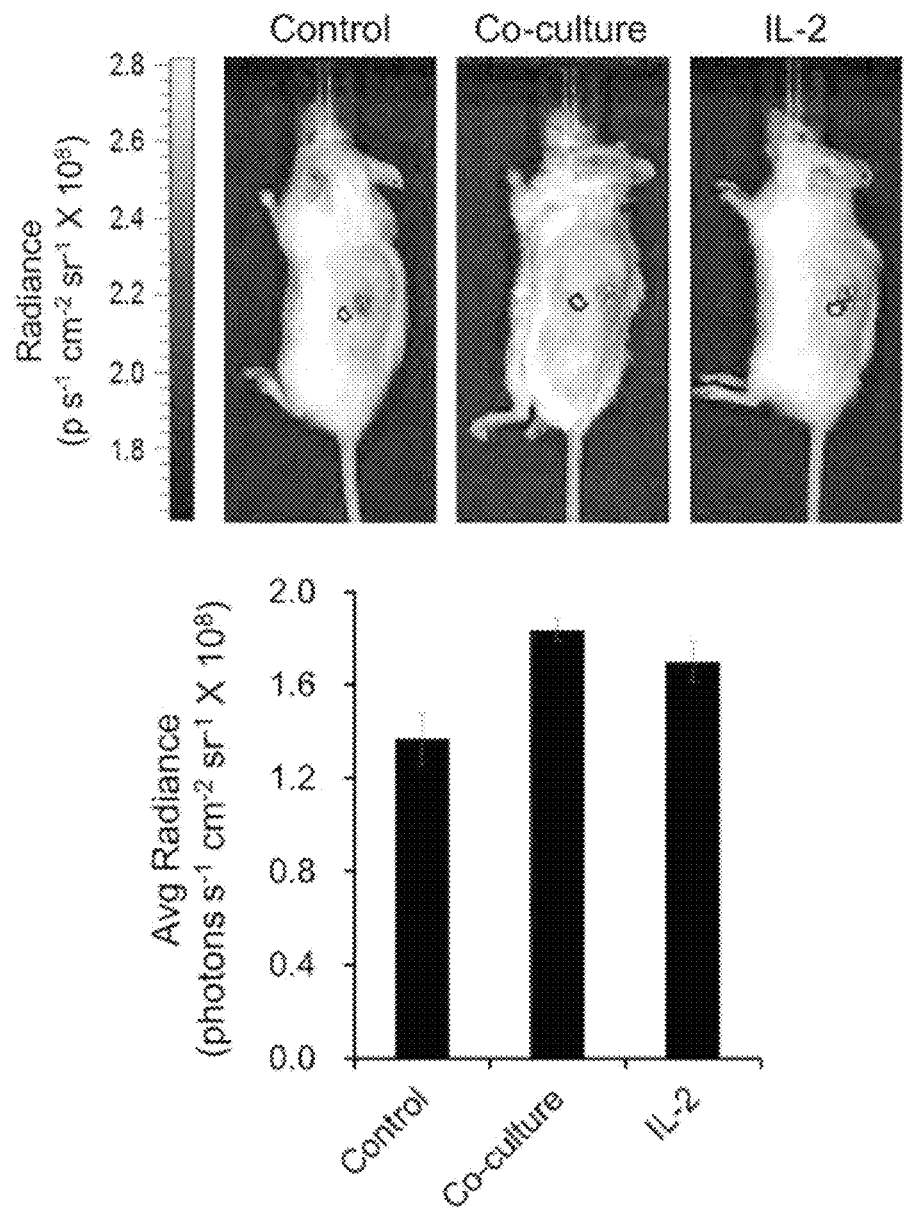

[FIG. 14b]
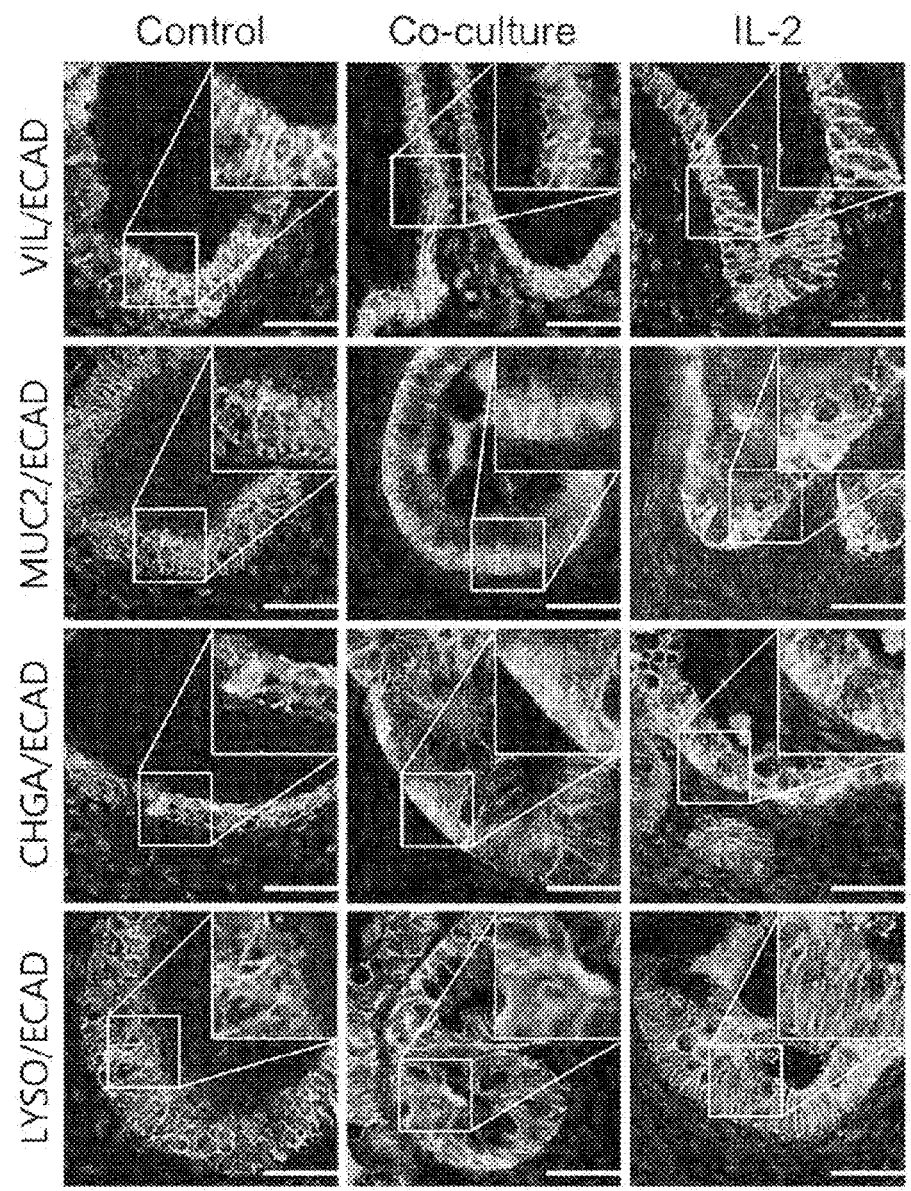

[FIG. 15a]
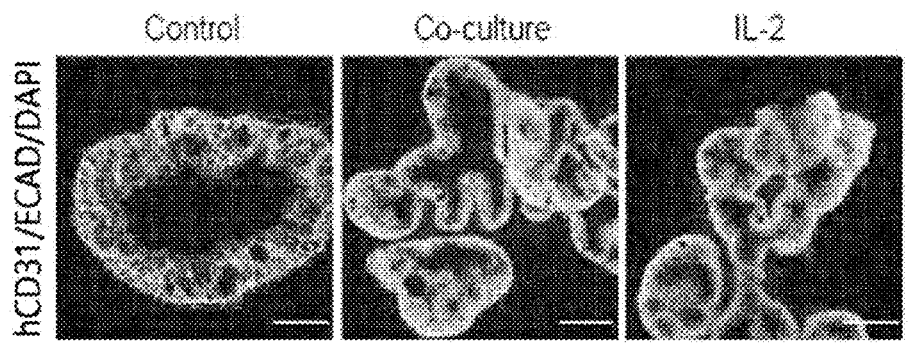
[FIG. 15b]
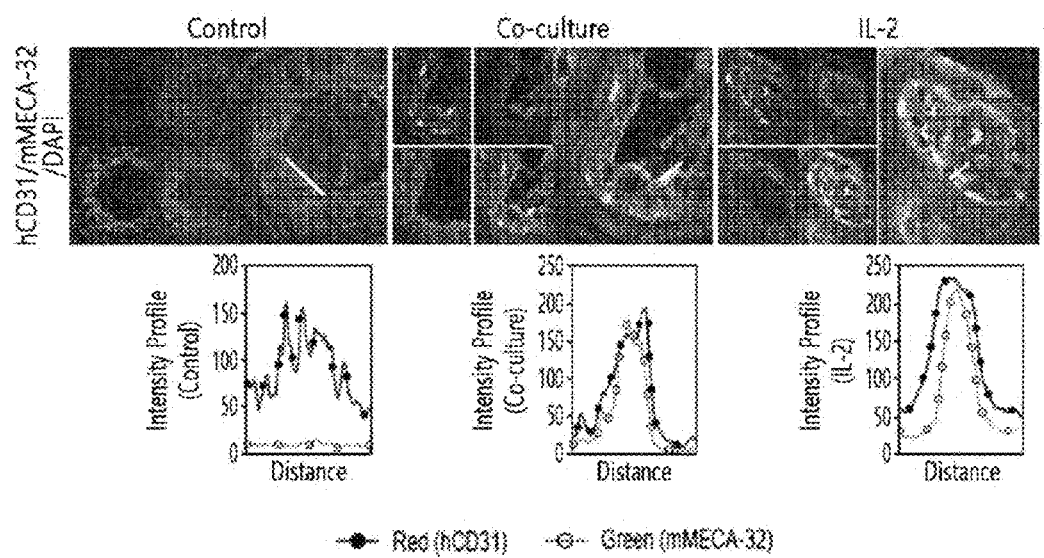

[FIG. 16]
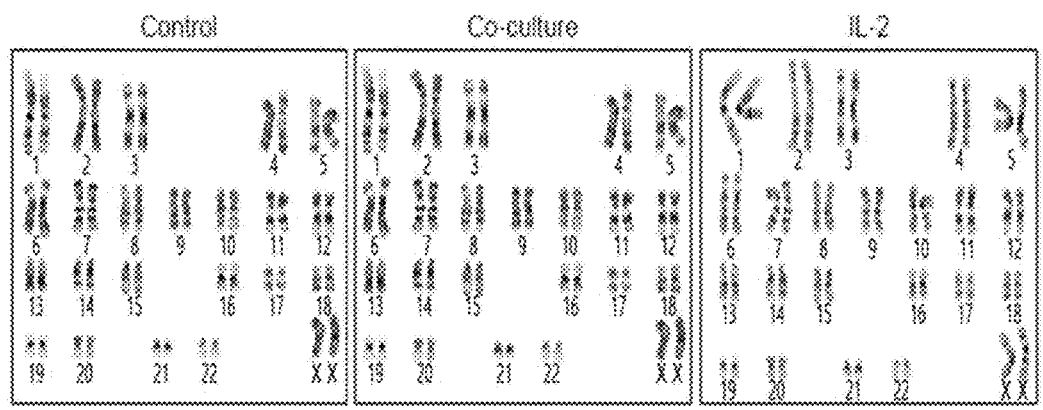
[FIG. 17a]
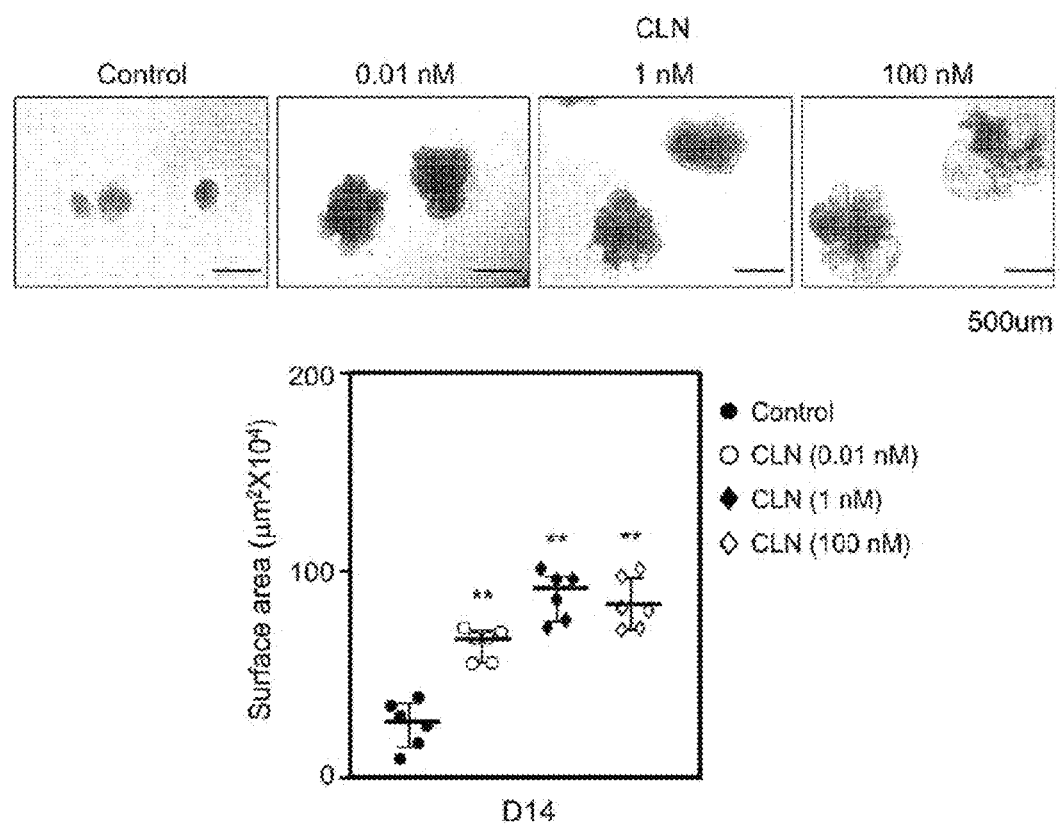

[FIG. 17b]
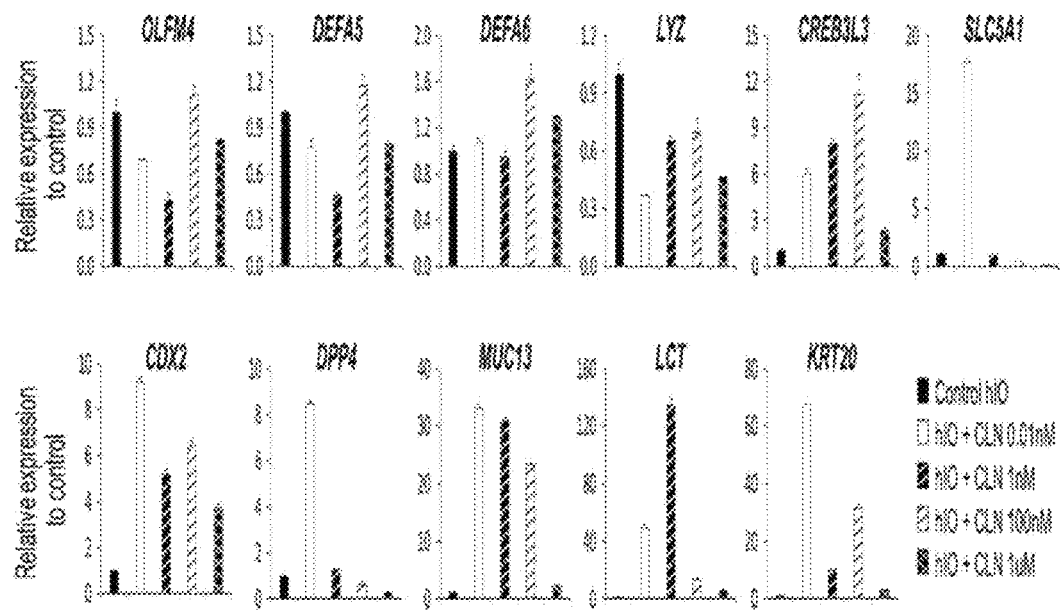
[FIG. 17c]
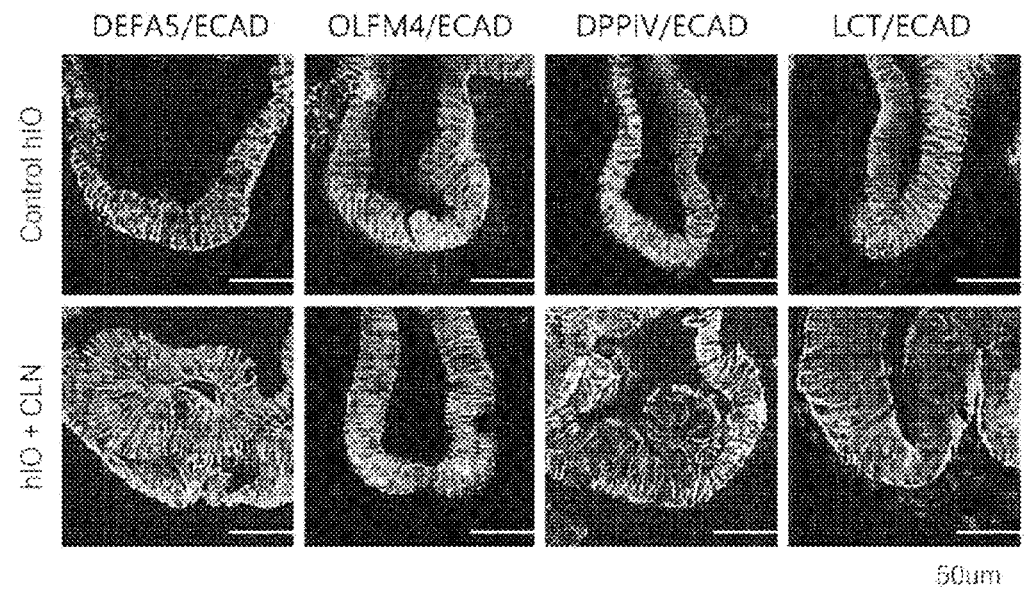

[FIG. 18a]
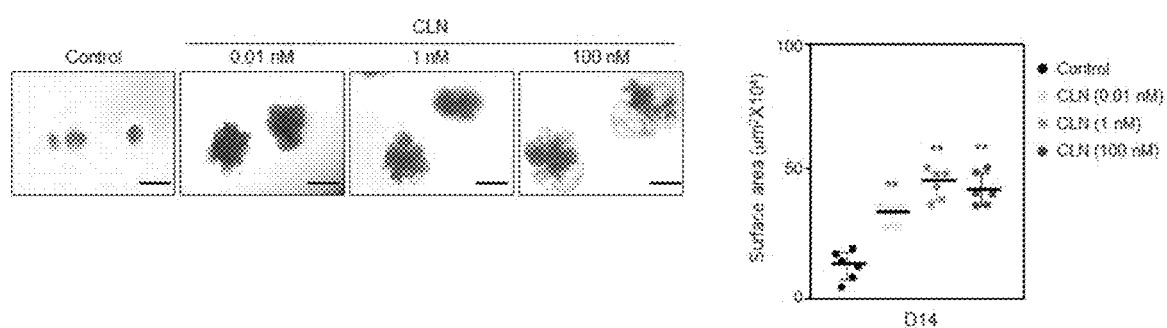
[FIG. 18b]
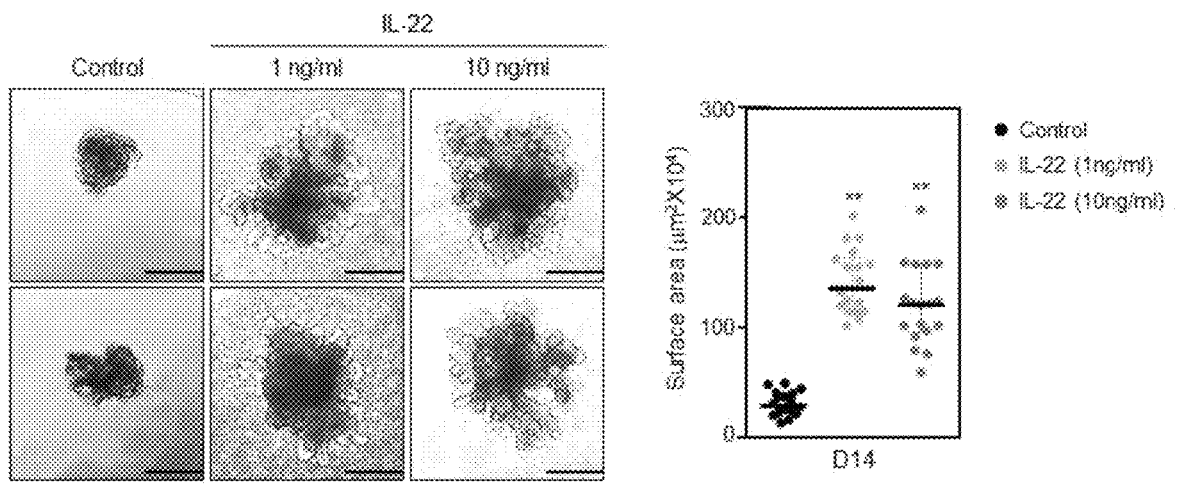

[FIG. 19]
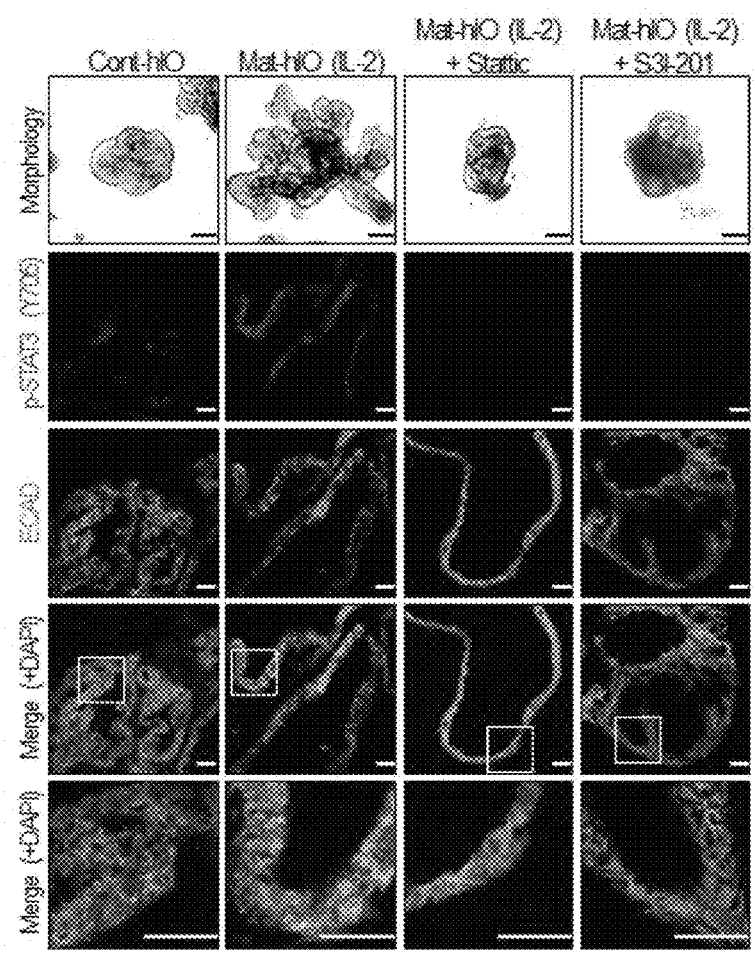

[FIG. 20a]
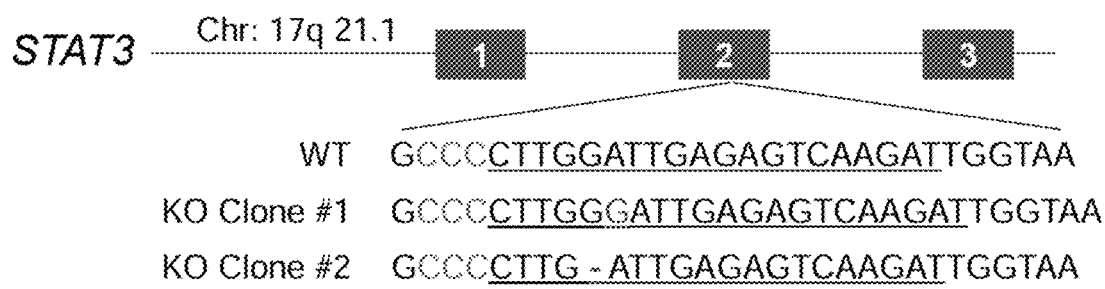
[FIG. 20b]
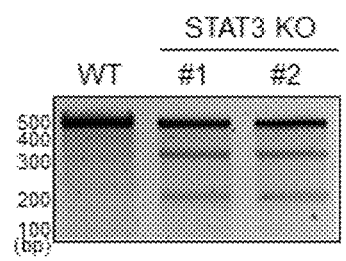
[FIG. 20c]
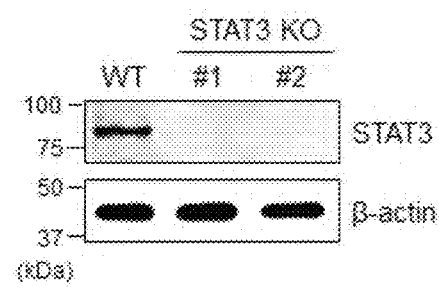

[FIG. 20d]
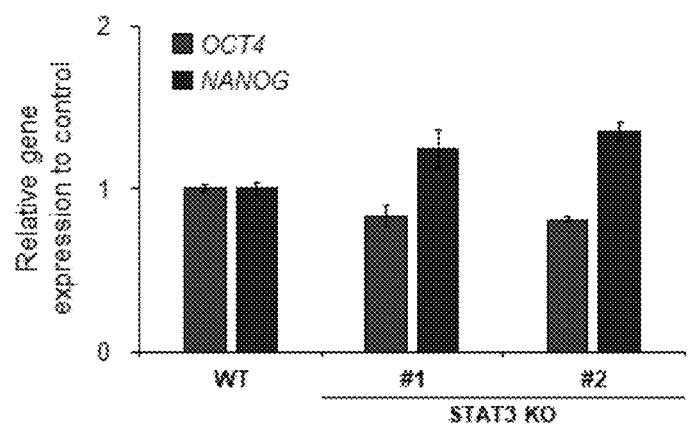
[FIG. 20e]
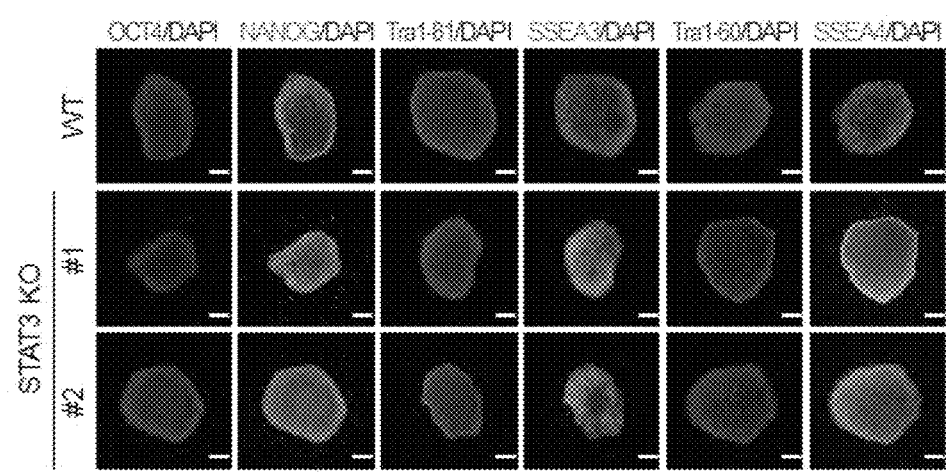

[FIG. 20f]
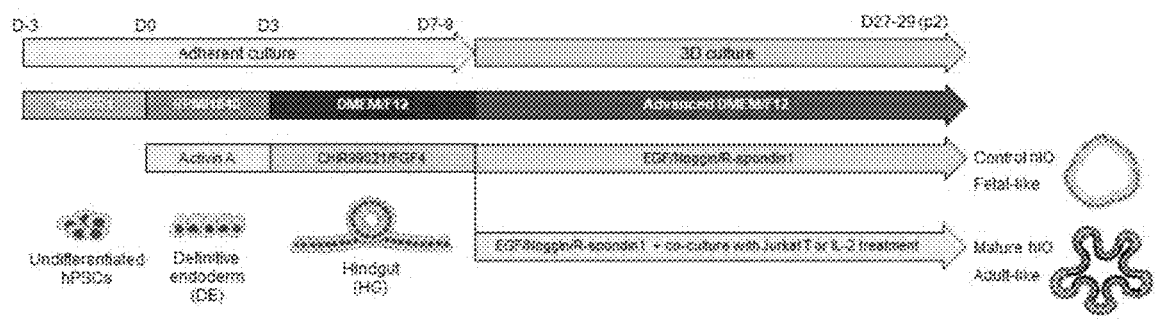
[FIG. 20g]
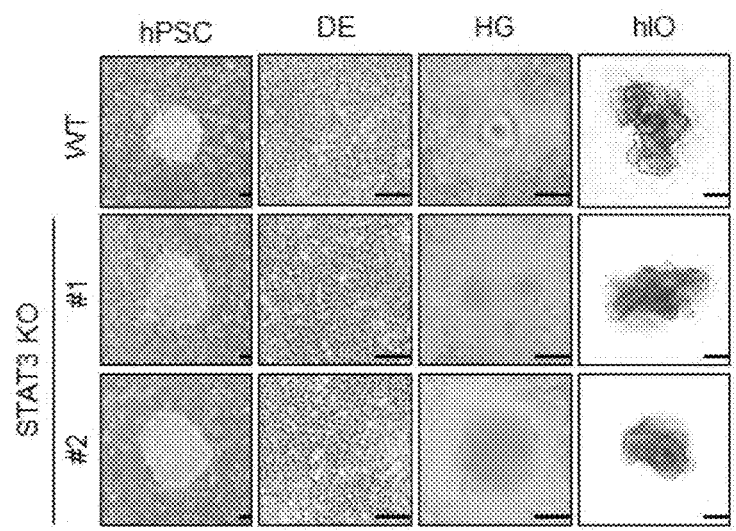

[FIG. 20h]
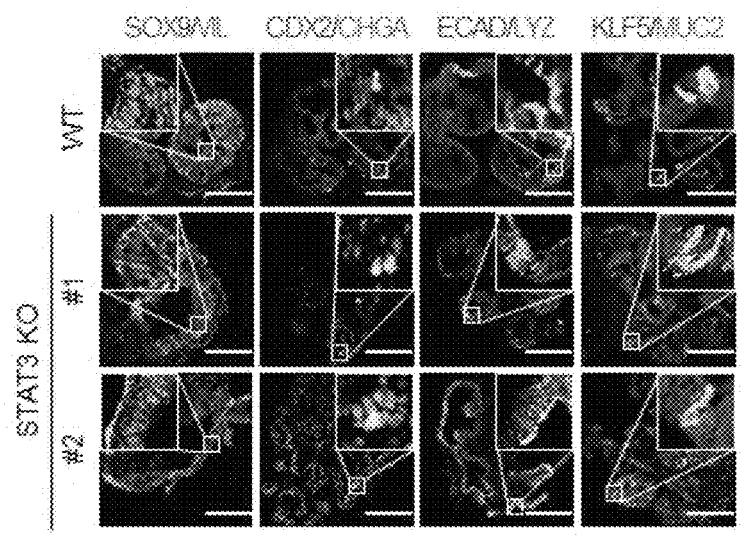
[FIG. 21a]
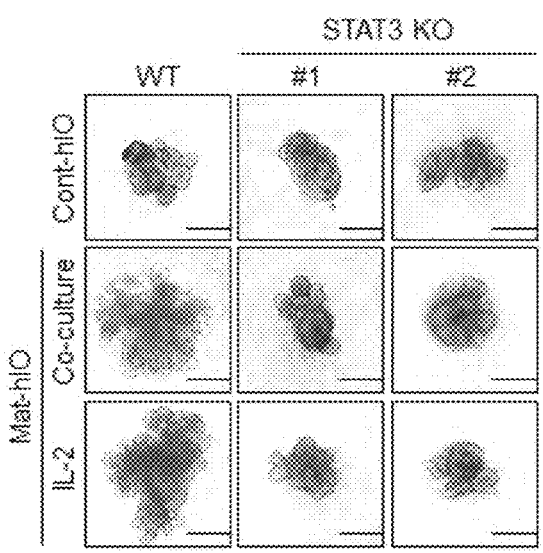

[FIG. 21b]
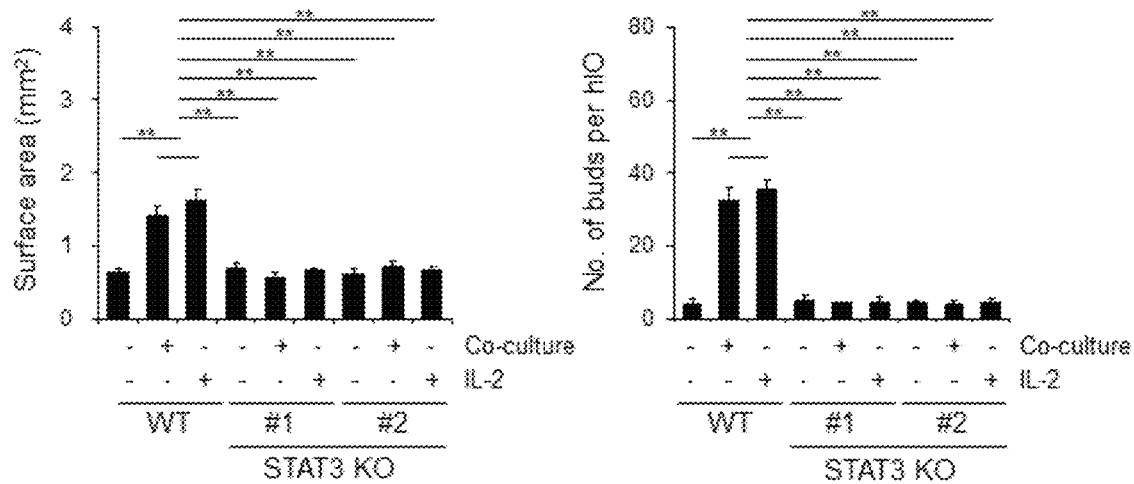
[FIG. 21c]
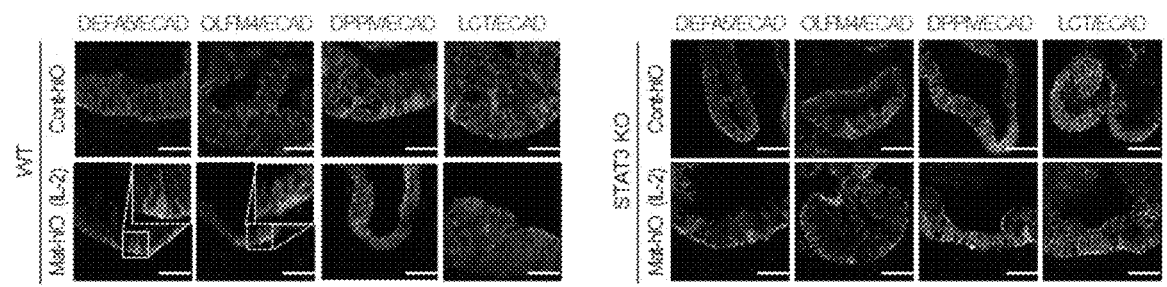

[FIG. 21d]
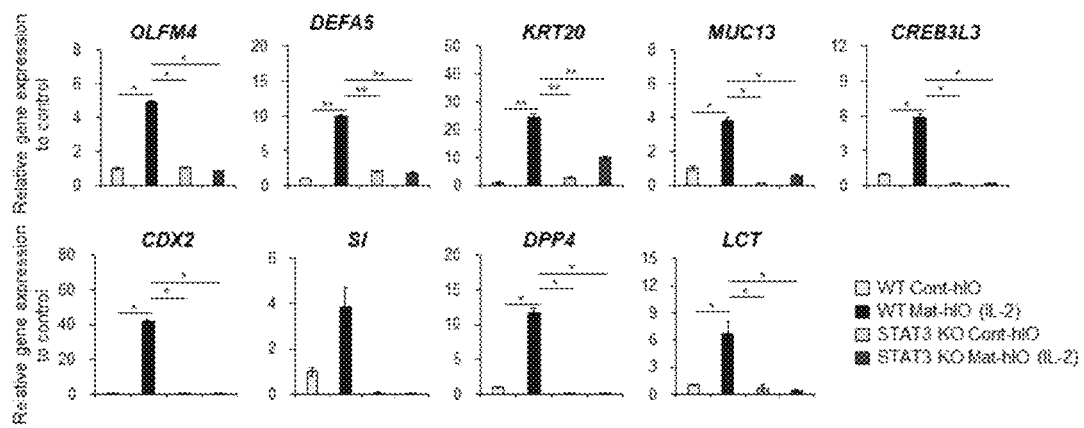

SEQUENCE LISTING

<160> NUMBER OF SEQ ID NOS: 44

<210> SEQ ID NO 1
<211> LENGTH: 19
<212> TYPE: DNA
<213> ORGANISM: Artificial Sequence
<220> FEATURE:
<223> OTHER INFORMATION: Forward primer for GAPDH

<400> SEQUENCE: 1
gaaggtgaag gtcggagtc                                                  19

<210> SEQ ID NO 2
<211> LENGTH: 20
<212> TYPE: DNA
<213> ORGANISM: Artificial Sequence
<220> FEATURE:
<223> OTHER INFORMATION: Reverse primer for GAPDH

<400> SEQUENCE: 2
gaagatggtg atgggatttc                                                 20

<210> SEQ ID NO 3
<211> LENGTH: 22
<212> TYPE: DNA
<213> ORGANISM: Artificial Sequence
<220> FEATURE:
<223> OTHER INFORMATION: Forward primer for CDX2

<400> SEQUENCE: 3
ctggagctgg agaaggagtt tc                                              22

<210> SEQ ID NO 4
<211> LENGTH: 24
<212> TYPE: DNA
<213> ORGANISM: Artificial Sequence
<220> FEATURE:
<223> OTHER INFORMATION: Reverse primer for CDX2

<400> SEQUENCE: 4
attttaacct gcctctcaga gagc                                            24

<210> SEQ ID NO 5
<211> LENGTH: 22
<212> TYPE: DNA
<213> ORGANISM: Artificial Sequence
<220> FEATURE:
<223> OTHER INFORMATION: Forward primer for SOX9

<400> SEQUENCE: 5
ggagagcgag gaggacaagt tc                                              22

<210> SEQ ID NO 6
<211> LENGTH: 19
<212> TYPE: DNA
<213> ORGANISM: Artificial Sequence
<220> FEATURE:
<223> OTHER INFORMATION: Reverse primer for SOX9

<400> SEQUENCE: 6
ttgaagatgg cgttggggg                                                  19

<210> SEQ ID NO 7
<211> LENGTH: 21
<212> TYPE: DNA
<213> ORGANISM: Artificial Sequence

```
<220> FEATURE:
<223> OTHER INFORMATION: Forward primer for LYZ

<400> SEQUENCE: 7
aaaaccccag gagcagttaa t                                          21

<210> SEQ ID NO 8
<211> LENGTH: 20
<212> TYPE: DNA
<213> ORGANISM: Artificial Sequence
<220> FEATURE:
<223> OTHER INFORMATION: Reverse primer for LYZ

<400> SEQUENCE: 8
caaccctctt tgcacaagct                                            20

<210> SEQ ID NO 9
<211> LENGTH: 20
<212> TYPE: DNA
<213> ORGANISM: Artificial Sequence
<220> FEATURE:
<223> OTHER INFORMATION: Forward primer for VIL1

<400> SEQUENCE: 9
agccagatca ctgctgaggt                                            20

<210> SEQ ID NO 10
<211> LENGTH: 20
<212> TYPE: DNA
<213> ORGANISM: Artificial Sequence
<220> FEATURE:
<223> OTHER INFORMATION: Reverse primer for VIL1

<400> SEQUENCE: 10
tggacaggtg ttcctccttc                                            20

<210> SEQ ID NO 11
<211> LENGTH: 20
<212> TYPE: DNA
<213> ORGANISM: Artificial Sequence
<220> FEATURE:
<223> OTHER INFORMATION: Forward primer for CHGA

<400> SEQUENCE: 11
tgacctcaac gatgcatttc                                            20

<210> SEQ ID NO 12
<211> LENGTH: 20
<212> TYPE: DNA
<213> ORGANISM: Artificial Sequence
<220> FEATURE:
<223> OTHER INFORMATION: Reverse primer for CHGA

<400> SEQUENCE: 12
ctgtcctggc tcttctgctc                                            20

<210> SEQ ID NO 13
<211> LENGTH: 20
<212> TYPE: DNA
<213> ORGANISM: Artificial Sequence
<220> FEATURE:
<223> OTHER INFORMATION: Forward primer for MUC2

<400> SEQUENCE: 13
tgtaggcatc gctcttctca                                            20
```

```
<210> SEQ ID NO 14
<211> LENGTH: 20
<212> TYPE: DNA
<213> ORGANISM: Artificial Sequence
<220> FEATURE:
<223> OTHER INFORMATION: Reverse primer for MUC2

<400> SEQUENCE: 14
gacaccatct acctcacccg                                                   20

<210> SEQ ID NO 15
<211> LENGTH: 20
<212> TYPE: DNA
<213> ORGANISM: Artificial Sequence
<220> FEATURE:
<223> OTHER INFORMATION: Forward primer for ISX

<400> SEQUENCE: 15
caggaaggaa ggaagagcaa                                                   20

<210> SEQ ID NO 16
<211> LENGTH: 21
<212> TYPE: DNA
<213> ORGANISM: Artificial Sequence
<220> FEATURE:
<223> OTHER INFORMATION: Reverse primer for ISX

<400> SEQUENCE: 16
tgggtagtgg gtaaagtgga a                                                 21

<210> SEQ ID NO 17
<211> LENGTH: 20
<212> TYPE: DNA
<213> ORGANISM: Artificial Sequence
<220> FEATURE:
<223> OTHER INFORMATION: Forward primer for LGR5

<400> SEQUENCE: 17
tgctcttcac caactgcatc                                                   20

<210> SEQ ID NO 18
<211> LENGTH: 20
<212> TYPE: DNA
<213> ORGANISM: Artificial Sequence
<220> FEATURE:
<223> OTHER INFORMATION: Reverse primer for LGR5

<400> SEQUENCE: 18
ctcaggctca ccagatcctc                                                   20

<210> SEQ ID NO 19
<211> LENGTH: 20
<212> TYPE: DNA
<213> ORGANISM: Artificial Sequence
<220> FEATURE:
<223> OTHER INFORMATION: Forward primer for SI

<400> SEQUENCE: 19
ggtaaggaga aaccgggaag                                                   20

<210> SEQ ID NO 20
<211> LENGTH: 20
<212> TYPE: DNA
<213> ORGANISM: Artificial Sequence
<220> FEATURE:
<223> OTHER INFORMATION: Reverse primer for SI
```

```
<400> SEQUENCE: 20
gcacgtcgac ctatggaaat                                               20

<210> SEQ ID NO 21
<211> LENGTH: 24
<212> TYPE: DNA
<213> ORGANISM: Artificial Sequence
<220> FEATURE:
<223> OTHER INFORMATION: Forward primer for VIM

<400> SEQUENCE: 21
agaacgtgca ggaggcagaa gaat                                          24

<210> SEQ ID NO 22
<211> LENGTH: 24
<212> TYPE: DNA
<213> ORGANISM: Artificial Sequence
<220> FEATURE:
<223> OTHER INFORMATION: Reverse primer for VIM

<400> SEQUENCE: 22
ttccatttca cgcatctggc gttc                                          24

<210> SEQ ID NO 23
<211> LENGTH: 20
<212> TYPE: DNA
<213> ORGANISM: Artificial Sequence
<220> FEATURE:
<223> OTHER INFORMATION: Forward primer for OLFM4

<400> SEQUENCE: 23
acctttcccg tggacagagt                                               20

<210> SEQ ID NO 24
<211> LENGTH: 23
<212> TYPE: DNA
<213> ORGANISM: Artificial Sequence
<220> FEATURE:
<223> OTHER INFORMATION: Reverse primer for OLFM4

<400> SEQUENCE: 24
tggacatatt ccctcacttt gga                                           23

<210> SEQ ID NO 25
<211> LENGTH: 20
<212> TYPE: DNA
<213> ORGANISM: Artificial Sequence
<220> FEATURE:
<223> OTHER INFORMATION: Forward primer for DEFA5

<400> SEQUENCE: 25
cctttgcagg aaatggactc                                               20

<210> SEQ ID NO 26
<211> LENGTH: 20
<212> TYPE: DNA
<213> ORGANISM: Artificial Sequence
<220> FEATURE:
<223> OTHER INFORMATION: Reverse primer for DEFA5

<400> SEQUENCE: 26
ggactcacgg gtagcacaac                                               20

<210> SEQ ID NO 27
```

```
<211> LENGTH: 20
<212> TYPE: DNA
<213> ORGANISM: Artificial Sequence
<220> FEATURE:
<223> OTHER INFORMATION: Forward primer for DEFA6

<400> SEQUENCE: 27
gcctagacac tgatgacccc                                              20

<210> SEQ ID NO 28
<211> LENGTH: 19
<212> TYPE: DNA
<213> ORGANISM: Artificial Sequence
<220> FEATURE:
<223> OTHER INFORMATION: Reverse primer for DEFA6

<400> SEQUENCE: 28
gcatgctgta ttgcgcctc                                               19

<210> SEQ ID NO 29
<211> LENGTH: 20
<212> TYPE: DNA
<213> ORGANISM: Artificial Sequence
<220> FEATURE:
<223> OTHER INFORMATION: Forward primer for KRT20

<400> SEQUENCE: 29
tggcctacac aagcatctgg                                              20

<210> SEQ ID NO 30
<211> LENGTH: 20
<212> TYPE: DNA
<213> ORGANISM: Artificial Sequence
<220> FEATURE:
<223> OTHER INFORMATION: Reverse primer for KRT20

<400> SEQUENCE: 30
taactggctg ctgtaacggg                                              20

<210> SEQ ID NO 31
<211> LENGTH: 20
<212> TYPE: DNA
<213> ORGANISM: Artificial Sequence
<220> FEATURE:
<223> OTHER INFORMATION: Forward primer for SLC5A1

<400> SEQUENCE: 31
gtgcagtcag cacaaagtgg                                              20

<210> SEQ ID NO 32
<211> LENGTH: 20
<212> TYPE: DNA
<213> ORGANISM: Artificial Sequence
<220> FEATURE:
<223> OTHER INFORMATION: Reverse primer for SLC5A1

<400> SEQUENCE: 32
atgcacatcc ggaatgggtt                                              20

<210> SEQ ID NO 33
<211> LENGTH: 20
<212> TYPE: DNA
<213> ORGANISM: Artificial Sequence
<220> FEATURE:
<223> OTHER INFORMATION: Forward primer for MUC13

<400> SEQUENCE: 33
```
cggatgactg cctcaatggt                                                 20

<210> SEQ ID NO 34
<211> LENGTH: 20
<212> TYPE: DNA
<213> ORGANISM: Artificial Sequence
<220> FEATURE:
<223> OTHER INFORMATION: Reverse primer for MUC13

<400> SEQUENCE: 34
aaagacgctc ccttctgctc                                                 20

<210> SEQ ID NO 35
<211> LENGTH: 20
<212> TYPE: DNA
<213> ORGANISM: Artificial Sequence
<220> FEATURE:
<223> OTHER INFORMATION: Forward primer for CREB3L3

<400> SEQUENCE: 35
atctcctgtt tgaccggcag                                                 20

<210> SEQ ID NO 36
<211> LENGTH: 20
<212> TYPE: DNA
<213> ORGANISM: Artificial Sequence
<220> FEATURE:
<223> OTHER INFORMATION: Reverse primer for CREB3L3

<400> SEQUENCE: 36
gtcgtcagag tcggggtttg                                                 20

<210> SEQ ID NO 37
<211> LENGTH: 20
<212> TYPE: DNA
<213> ORGANISM: Artificial Sequence
<220> FEATURE:
<223> OTHER INFORMATION: Forward primer for IL-2Ra

<400> SEQUENCE: 37
tcttcccatc ccacatcctc                                                 20

<210> SEQ ID NO 38
<211> LENGTH: 20
<212> TYPE: DNA
<213> ORGANISM: Artificial Sequence
<220> FEATURE:
<223> OTHER INFORMATION: Reverse primer for IL-2Ra

<400> SEQUENCE: 38
tctgcggaaa cctctcttgc                                                 20

<210> SEQ ID NO 39
<211> LENGTH: 20
<212> TYPE: DNA
<213> ORGANISM: Artificial Sequence
<220> FEATURE:
<223> OTHER INFORMATION: Forward primer for IL-2RB

<400> SEQUENCE: 39
ggcttttggc ttcatcatct                                                 20

<210> SEQ ID NO 40
<211> LENGTH: 20
<212> TYPE: DNA

```
-continued

<213> ORGANISM: Artificial Sequence
<220> FEATURE:
<223> OTHER INFORMATION: Reverse primer for IL-2RB

<400> SEQUENCE: 40
cttgtccctc tccagcactt                                               20

<210> SEQ ID NO 41
<211> LENGTH: 20
<212> TYPE: DNA
<213> ORGANISM: Artificial Sequence
<220> FEATURE:
<223> OTHER INFORMATION: Forward primer for IL-2Rrc

<400> SEQUENCE: 41
acgggaaccc aggagacagg                                               20

<210> SEQ ID NO 42
<211> LENGTH: 20
<212> TYPE: DNA
<213> ORGANISM: Artificial Sequence
<220> FEATURE:
<223> OTHER INFORMATION: Reverse primer for IL-2Rrc

<400> SEQUENCE: 42
agcggctccg aacacgaaac                                               20

<210> SEQ ID NO 43
<211> LENGTH: 20
<212> TYPE: DNA
<213> ORGANISM: Artificial Sequence
<220> FEATURE:
<223> OTHER INFORMATION: Forward primer for P-GP

<400> SEQUENCE: 43
gccaaagcca aaatatcagc                                               20

<210> SEQ ID NO 44
<211> LENGTH: 20
<212> TYPE: DNA
<213> ORGANISM: Artificial Sequence
<220> FEATURE:
<223> OTHER INFORMATION: Reverse primer for P-GP

<400> SEQUENCE: 44
ttccaatgtg ttcggcatta                                               20
```

METHOD OF PREPARING IN VITRO-MATURED HUMAN INTESTINAL ORGANOIDS AND USE THEREOF

SEQUENCE LISTING SUBMISSION VIA EFS-WEB

A computer readable text file, entitled "SequenceListing.txt," created on or about Dec. 24, 2019 with a file size of about 9 kb contains the sequence listing for this application and is hereby incorporated by reference in its entirety.

BACKGROUND OF THE INVENTION

1. Field of the Invention

The present invention relates to a method of preparing human intestinal organoids which are similar to an adult intestine through an in vitro maturation process, and intestinal organoids (hIOs) prepared by the method.

2. Description of the Related Art

The mature small intestinal epithelium of adult small intestine should regulate and maintain diverse physiological functions, and structure and homeostasis of intestinal epithelium. Intestinal epithelial cells serve as physical, functional, and immunological barriers, and are formed by 4 types of major specialized cells (enterocytes, Paneth cells, enteroendocrine cells, and goblet cells). The monolayer of intestinal epithelial cells (IEC) plays critical roles in nutrient digestion and absorption, and provides a primary barrier against harmful microorganisms and noxious substances. All types of differentiated cells in the small intestine and the surrounding environment contribute to maturation and maintenance of complex structure and function of the adult small, intestine. However, it is difficult to study development, functions, diseases, and intercellular signaling pathways involved in diverse physiological processes of the mature adult small intestine with high structural and physiological complexity. Further, existing animal models have limitations including a side effect of inter-species variation with the human body, etc. A Caco-2 cell line, which is widely used as an intestinal model for absorption, is a cancer cell line rather than a normal cell, and has a problem in that expression of functional transporters and enzymes is very low, as compared with the human adult intestine. Therefore, there is a need for a technology capable of overcoming the side effects and limitations of existing intestinal models exposed to new drug development and toxicity assessment, and furthermore, providing alternative cellular sources for future use in tissue therapy. This background emphasizes the urgent need to develop in vitro human intestinal models having characteristics of structurally and functionally mature adult small intestine.

Recently, a method of preparing mini organs or organ tissues in vitro have been developed by preparing three-dimensional human intestinal organoids (hIOs) from human pluripotent stem cells (hPSCs) such as human embryonic stem cells (hESCs) and human induced pluripotent stem cells (hiPSCs) using a directed differentiation protocol (Nature 470, 105-109 (2011)). However, despite significant similarities in the structure and function between hIOs thus prepared and a mature human small, intestine control (hSI), hPSCs-derived hIOs still retain characteristics of an immature fetal small intestine in which digestive function, immune function, and expression of intestinal stem cell marker genes such as OLFM4 are insufficient. This may be attributed to the limited time for in vitro maturation and the lack of appropriate signals around the small intestine and/or immunity, blood vessels, and important cell types such as ENS precursor cells, which are important for intestinal maturation. The immature hIOs have a problem that they may further develop into a mature small intestine having adult intestinal structure and functions, only when cultured in vivo after transplantation into the kidney capsule or when grown as a teratoma of mouse.

The present inventors have prepared adult-like mature human intestinal organoids in vitro via defined growth factors and a co-culture system capable of overcoming severe variations in existing experimental procedures for maturation of hIOs having immature fetal characteristics, capable of solving a problem in a maturation method of performing culturing in non-specialized in vivo environments, and capable of providing a human body-like environment. The present inventors first found and completed the finding that such matured intestinal organoids express genes associated with the adult small intestine and have the improved functions. Such a model includes all of in vitro-matured adult intestinal organoids and artificial organs, thereby providing a model which may be used in the fields such as development of human organ mimetic models, absorption models, disease modeling, new drug development, tissue therapy, etc.

SUMMARY OF THE INVENTION

An object of the present invention is to provide a method of preparing in vitro-matured intestinal organoids, the method including the step of culturing immature intestinal organoids in a medium containing T-lymphocytes, cytokines, or a combination thereof.

Another object of the present invention is to provide a composition for maturing immature intestinal organoids in vitro, the composition including T-lymphocytes, cytokines, STAT3 and mTOR signaling activators, or a combination thereof.

Still another object of the present invention is to provide in vitro-matured intestinal organoids, which are prepared by the above method.

Still another object of the present invention is to provide a method of maturing immature intestinal organoids in vitro, the method including the step of culturing immature intestinal organoids in a medium containing T-lymphocytes, cytokines, STAT3 and mTOR signaling activators, or a combination thereof.

Still another object of the present invention is to provide a method of preparing an artificial intestine, the method including the step of preparing intestinal organoids matured according to the above method.

Still another object of the present invention is to provide a tissue therapeutic agent including the in vitro-matured intestinal organoids prepared by the above method.

Still another object of the present invention is to provide a kit for screening of a therapeutic agent for intestine-related diseases, the kit including the matured intestinal organoids prepared by the above method.

BRIEF DESCRIPTION OF THE DRAWINGS

FIG. 1A-FIG. 1G show generation and characterization of hiPSCs lines from wild-type fibroblasts.

FIG. 1A shows a schematic diagram of a reprogramming protocol. Human fibroblasts were reprogrammed into iPSCs using non-integrating episomal vectors.

FIG. 1B shows representative morphology and immunofluorescence analysis of hiPSC #1 derived from CRL2097 and hiPSC #2 derived from IMR90 for the pluripotency markers OCT4, NANOG, TTA-1-60, TRA-1-81, SSEA-3, and SSEA-4. All hiPSC colonies expressed alkaline phosphatase (ALP). Scale bar, 100 μm.

FIG. 1C shows STR profiles of the hiPSC lineages.

FIG. 1D shows the copy number of episomal vectors in hiPSC lineages. The passage number is shown in parentheses. Fibroblasts were analyzed 5 days after electroporation as positive controls.

FIG. 1E shows results of in vitro differentiation of hiPSC lineages, and Immunofluorescence analysis results of endodermal markers FOXA2 and SOX17, mesodermal markers DESMIN and α-smooth muscle actin (α-SMA), and ectodermal markers TUJI and NESTIN. Nuclei were stained with DAPI (blue). Scale bar, 100 μm.

FIG. 1F shows in vivo differentiation via teratoma formation. Histological analysis of teratomas derived from hiPSCs by hematoxylin and eosin staining is shown.

FIG. 1G shows karyotype analysis of hiPSC lineages.

FIG. 2A-FIG. 2C show efficient directed differentiation of hPSCs into immature intestinal organoids.

FIG. 2A shows representative images of successful differentiation of hPSCs into definitive endoderm (DE), hindgut (HG), and hIOs. Scale bar, 200 μm.

FIG. 2B shows results of immunofluorescent staining of DE markers (FOXA2, SOX17) and HG markers (CDX2, KLF5, SOX9). Scale bar, 200 μm.

FIG. 2C shows results of qPCR analysis of intestinal markers in undifferentiated hPSCs (three independent hPSC lineages including H9 hESC, hiPSC #1 derived from CRL2097, and hiPSC #2 derived from IMR90), differentiated hIO (p0, p2), and human small intestine.

FIG. 3A-FIG. 3F show in vitro maturation of hPSC-derived hIOs during co-culture with immune cells.

FIG. 3A shows representative morphology and immunofluorescent staining results for gut-specific markers (SOX?, CDX2, and KLF5), an enterocyte marker (VIL1), a goblet cell marker (MUC2), a Paneth cell marker (LYZ), an enteroendocrine cell marker (CHGA), and an epithelial marker (Ecad). Scale bar, 200 μm.

FIG. 3B shows principal component analysis (PCA) of differentially expressed genes (>2-fold change) in undifferentiated hPSCs, definitive endoderm cells, hindgut cells, and immature hIOs (p0, p2), maturation-induced hIOs by co-culture, and adult human small intestine (hSI).

FIG. 3C shows heatmaps of comparison data of gene expression levels through microarray of stem cell line, endoderm cells, hindgut, hIO p0, hIO p2, hIO p2 co-cultured with Jurkat T, and human small intestine tissue (hSI) in the order of differentiation. Gene expression was more similar to that of the human small intestine tissue, when co-cultured with Jurkat T cells.

FIG. 3D shows gene expression profiles of co-cultured hIOs, and heatmaps of genes known to be involved in defense response, digestive function, and intestinal markers. The co-cultured hIOs were similar to adult human small intestine (hSI).

FIG. 3E shows results of qPCR analysis of intestinal markers and maturation markers in hIO (p2, p8, p10) and hSI.

FIG. 3F shows representative images of morphological changes in hIOs following co-culture with Jurkat. T cells or treatment with Jurkat T cell-conditioned medium (CM). Scale bar, 1 mm. The size of hIOs after two passages; n=9 (control), n=11 (co-culture), n=9 (CM) hIOs per group (**p<0.01, *p<0.05 according to t-test).

FIG. 4A-FIG. 4B show cytokine expression of Jurkat T cells with or without stimulation.

FIG. 4A shows microarray-based heatmap analysis of comparing expression of cytokines (IL-2, IL-8, TNFα, IL-22, IL-6, IL-1β, IL-11, EGF, OSM, and IL-10 in Jurkat T cells according to the presence or absence of stimulation, the kind of culture medium, and the presence or absence of Matrigel.

FIG. 4B shows ELISA analysis for determining concentrations of cytokines (IL-2, IL-8, TNFα, IL-22, IL-6, IL-1β, IL-11, EGF, OSM, and IL-10) in the culture supernatant of Jurkat T cells according to the presence or absence of stimulation, the kind of culture medium, and the presence or absence of Matrigel.

FIG. 5A-FIG. 5C show in vitro maturation of hIOs by co-culture of hIOs with human T lymphocytes.

FIG. 5A shows a schematic illustration of a co-culture system for hIOs and human T lymphocytes. Matrigel-embedded hIOs were applied to transwell plates containing PMA/ionophore-stimulated Jurkat T cells.

FIG. 5B shows representative images of the morphology of control hIOs, hIOs co-cultured with non-stimulated (NS) Jurkat T cells and stimulated Jurkat T cells. Scale bar, 500 μm.

FIG. 5C shows qPCR analysis of the gene expression for intestinal maturation markers in control, co-cultured with NS Jurkat T cells or stimulated Jurkat T cells. Data are presented as mean values of replicates±SEM.

FIG. 6A-FIG. 6E show that IL-2 is a key component in the co-culture system.

FIG. 6A shows a graph of ELISA of IL-2, IL-8, TNFα, IL-22, IL-6, IL-1β, IL-11, EGF, OSM, and IL-10 concentrations in the culture supernatant of Jurkat T cells with or without stimulation.

FIG. 6B shows RT-PCR analysis of IL-2 receptor gene expression in co-cultured or IL-2-treated hIOs.

FIG. 6C shows Western blot analysis of IL-2 receptor expression at a protein level in co-cultured or IL-2-treated hIOs.

FIG. 6D shows phosphorylation status of various proteins involved in the IL-2 signaling pathways in control and co-cultured hIOs, quantified using a human phospho-kinase array kit.

FIG. 6E shows pathway enrichment and a false discovery rate (FDR)<0.001 (left panel) of differentially phosphorylated proteins in the co-cultured hIOs, and a functional interaction (FI) network (right panel) of differentially phosphorylated proteins in the co-cultured hIOs. In the FI network, arrows represent activating/catalyzing actions, solid lines ending in a perpendicular line represent inhibition, solid lines represent complexes or inputs and dashed lines represent predicted FI, and the IL-2-mediated signaling was top-ranked.

FIG. 7A-FIG. 7G show induction of hIO maturation by treatment of hIO with IL-2, as by co-culture.

FIG. 7A shows quantitative assessment of morphological changes of the area and budding structure of hIOs when treated with PMA/ionophore-stimulated Jurkat T conditioned medium (CM) or IL-2 together with IL-2 receptor β antibody (Anti-IL-2Rβ) and IL-2 receptor γc antibody (Anti-IL-2Rγc).

FIG. 7B shows immunofluorescent staining for the proliferation marker (Ki-67), intestinal maturation markers (DEFA5, OLEM4, DPP4 and LCT) in hIOs cultured with conditioned medium (CM) of stimulated Jurkat T cells or IL-2 treatment with IL-2 receptor inactivating antibodies (anti-IL-2Rβ, anti-IL-2Rγc). Scale bar, 50 μm.

FIG. 7C shows phosphorylation status of multiple proteins by treatment with IL-2 in the control and the IL-2-treated hIOs (left panel), quantified by using a human phospho-kinase array kit, and also shows a functional interaction (FE) network (right panel) of differentially phosphorylated proteins in the IL-2-treated hIOs. The mTOR signaling pathway and the STAT3 signaling pathway showed a significant enrichment in the FI network.

FIG. 7D shows Western blotting of phosphorylation status of various proteins involved in the IL-2-mediated signaling pathways in the control and the co-culture or IL-2-treatment.

FIG. 7E shows pathway enrichment of phosphorylated proteins in the L-2-treated hIOs with a false discovery rate (FDR)<0.05.

FIG. 7F shows changes in the size and the budding structure of hIO in the control and treatment with IL-2 and a STAT3 signal inhibitor (S31-201, Stattic) and an mTOR inhibitor (Rapamycin). n=14 hIOs per group (**p<0.01 and *p<0.05 according to t-test).

FIG. 7G shows qPCR analysis of intestinal cell type-specific maturation markers in Cont-hIOs, IL-2 treated Mat-hIOs in the presence or absence of STAT3 inhibitors (Stattic, S31-201), and hSI (hIOs passage 4, n=3 per group). Data are presented as the mean value of replicates □ standard error of the mean (SEM). *p<0.001, p<0.01, and *p<0.05 according to Student's t-test.

FIG. 8A-FIG. 8D show results of human phospho-kinase array to detect activated proteins in hIOs following co-culture with immune cells (A, B) or IL-2 treatment (C, D).

FIGS. 8A and 8C show results of human phospho-kinase array. Each antibody was assessed in duplicate.

FIGS. 8B and 8D show graphs showing fold change of densitometric values with respect to control hIOs.

FIG. 9 shows results of examining changes of human intestinal organoids after treatment with varying concentrations of IL-2, and shows the representative morphology (left panels) of hIOs and the size of hIOs (6, 9, and 12 days at p2; n=10 hIOs per group (right panels)) after treatment with varying concentrations of rhIL-2 (1, 4 and 8 ng/ml) (**p<0.01 and *p<0.05 according to t-test).

FIG. 10A-FIG. 10G show that the co-culture system and IL-2 promote high expression levels of intestinal maturation markers to influence in vitro maturation of hIOs.

FIG. 10A shows quantitative representation of the effects of co-culture or IL-2 on regulation of gene expression from microarray data. Colors represent genes affected by co-culture (n=2) or IL-2 treatment (n=3) (two-fold cut-off). In detail, the majority of the gene expression changes shifted toward the expression patterns of the human small intestine control (hSI) (slashes), and part of the gene expression changes shifted in the opposite direction to hSI expression (dotted). White denotes genes showing similar expression levels between the control hIOs and the co-cultured or IL-2-treated hIOs. The majority of changes showed similar expression patterns to hSI by co-culture and IL-2 treatment.

FIG. 10B shows visualization of functionally grouped annotation networks of selected terms of hSI-specific 3,905 genes using the ClueGO of Cytoscape plug-in. The size of nodes (circles) reflects the statistical significance of the terms. The edges represent association strength between the terms. Respective colors represent GO term groups. Predefined, the group leading term is the most significant term of the group. Gray area represents genes showing significant expression changes similar to hSI after co-culture and IL-2 treatment.

FIG. 10C shows a magnification version of the gene network regulated by co-culture and IL-2 treatment. The number in parentheses represents the number of genes showing similar expression patterns to hSI after IL-2 treatment and co-culture.

FIG. 10D shows a bar graph showing the number of genes associated with the selected 11 GO terms, indicated by purple circles of FIG. 10C.

FIG. 10E-FIG. 10G show changes in gene expression profiles of the co-cultured and IL-2-treated hIO and hSI, and shows heatmaps of genes known to be involved in intestinal markers (FIG. 10E), digestive function (FIG. 10F), and defense response (FIG. 10G).

FIG. 11A-FIG. 11F show that expression of mature small intestine markers was increased in the co-cultured or IL-2-treated hIOs.

FIG. 11A shows qPCR analysis of genes involved in the intestinal maturation in control, co-cultured and IL-2-treated hIOs, human adult tissue-derived intestinal organoids (hAT-IOs) cultured in the presence or absence of nicotinamide, and hSI. Fold changes in expression level were associated with control hIOs.

FIG. 11B-C shows immunofluorescent staining of control, co-cultured and IL-2-treated hIOs with a proliferation marker (Ki-67), an epithelial marker (ECAD) and mature intestinal markers (DEFA5, OLFM4, MUC13, and KRT20), an intestinal enzyme marker (sucrase-isomaltase, SI), and functional transporters (multidrug resistance protein 1, MDR1, peptide transporter 1, PEPT1). Scale bar, 100 μm.

FIG. 11D shows an MDS plot of immature hIO (n=4), co-culture (n=3) or IL-2-treated (n=3) hIO, fetal small intestine tissue (n=6), and adult small intestine tissue (n=6). The adult small intestine tissue and the mature hIO were plotted in the similar area.

FIG. 11E shows a dendrogram based on hierarchical clustering data using a canberra distance and a mcquitty linkage method. Similarity between samples is shown, and longer branch indicates lower similarity between samples. The co-cultured or IL-2-treated hIO samples were similar to adult small intestine tissues (hSI #1~#2) and distal adult small intestine tissues (his Dist. #1~#4).

FIG. 11F shows a heatmap between samples, which was generated based on Spearman's correlation. Red indicates the highest level of similarity between samples, and blue indicates the lowest level of similarity. The hIO samples that underwent the maturation process showed a high level of similarity to the adult small intestine tissue sample.

FIG. 12A-FIG. 12J show that in vitro-matured hIOs have significantly enhanced expression of intestinal enzymes and transporters, and functionalities.

FIG. 12A shows comparison of the gene expression of drug-metabolizing enzymes (phase I/II enzymes and intestinal transporters (ABC transporters and SLC transporters). The graph represents the number of the upregulated genes with expression >2-fold when compared with the control hIOs.

FIG. 12B shows hierarchical clustering of representative genes encoding intestinal enzymes and transporters found in control, co-cultured, and IL-2-treated hIOs, hAT-IOs, and hSI.

FIG. 12C shows paracellular permeability of hIOs incubated with 4 kDa FITC-Dextran (left panel) and 40 kDa FITC-Dextran (right panel).

FIG. 12D shows relative expression of P-gp (MDR1, ABCB1), and changes in the expression levels were increased in the similar pattern to hSI, as compared with the control hIO.

FIG. 12E shows concentrations of paclitaxel (n=20 per group) in the absence or presence of verapamil in hIOs (***p<0.001 according to t<test).

FIG. 12F shows glucose-stimulated intracellular calcium ion release in real-time manner in control, and co-cultured or IL-2 treated hIOs by using a Fluo-4-AM calcium fluorescent indicator (upper panels), and mean values of peak fluorescence intensity after glucose stimulation (ROI=15 per group, ***p<0.001 according to t<test).

FIG. 12G shows a graph of the morphological changes (upper panel) and the size of hIOs (lower panel) upon forskolin induced swelling (FIS) by treatment of control and co-cultured and IL-2-treated hIOs with forskolin and CFTR inhibitors (CETR$_{inh}$172, GlyH101 for 120 minutes to identify CFTR (Cystic fibrosis transmembrane conductance regulator) function (n=4 per group).

FIG. 12H shows PAS/Mucicarmine staining for mucin to identify the function of goblet cells in control and co-cultured or IL-2-treated hIOs.

FIG. 12I shows gene expression patterns of gastric inhibitory polypeptide (GIP), which is one of hormone s produced by entero-endocrine cells, in hIOs under different conditions.

FIG. 12J shows ELISA showing the release of GIP hormone into the culture supernatants of hIOs under different conditions.

FIG. 13A-FIG. 13E show that in vitro maturation of hIOs promotes neovascularization of host vasculature in vivo.

FIG. 13A shows ex vive fluorescence images of the kidney with DiR-labeled hIOs 1 week after transplantation using an IVIS imaging system (left panels), and shows a graph of the fluorescence intensity, expressed as the average radiance of the DiR-labeled hIOs (n=3) (right panels) (*p<0.05 and *p<0.01 according to t-test).

FIG. 13B shows results of H & E staining of hIOs 1 week after transplantation into the kidney capsule of immunodeficient (NSG) mice.

FIG. 13C shows that the intestinal maturation markers (DEFA5, OLFM4, MUC13 and KRT20) were consistently expressed in co-cultured and IL-2-treated hIOs after transplantation.

FIG. 13D shows that the intestinal enzyme (sucrase-isomaltase, SIM) and functional transporters (multidrug resistance protein 1, MDR1, peptide transporter 1, PEPT1) were detected in co-cultured and IL-2-treated hIOs after transplantation.

FIG. 13E shows results of immunofluorescent staining of the engrafted hIOs for human vasculature containing vascular endothelial cells with hCD31 and laminated smooth muscle with α-SMA (upper panels). Co-staining for α-SMA and hCD31 shows that the endothelial cells were derived from the mesenchyme adjacent to hIOs.

Further, FIG. 13E shows immunofluorescent staining images of VEGF (middle panels) and immunofluorescent staining images of blood vessels derived from the co-cultured and IL-2-treated hIOs (hCD31-positive) connected to the host vasculature (mouse-specific mMECA-32-positive) within 1 week after transplantation (bottom panels, white arrowheads). Cell nuclei (blue) were stained with DAPI. Antibodies capable of selectively detecting only human proteins were used. Scale bar, 100 µm. Similar results were obtained in three independent experiments, and representative images are shown.

FIG. 14A-FIG. 14B show transplantation results of in vitro-matured hIOs.

FIG. 14A shows results of in vivo fluorescence imaging at 1 day post-transplantation of DiR-labeled hIOs into the kidney capsule of immunodeficient NSG mice. Average radiance of mice transplanted with DiR-labeled hIOs (n=3) is shown.

FIG. 14B shows that four intestinal lineages including enterocytes (VIL), goblet cells (MUC2), enteroendocrine cells (CHGA), and Paneth cells (LYSO) were present in the transplanted hIOs. E-cadherin (ECAD) was used for intestinal epithelium staining. Scale bar, 50 µm.

FIG. 15A-FIG. 15B show results of connecting the in vitro-matured hIOs-derived vessels to the mouse vasculature.

FIG. 15A shows results of immunofluorescent staining of human-specific endothelial cells CD31 (hCD31 for human vascular endothelial cells) in hIOs before in vivo transplantation. Scale bar, 100 µm. Differentiation into vascular endothelial cells was not found in the in vitro-matured hIOs.

FIG. 15B shows intensity profiles of hCD31 and mMECA-32 fluorescence along yellow line in the merged image.

FIG. 16 shows karyotype analysis of the in vitro-matured hIOs.

FIG. 17A-FIG. 17C show in vitro maturation of hIOs by a STAT3 activator, colivelin.

FIG. 17A shows comparison of the morphological changes and the size of surface area of hIOs with varying concentrations of colivelin. Scale bar, 500 µm.

FIG. 17B shows qPCR results of examining increased expression of intestinal maturation marker genes. Overall expression was increased, as compared with control hIOs.

FIG. 17C shows immunofluorescent staining for the proliferation marker (Ki-67), epithelium marker (ECAD), and intestinal maturation markers (OLFM4, MUC13 and KRT20) in control and colivelin-treated hIOs. Scale bar, 50 µm.

FIG. 18A-FIG. 18B is effect of STAT3 signaling on the growth of hIOs.

FIG. 18A is response of hIOs to varying concentrations of Colivelin (CLN). Representative images of the morphologies of hIOs after treatment with the indicated concentrations of CLN (0.01, 1 and 100 nM; left panels). Quantitative assessment of the size of hIOs (14 days at p3); n=6 hIOs per group (right panels).

FIG. 18B is representative images of morphologies of hIOs after treatment of IL-22 (1 and 10 ng/ml; left panels). Quantitative assessment of the size of hIOs (14 days at p1); n=18 hIOs per group (right panels). Scale bar, 1 mm. Data are presented as mean values of replicates±SEM. **p<0.01 and *p<0.05 according to t-test.

FIG. 19 is in vitro maturation of hPSC-derived hIOs which is accompanied by the activation of STAT3 signaling. Representative morphologies and immunofluorescence staining with p-STAT3 (Y705) and ECAD in Cont-hIOs, and IL-2 treated Mat-hIOs in the presence or absence of STAT3 inhibitors, including Stattic (1 □M) or S31-201 (10 □M). Black scale bar, 200 □m. White scale bar, 50 m.

FIG. 20A-FIG. 20H is generation and characterization of the STAT3 KO hESC line using CRISPR-Cas9 genome editing.

FIG. 20A is schematic representation of STAT3 gene structure and the mutant genotype of STAT3 KO hESC lines. Exons of STAT3 are shown by black rectangles, and targeting sequences are indicated at the bottom of the STAT3 gene structure. The nucleotide sequences of sgRNA are underlined, the PAM (NGG) sequences are represented in green letters, and the insertion and deletion mutations in the STAT3 gene are represented by red letters and dashes.

FIG. 20B is T7 endonuclease 1 (T7E1) assay for mutation verification of STAT3 KO hESC lines. Genomic PCR products from each clone and heteroduplex of the control and individual clones were digested by T7E1.

FIG. 20C is Western blot analysis of STAT3 in WT and STAT3 KO hESC lines.

FIG. 20D is qPCR analysis of pluripotency markers in undifferentiated H9, WT, and STAT3 KO hESC lines. Data are presented as the mean value of replicates ☐ SEM. (after two passages of maturation, n=3 per group).

FIG. 20E is immunofluorescence analysis for the pluripotency markers OCT4, NANOG, TRA-1-60, TRA-1-81, SSEA-3, and SSEA-4. Scale bar, 200 μm.

FIG. 20F is schematic representation of hPSC differentiation into hIOs and in vitro maturation of hIOs.

FIG. 20G is representative morphologies during the differentiation process from hESCs to definitive endoderm (DE), hindgut (HG), and hIOs. Scale bar, 200 μm.

FIG. 20H is immunofluorescence analysis for intestine-specific markers (SOX9, CDX2, and KLF5); the enterocyte marker, villin 1 (VL); the enteroendocrine cell marker, chromogranin A (CHGA), the goblet cell marker, mucin 2 (MUC2); the Paneth cell marker, lysozyme (LYZ); and the epithelial marker, ECAD. Scale bars, 200 μm.

FIG. 21A-FIG. 21D is in vitro maturation of STAT3 KO hIOs.

FIG. 21A is representative images of morphological changes during in vitro maturation of hIOs by co-culture with PMA/ionophore-stimulated Jurkat T or treatment with IL-2. Scale bar, 500 μm.

FIG. 21B is quantitative assessment of the surface area of hIOs (left panel, after two passages of maturation, n=5 per group) and the number of budding structures per single hIO (right panel, after two passages of maturation, n=5 per group). Data are presented as the mean value of replicates±SEM. *$p<0.001$, $p<0.01$, and *$p<0.05$ according to Kruskal-Wallis test.

FIG. 21C is immunofluorescence staining of WT hIOs and STAT3 KO hIOs with an epithelial marker (ECAD) and mature intestinal markers (DEFA5, OLEM4, DPPIV, and LCT) following in vitro maturation. Scale bar, 50 μm.

FIG. 21D is qPCR analysis of intestinal maturation markers in WT Mat-hIOs and STAT3 KO Mat-hIOs by treatment with IL-2 (after three passages of maturation, n=4 per group) Data are presented as the mean value of replicates±SEM. *$p<0.001$, $p<0.01$, and *$p<0.05$.

DETAILED DESCRIPTION OF THE PREFERRED EMBODIMENTS

In order to achieve the above objects, an aspect of the present invention provides a method of preparing in vitro-matured intestinal organoids, the method including the step of culturing immature intestinal organoids in a medium containing T-lymphocytes, cytokines, STAT3 and mTOR signaling activators, or a combination thereof.

As used herein, the term "organoid" refers to a cell mass having a three dimensional structure, and refers to a miniaturized and simplified version of an organ which is not collected or obtained from an animal, etc., but is prepared through an artificial culture process. The origin of cells which constitute the organoid is not limited. Organoids may be derived from tissues, embryonic stem cells, or induced pluripotent stem cells, and may be cultured in a three dimension due to their self-renewal and differentiation capacity. The organoid may have an environment that is allowed to interact with the surrounding environment during cell growth. Accordingly, the 3D organoid in the present invention almost completely mimics organs that actually interact in vivo, thereby being an excellent model for developing therapeutic agents for diseases.

As used herein, the term "intestinal organoid (human intestinal organoids; hIO)" refers to an organoid that includes crypt cells, a villus-like structure, and four major specialized cells (enterocytes, Paneth cells, enteroendocrine cells, and goblet cells), and reproduces diversity and structure of small intestine epithelial cells. Further, hIO includes a primitive mesenchyme which may differentiate into smooth muscles, myofibroblasts, and fibroblasts which are generally found in the submucosal layers of the human adult small intestine (hSI), and hIOs may exert basic physiological functions of hSI, such as secretion of mucus and absorption of amino acids.

As used herein, the term "immature intestinal organoid (immature hIO)" refers to an intestinal organoid which does not express various genes required for digestive function, transporter system, immune function, and host defense, which are characteristics of a mature intestinal organoid (mature hIO), and does not express mature intestinal stem cell markers, while reproducing diversity and structure of small intestine epithelial cells which are characteristics of an intestinal organoid, including a primitive mesenchyme which may differentiate into smooth muscles, myofibroblasts, and fibroblasts which are generally found in the submucosal layers, and exerting basic physiological functions of hSI, such as secretion of mucus and absorption of amino acids.

Further, the immature intestinal organoid is an intestinal organoid that does not yet mature to an adult small intestine, and is in a state similar to the fetal, small intestine. In the present invention, the 'immature' may be used interchangeably with 'in a state similar to the fetal small intestine'. In addition, the immature intestinal organoid is not limited, unless it has the characteristics of a mature intestinal organoid, and the immature intestinal organoid includes intestinal organoids differentiated from human pluripotent stem cells according to existing known methods.

In a specific aspect, provided is a method of preparing in vitro-matured intestinal organoids, the method further including the step of culturing stem cells or hindgut spheroids differentiated from stem cells in an intestinal organoid medium to prepare the immature intestinal organoids.

As used herein, the term "intestinal organoid medium" refers to a medium in which stem cells may be cultured into an intestinal organoid. The intestinal organoid medium may include any one without limitation, either those purchased from a commercially available source or those prepared, as long as it is able to culture stem cells into the intestinal organoid.

For example, for induction of stem cells into a definitive endoderm, the stem cells are cultured in an RPMI 1640 medium, and then for differentiation into a hindgut spheroid, FGF4 (R&D Systems) and WNT3A (R&D Systems) are incubated in an RPMI 1640 medium supplemented with FBS. Thereafter, the spheroid may be cultured in DMEM/F12 medium containing 1×B27 (Invitrogen), R-Spondin 1 (R&D Systems), EGF (R&D Systems), and Noggin (R&D Systems), but is not limited thereto.

As used herein, the term "STAT3 and mTOR signaling activators" refers to substances that activate the STAT3 and mTOR signaling pathways. With respect to the objects of the present invention, the STAT3 and mTOR signaling activators are not limited, as long as they activate the STAT3 and mTOR signaling pathways of the immature intestinal organoid to mature the immature intestinal organoid. Specifically, the STAT3 and mTOR signaling activators may be colivelin, but is not limited thereto.

In a specific aspect, provided is a method of preparing in vitro-matured intestinal organoids, wherein the STAT3 and mTOR signaling activators are one or more phosphorylation activators selected from the group consisting of STAT3, AKT, and P70 S6 kinase.

In a specific embodiment of the present invention, it was confirmed that when an activated STAT3 or mTOR signaling inhibitor is used in hIOs co-cultured with T lymphocytes and hIOs treated with IL-2, in vitro maturation by IL-2 did not occur (FIG. 7E), and in particular, when colivelin capable of activating the STAT3 signaling pathway similar to in vitro hIO maturation by IL-2 is treated, in vitro-matured hIOs may be prepared (FIGS. 17A to 17C).

Existing methods of preparing immature intestinal organoids include differentiating and/or culturing by a general known method without using a medium containing T-lymphocytes, cytokines, or STAT3 and mTOR signaling activators, or a combination thereof. With respect to the objects of the present invention, the method of preparing mature intestinal organoids may prepare the mature intestinal organoids having adult intestinal characteristics in vitro, by culturing immature intestinal organoids using the medium containing T-lymphocytes, cytokines, or STAT3 and mTOR signaling activators, or a combination thereof.

Further, in a specific aspect, provided is a method of preparing in vitro-matured intestinal organoids, the method further including the step of differentiating stem cells into immature intestinal organoids.

In the present invention, the stem cells may be embryonic stem cells or induced pluripotent stem cells (iPSC), but are not limited thereto.

As used herein, the term "induced pluripotent stem cells (iPSCs)" refer to cells which are induced to have pluripotency from differentiated cells through artificial reprogramming processes.

In a specific embodiment of the present invention, a known method is used to prepare induced pluripotent stem cells (iPSCs) from fibroblasts, and then immature intestinal organoids (hIOs) are generated from hPSCs using a hIO differentiation protocol (Example 1). Specifically, expression of intestinal transcription factor-related markers was examined to confirm successful differentiation of fibroblasts into immature intestinal organoids.

As used herein, the term "reprogramming" refers to a process of restoring or converting differentiated cells that exist in different status, such as cells having no differentiation potency or cells having partial differentiation potency, into final cells having a new type of differentiation potency. In the present invention, the reprogramming may be used in the same sense as dedifferentiation. Such a reprogramming mechanism of cells means establishing a different set of epigenetic markers after epigenetic (a DNA state associated with causing a genetic change in function without a change in a nucleotide sequence) markers in the nucleus are deleted. While multicellular organisms differentiate and grow, different cells and tissues acquire different gene expression programs.

The reprogramming may be performed using a method known in the art without limitation, as long as it is able to produce induced pluripotent stem cells from differentiated cells.

Specifically, in the present invention, the artificial reprogramming process may be performed by using a virus-mediated method using a non-integrating virus or by using a non-integrating non-viral vector or by introducing a non-viral-mediated reprogramming factor using a protein and a cell extract, or may include a reprogramming process by a stem cell extract, a compound, etc. The induced pluripotent stem cells have almost the same characteristics as embryonic stem cells. Specifically, the induced pluripotent stem cells show the same cell morphology, have similar gene and protein expression patterns, have pluripotency in vitro and in vivo, and form teratoma. In particular, induced pluripotent stem cells of a mouse may form chimera mice when inserted into the blastocyst of the mouse, and enable germline transmission of genes. The induced pluripotent stem cells of the present invention may be derived from humans, monkeys, pigs, horses, cows, sheep, dogs, cats, mice, or rabbits, and specifically, humans.

As used herein, the term "reprogramming factor" refers to a substance that induces reprogramming of finally differentiated cells into a new type of pluripotent stem cells with the differentiation potential. The reprogramming factor may include any reprogramming factor without limitation, as long as it is a substance that induces reprogramming of finally differentiated cells. The reprogramming factor may be selected according to the type of cells to be differentiated. Specifically, the reprogramming factor may be one or more proteins selected from the group consisting of Oct4, Sox2, Klf4, c-Myc, Nanog, Lin-28, and Rex1, or a nucleic acid molecule encoding the protein, but is not limited thereto.

The term "differentiated cells" may be, but are not particularly limited to, cells of which lineage is already specified, such as germ cells, somatic cells, or progenitor cells. Examples thereof may be cells derived from humans, but cells derived from various individuals are also within the scope of the present invention.

Further, the differentiated cells of the present invention may include cells differentiated in vivo or ex vivo, and specifically, may be differentiated cells separated from a living body.

The "somatic cell" refers to all cells that have completed differentiation to constitute an animal or a plant, excluding germ cells, and the "progenitor cell" refers to a parent cell expressing no differentiation trait but having a differentiation fate, when a cell corresponding to a progeny is revealed to express a specific differentiation trait. For example, with regard to nerve cells (neurons), neuroblasts (neural stem cells) correspond to progenitor cells, and with regard to myotubes, myoblasts correspond to progenitor cells. With respect to the objects of the present invention, differentiated cells used in the process of preparing the intestinal organoids of the present invention may be specifically human-derived fibroblasts, and specifically, the human-derived fibroblast may be CRL-2097 cell line or IMR90, but is not limited thereto.

As used herein, the term "differentiation" refers to a phenomenon in which the structure or function of cells is specialized during the division, proliferation and growth thereof, that is, the morphology and function of cell or tissue of an organism change in order to perform work given to the cell or tissue. For example, it may include a process whereby pluripotent stem cells such as embryonic stem cells turn into ectodermal, mesodermal, and endodermal cells as well as a process whereby hematopoietic stem cells turn into red blood cells, white blood cells, platelets, etc., i.e., a phenomenon in which progenitor cells express specific differentiation traits.

As used herein, the term "T-lymphocyte" refers to one of lymphocytes that play a central role in cell-mediated immunity, and is also called T-cell. T cells are distinguished from other lymphocytes such as B cells and natural killer cells by the presence of T cell receptors on the cell surface. In the present invention, the T-lymphocytes mean those to be used in co-culture to mimic the in vivo intestinal environment, and any one may be included without limitation, as long as it may be used in co-culture to mimic the in vivo intestinal environment. In addition, the T-lymphocyte of the present invention may include all T-lymphocytes derived from humans, monkeys, pigs, horses, cows, sheep, dogs, cats, mice, rabbits, etc. The T-lymphocytes may be specifically human-derived T-lymphocytes, and more specifically, Jurkat T cells, but are not limited thereto.

In a specific embodiment of the present invention, when hIOs and Jurkat T cells were co-cultured to mimic the in vivo intestinal environment (FIG. 5), the size of immature intestinal organoids was remarkably increased (FIG. 3F), and they were similar to mature intestinal organoids through expression of intestinal maturation-related markers (FIGS. 3B, 3C, and 3D). These results suggest that hPSC-derived immature intestinal organoids (hIOs) become similar to a mature human small intestine (hSI) control, when co-cultured with Jurkat T cells used in the present invention.

As used herein, the term "cytokine" refers to a protein that plays an important role in cell signaling. The release of cytokine affects the behavior of cells around the cytokine. Specifically, cytokine is an immunomodulator that is involved in autocrine signaling, paracrine signaling and endocrine signaling. In addition, cytokine is produced by a wide range of cells, including endothelial cells, fibroblasts, and various stromal cells, as well as immune cells such as macrophages, B lymphocytes, T lymphocytes and mast cells. Cytokines regulate the balance between humoral and cell-based immune responses and regulate maturation, growth, and response of specific cell populations.

In the present invention, cytokine may be used in co-culture to mimic the in vive intestinal environment, or may be used to prepare the more similar in vivo intestinal environment by treating only the cytokine secreted by T-lymphocyte co-culture. With respect to the objects of the present invention, major cytokines secreted by T-lymphocytes may be one or more selected from the group consisting of IL-2 (interleukin-2), IL-8 (interleukin-8), TNFα (Tumor Necrosis Factor-α), IL-22 (interleukin-22), IL-6 (interleukin-6), IL-β (interleukin-1β), IL-11 (interleukin-11), EGF (epidermal growth factor), OSM (oncostatin M), and IL-10 (interleukin-10), and more specifically IL-2, but are not limited thereto.

In a specific embodiment of the present invention, when immature intestinal organoids (hIOs) were treated with IL-2 to mimic the in vivo intestinal environment (FIGS. 7A and 9), the size of the organoids was remarkably increased (FIGS. 7A and 9), and they were similar to mature intestinal organoids through expression of intestinal maturation-related markers (FIGS. 10E, 10F, and 10G). These results suggest that hPSC-derived intestinal organoids become similar to hSI, when treated with IL-2 used in the present invention.

Further, in a specific embodiment, a phospho-kinase array of the intestinal organoids co-cultured with T lymphocytes was performed to confirm phosphorylation of proteins involved in the IL-2-mediated signaling pathway, such as STAT3, c-Jun, p38α, and ERK1/2 (FIGS. 3A and 8B), and thus it was confirmed that the IL-2-mediated signaling pathway is one of the most heavily upregulated pathways in the co-cultured hIOs (FIGS. 6C and 6E), indicating that cytokines are one of the important factors in the co-culture system and play a key role in the in vitro maturation of intestinal organoids.

Furthermore, to examine that IL-2 is a key factor in the in vitro maturation of human intestinal organoids (hIOs) differentiated from hPSCs in the co-culture effect for the in vitro maturation, IL-2 was treated and then phosphorylation levels were measured by a phospho-kinase array analysis (FIGS. 8C and 8D). As a result, STAT3 (Y705) showed 3.3-fold increase, as compared with the control, and increased phosphorylation of AKT and P70 S6 kinase in the STAT3 and mTOR signaling pathway was confirmed (FIGS. 7C, 7D, and 7E).

Further, in a specific embodiment, to examine that the IL-2-mediated signaling pathway is involved in the in vitro maturation of hIOs as well as plays a role in promoting growth of hIOs, gene expression profiling was performed. As a result, when co-cultured with human T lymphocytes or treated with IL-2, gene expression profiles of hIOs shifted toward the profile of hSI (FIG. 10A). Further, to more easily understand the biological meaning of the differentially expressed genes (DEGs) with regard to intestinal maturation, a functional enrichment analysis was performed using ClueGO-in plug of Cytoscape. As a result, among the differentially expressed genes between mature hSIs and control hIOs, genes associated with key biological processes, including cell-cell adhesion, defense response, innate immune response, regulation of immune system process, positive regulation of response to stimulus, cell surface receptor signaling pathway, cellular response to chemical stimulus, signal transduction, signal transduction, cell communication, and response to cytokine, were significantly ($p<0.05$) expressed in the co-culture system or the IL-2 treatment (highlighted in gray) (FIG. 10B), similar to expression patterns in hSI (nodes highlighted in red) (FIG. 10C).

In a specific embodiment of the present invention, it was confirmed that when an activated STAT3 or mTOR signaling inhibitor is used in hTOs co-cultured with T lymphocytes and hIOs treated with IL-2, in vitro maturation by IL-2 did not occur (FIG. 7E), and in particular, when colivelin capable of activating the STAT3 signaling pathway similar to in vitro hIO maturation by IL-2 is treated, in vitro-matured hIOs may be prepared (FIGS. 17A, 17C, and 18A). Although another known STAT3 activator IL-22 is treated, in vitro-matured hIOs may be prepared (FIG. 18B).

In contrast, when STAT3 inhibitors, Stattic and S3I-201, were treated, in vitro-matured hIOs may not be formed (FIGS. 7G and 19).

In a specific embodiment of the present invention, a CRISPR-cas9 technology was used to prepare a STAT3 knockout HESC line, followed by characterization (FIGS. 20A to 20H). hIOs differentiated therefrom did not mature (FIGS. 21A, 218, 21C, and 21D), indicating that STAT3 KO seriously impair the in vitro maturation of hIO epithelium regardless of cell survival.

As used herein, the term "mature intestinal organoid (mature hIO)" is a term opposite to the immature intestinal organoid, and refers to an intestinal organoid having expression of genes necessary for digestive function, transport system, immune function, and host defense which are possessed by adult small intestine. Specifically, the mature small intestine has unique characteristics including enhanced expression of small intestine stem cell marker genes, and genes necessary for digestive function, transport system, extensive immune function, and host defense. In particular, proper expression and activity of transporters involved in physiological and pharmacokinetic roles are prerequisites for normal small intestine functions such as drug absorption, distribution, and excretion. Therefore, appropriate in vitro intestinal models are a powerful and alternative tool for modeling human intestinal diseases by reproducing physiological functions and mimicking the structure, and serve as a screening platform for preclinical drug discovery. In the present invention, 'mature' may be also used interchangeably with 'similar state to adult small intestine' or 'hSI'.

In a specific embodiment of the present invention, hIOs co-cultured with T lymphocytes and hIOs treated with IL-2 showed increased expression of CDX2, OLM44 (small intestine stem cell marker gene), DPP4, LCT (digestive function-related gene), SLC5A1 (transporter system-related gene), LYZ, DEFA5, DEFA6, (immune function and host defense function-related gene), and other intestinal maturation-related gene genes KRT20, MUC13, CREB3L3, in the similar pattern to those of mature human small intestine control (hSI) (FIGS. 10A to 10G), and thus it was confirmed that in vitro-matured hIOs may be prepared.

In a specific embodiment of the present invention, hIOs co-cultured with T lymphocytes and hIOs treated with IL-2 showed the increased expression of genes involved in functions, and metabolism and transporter system of the mature adult intestine, in the similar pattern to those of mature human small intestine control (hSI) (FIGS. 11A and 11B), and in particular, increased expression of P-gp (P-glycoprotein/MDR1/ABCB1) related to drug absorption and increased activity were also confirmed by a paclitaxel assay (FIGS. 11C and 11D), and thus it was confirmed that in vitro-matured hIOs may be prepared. These results indicate that the present invention enables a drug absorption test in the environment more similar to the human body.

The preparation method of the present invention may be performed by 1) co-culturing immature intestinal organoids with T-lymphocytes, 2) treating immature intestinal organoids with cytokines, 3) treating immature intestinal organoids with STAT3 and mTOR signaling activators, or 4) performing 1), 2) and 3) simultaneously or sequentially.

The mature intestinal organoids prepared by the present invention may have increased expression of one or more markers of the following (a) to (f), as compared with the immature intestinal organoids: (a) intestinal maturation-related intestinal stem cell markers, CDX2 and OLFM4 (Olfactomedin-4); (b) digestive function-related markers, DPP4 (Dipeptidyl peptidase-4) and LCT (lactase); (c) immune function and host defense function-related markers, DEFA5 (human-defensins 5), DEFA6 (human-defensins 56), and LYZ (lysozyme); (d) transporter system-related markers, SLC5A1 (solute carrier family 5 member 1), P-glycoprotein 1 (p-gp, multidrug resistance protein 1 (MDR1), and ATP-binding cassette sub-family B member 1 (ABCB1)); (e) mature intestinal differentiation markers, KRT20 (Keratin 20), MUC13 (Mucin 13), and CREB3L3 (Cyclic AMP-responsive element-binding protein 3); and (f) STAT3 and mTOR signaling markers, phosphorylated STAT3 (signal transducer and activator of transcription 3), phosphorylated AKT (protein kinase B (PKB)), and phosphorylated P70S6 kinase (Ribosomal protein S6 kinase beta-1 (S6K1)), but are not limited thereto. All the genes associated with defense response, intestinal markers, and digestive function as in FIG. 3C of the present invention, and the genes associated with intestinal metabolic enzymes and transporters as in FIG. 11B may also be included.

As used herein, the term "intestinal maturation" refers to acquisition of genomic expression and functional characteristics of adult intestine. Specifically, the intestinal maturation means maturation of intestinal organoids in which four types of intestinal cells have high morphological similarity, and gene and protein expressions of intestinal maturation markers, intestinal stem cell markers, digestive function-associated markers, immune function and host defense function-associated markers, transport system and metabolic enzyme-associated markers, or mature intestinal differentiation markers are increased, and the similarity to the in vivo actual intestine is high to mimic actual functions such as nutrient and drug absorption function, mucus secretion, and hormone secretion.

In a specific embodiment, hIOs co-cultured with T lymphocytes and hIOs treated with IL-2 showed increased activity of P-gp which is an efflux pump transporter present in mature adult small intestine epithelial cells, and glucose responsiveness as a nutrient absorption function of small intestine epithelial cells was examined by a Fluo4-AM analysis. Further, CFTR (Cystic fibrosis transmembrane conductance regulator) function was examined by a forskolin-induced swelling assay, and mucous produced by mature goblet cells and GIP hormone produced by mature enteroendocrine cells were examined. As a result, it was confirmed that all functions of in vivo intestinal differentiated cells were reproduced in hIOs, indicating in vitro maturation of hIOs.

Further, the intestinal maturation means activation of the STAT3 and mTOR signaling pathway markers, STAT3 (signal transducer and activator of transcription 3), AKT (protein kinase B (PKB)), and P70S6 kinase (Ribosomal protein S6 kinase beta-1 (S6K1)) in hIOs. In the embodiments, it was confirmed that treatment with an inhibitor of the STAT3 and mTOR signaling pathway inhibited hIO maturation, and on the contrary, treatment with another activator of STAT3 promoted hIO maturation.

As used herein, the term "intestinal differentiation" means having a crypt and villi structure which is a unique morphological characteristic of the intestine and presence of four major specialized cells (enterocytes, Paneth cells, enteroendocrine cells, and goblet cells).

In a specific embodiment of the present invention, to examine whether the intestinal organoids prepared by the method of preparing the in vitro-matured intestinal organoids of the present invention have characteristics of not immature intestinal organoids having fetal-like characteristics but intestinal organoids having adult-like characteristics, a microarray analysis and qPCR were performed. As a result, expression levels of an intestine-specific marker (CDX2), a mature intestine stem cell marker (OLFM4), and human α-defensin (DEFA5 and DEFA6) and lysozyme (LYZ) which are specific to Paneth cells produced in mature intestine, digestive function-related enzymes DPP4 and LCT were upregulated in the co-cultured or IL-2-treated hIOs. It was also confirmed that differentiation markers of the mature intestine including KRT20, MUC13, SLC5A1, and CREB3L3 were upregulated in the co-cultured or IL-2-treated hIOs (FIG. 11A) Constituently, qPCR data confirmed that protein expression levels of DEFA5, OLFM4, MUC13, KRT20, SI, PEPT1, and MDR1 were not detected in the control, but were detected in the co-cultured or IL-2-treated hIOs (FIGS. 11B and 11C). Accordingly, it was confirmed that the co-culture system or the IL-2 treatment enables induction of in vitro maturation of hPSC-derived hIOs having fetal-like characteristics into hIOs having adult intestinal characteristics.

The in vitro-matured intestinal organoids prepared by the method of preparing the in vitro-matured intestinal organoids of the present invention may express activated STAT3 and mTOR signaling pathway-related specific markers. In particular, expression of STAT3, AKT or P70 S6 kinase and phosphorylation thereof were promoted.

In a specific embodiment of the present invention, to confirm that IL-2 is a potential key factor in the effect of co-culture on the in vitro maturation of hIOs, IL-2 treatment was performed, and then a phospho-kinase array analysis was performed to measure the phosphorylation levels (FIG. 7C), followed by Western blotting (FIG. 7D). As a result, STAT3 (Y705) showed 3.3-fold increase, as compared with the control, and increased phosphorylation of AKT and P70S6 kinase in the STAT3 and mTOR signaling pathway was confirmed.

In the present invention, induced pluripotent stem cells are differentiated into three-dimensional mature intestinal organoids (hIOs), and cultured, thereby overcoming the physiological and evolutionary differences of human, which is the limitation of existing animal models, and may be used to elucidate the enterocyte formation process and complex pathological process that occur upon using a 2D cell culture system. In addition, unlike the existing immature hIOs, they have complexity more similar to the human intestine in terms of morphology, and it is easy to confirm the expression of genes and proteins expressed in the intestinal tract of a mature adult by qPCR and immunostaining, and to confirm the acquisition of functionality. Therefore, since the in vitro-matured intestinal organoid (hIO) model may reproduce the physiological functionality of human and may mimic the structure thereof, it may be applied in studying the full development processes from embryo to adult, and it may precisely reproduce the in vivo-like environment as an intestinal disease-related model.

Another aspect of the present invention provides in vitro-matured intestinal organoids (hIO) prepared by the above preparation method.

The 'matured intestinal organoids' are the same as described above.

Since hIOs prepared in the present invention may be prepared using iPSCs from a healthy control and an intestinal disease patient, the in vitro-matured hIOs may be a human intestinal organoid to understand the physiology and pathophysiology of the human intestine in a patient-specific manner. In general, production of functional mature cells from hPSCs is technically difficult, and ultimately, immature organoids are produced. In vivo maturation after transplantation of immature intestinal organoids appears to promote the induction of functional mature cells, but use of these cells in a proliferative progenitor state may cause additional risks for practical application and clinical translation. Therefore, in order to reproduce the physiological functions of mature adult cells, in vitro-matured models of hPSC-derived cells and organoids are required.

Since the matured intestinal organoids according to the present invention have a composition close to the human intestine, they may be used as an alternative to intestinal disease-related models in need of an alternative model for animal experiments worldwide.

Still another aspect of the present invention provides a composition for maturing immature intestinal organoids in vitro, the composition including T-lymphocytes, cytokines, STAT3 and mTOR signaling activators, or a combination thereof.

Still another aspect of the present invention provides a method of maturing immature intestinal organoids in vitro, the method including the step of culturing immature intestinal organoids in a medium containing T-lymphocytes, cytokines, STAT3 and mTOR signaling activators, or a combination thereof.

The 'T-lymphocytes', 'cytokines', 'organoids', 'immature intestinal organoids' and 'matured intestinal organoids' are the same as described above.

Still another aspect of the present invention provides a method of preparing an artificial intestine, the method including the step of preparing intestinal organoids matured according to the above method.

The 'organoids' and 'matured intestinal organoids' are the same as described above.

As used herein, the term "artificial intestine" is an artificial intestine prepared from cells and tissues through isolation from an individual, culture, and special manipulation, which are used as a substitute for a body organ for the purpose of treatment, and the artificial intestine is prepared based on biotechnology in order to restore the cell or tissue functions, and is used for the purpose of treatment.

The matured intestinal organoids prepared by the preparation method of the present invention are advantageous in that mature intestinal organoids having adult-like characteristics are differentiated even in vitro, as described above, and in vivo culture using animals is not needed, unlike the existing method of preparing intestinal organoids. The matured intestinal organoids may form an appropriate link (network) with the surrounding cells, after transplanted into a patient. Most of all, since patient's own adult cells are used, there are no technical problems such as immunogenicity, etc., or no ethical problems, which impede the future use for tissue therapy.

In a specific embodiment of the present invention, to assess the suitability of in vitro-matured hIOs for transplantation by co-culture with human T lymphocytes or by treatment with IL-2, hIOs were injected under the kidney capsule of immunodeficient NSG mice. As a result, all types of major intestinal markers, including enterocytes, enteroendocrine cells, goblet cells, and Paneth cells, were found to be expressed in the transplanted hIOs (FIG. 14B) Further, neovascularization changes of the transplanted hIOs were measured. As a result, more vascular endothelial cells (CD31-positive cells) were detected in the co-cultured or IL-2-treated hIOs, which were differentiated from laminated human mesenchyme (α-smooth muscle actin (α-SMA)-positive cells)) (FIG. 13E, top panel).

These results indicate that in vitro-matured hIOs may potentially induce differentiation into human vascular cells in vivo, and may express more vascular endothelial growth factor (VEGF) (FIG. 13E, panel), and may be connected to the blood vessel of the host to increase the probability of transplantation success. These results also indicate that the in vitro-matured hIOs have normal karyotypes (FIG. 16), and thus may be a potential alternative source of cells for clinical intestinal transplantation.

Still another aspect of the present invention provides a tissue therapeutic agent including the in vitro-matured intestinal organoids prepared by the above method.

Still another aspect of the present invention provides a method of treating an intestine-related disease, the method including the step of transplanting, into a subject, the matured intestinal organoids prepared by the above method.

The 'orcanoids' and 'matured intestinal organoids' are the same as described above.

As used herein, the "subject" refers to all animals including a human, or a monkey, a cow, a horse, a sheep, a pig, a chicken, a turkey, a quail, a cat, a dog, a mouse, a rat, a rabbit, or a guinea pig that may already have or may develop the intestine-related disease. Any kind of the subject may be included without limitation, as long as the intestine-related disease may be effectively treated by administering the matured intestinal organoids of the present invention to the subject.

As used herein, the term "intestine-related disease" may include inflammatory bowel disease (IBD), Crohn's disease, short bowel syndrome, enterocolitis, and hirschsprung's disease which is a hereditary bowel disease, but is not limited thereto.

As used herein, the term "treatment" means all of the actions by which the intestine-related disease has taken a turn for the better or been modified favorably by transplantation of the matured intestinal organoids and by direct administration of the cytokines, STAT3, mTOR signaling activators, or a combination thereof used in the in vitro maturation.

Still another aspect of the present invention provides a kit for screening of a therapeutic agent for intestinal diseases, the kit including the in vitro-matured intestinal organoids. The kit for screening of the present invention may include the matured intestinal organoids specific to a patient with the intestine-related disease, thereby being usefully applied to screening of the disease or patient-customized therapeutics.

The "matured intestinal organoids" and "intestine-related diseases" are the same as described above.

Still another aspect of the present invention provides a method of screening for a therapeutic agent for an intestine-related disease, the method including the steps of (a) treating matured intestinal organoids derived from a patient with the intestine-related disease with a test substance; and (b) comparing mRNA or protein expression levels which are increased or decreased in the matured intestinal organoids derived from the patient with the intestine-related disease, as compared with those in intestinal organoids derived from a normal person, with those in the matured intestinal organoids derived from the patient, which are treated with the test substance of the step (a), and in the intestinal organoids derived from the normal person, which are not treated with the test substance.

The 'matured intestinal organoids' and 'intestine-related diseases' are the same as described above.

Further, the screening method may further include the step of selecting, as a therapeutic agent, a test substance capable of decreasing mRNA or protein expression which is increased in the matured intestinal organoids derived from the patient with the intestine-related disease, as compared with the matured intestinal organoids derived from the normal person, or a test substance capable of inhibiting the increase.

Further, the screening method may further include the step of selecting, as a therapeutic agent, a test substance capable of increasing mRNA or protein expression which is decreased in the matured intestinal organoids derived from the patient with the intestine-related disease, as compared with the matured intestinal organoids derived from the normal person, or a test substance capable of inhibiting the decrease.

As used herein, the term "test substance" may be individual nucleic acids, proteins, other extracts or natural products, or compounds which are assumed to have a possibility of treating the intestine-related diseases or randomly selected according to a common selection method.

The substances obtained by the screening method will serve as a leading compound in the process of developing a therapeutic agent for intestine-related diseases in the future.

By modifying and optimizing the leading substances, new prophylactic or therapeutic agents for autoimmune diseases may be developed.

Therefore, the screening method of the present invention may be usefully applied to searching and developing prophylactic or therapeutic agents for intestine-related diseases.

Hereinafter, the present invention will be described in more detail with reference to Examples. However, these Examples are for illustrative purposes only, and the invention is not intended to be limited by these Examples.

Experimental Example 1. Cell Culture and iPSC Generation

Human fibroblast (CRL-2097 and IMR90) and human T-lymphocyte (Jurkat T cells) were obtained from ATCC (American Type Culture Collection). H9 human embryonic stem cell (hESC) line was purchased from WI (WiCell Research Institute, Madison, USA).

Fibroblasts and hPSCs (human pluripotent stem cells), including hESCs (human embryonic stem cells) and hiPSCs (human induced pluripotent stem cells), were cultured by a known method (Molecular carcinogenesis 55, 0.387-396 (2016), Proteomics 15, 2220-2229 (2015)). Integration-free hiPSCs were reprogrammed by transfect ion through electroporation using Episomal iPSC Reprogramming Vectors (Cat. No. A14703. Invitrogen, Carlsbad, CA, USA) according to a known method.

Five days after electroporation, fibroblasts were seeded onto 6-well plates coated with Matrigel (BD Biosciences, San Diego, CA, USA) at a density of $1\times10^5$/well in EE medium (Stem Cell Technologies, Vancouver, Canada). After 3 weeks, hiPSC colonies were picked and sub-cultured, and the number of cells was expanded for further characterization.

Experimental Example 2. Differentiation of hPSCs into Intestinal Organoids (hIOs) for Preparation of Immature Intestinal Organoids Human intestinal organoids (hIOs) were generated using a known method (Nature 470, 0.05-109 (2011)). To induce definitive endoderm identity, hPSCs were treated with 100 ng/ml Activin A (R&D Systems, Minneapolis, MN, USA) for 3 days in RPMI 1640 medium with concentrations of 0%, 0.2% and 2% defined fetal bovine serum (dFBS, HyClone, Thermo Fisher Scientific Inc., Waltham, MA, USA). 500 ng/ml FGF4 (R&D Systems) and 500 ng/ml WNT3A (R&D Systems) were then treated for 4 days together with RPMI 1640 medium containing 2% dFBS in order to promote differentiation into 3D hindgut spheroids. The spheroids were embedded in Matrigel (BD Biosciences) and cultured in hIO medium together with DMEM/F12 medium containing 1×B27 (Invitrogen), 500 ng/ml R-Spondin 1 (R&D Systems), 100 ng/ml EGF (R&D Systems) and 100 ng/ml Noggin (R&D Systems), and then passaged every 2 weeks.

Experimental Example 3. Culture of hIO for Preparation of Mature Intestinal Organoids (Mature hIOs)

For co-culture with human T lymphocyte, Jurkat T cells were stimulated with both 50 ng/ml phorbol myristate acetate (PMA; Sigma-Aldrich, St. Louis, MO, USA) and 500 ng/ml calcium ionophore A23187 (Sigma-Aldrich) for 3 hr. A Transwell polyester membrane insert (pore size: 0.4

µm, Corning, Corning, NY, USA) on which hIOs had been embedded within Matrigel (BD Biosciences) was placed into a 12-well plate containing stimulated Jurkat T cells which had been seeded at 5×10⁴/cm² in hIO medium.

To assess the effect of interleukin 2 (hereinafter, referred to as IL-2) on hIOs, prepared rhIL-2 (R&D Systems) was added daily to hIO medium at a concentration of 1 ng/ml (approximately 13 U/ml). Further, to inhibit IL-2 signaling, hIOs were treated with 1 µg/ml of anti-IL-2Rα monoclonal antibody (R&D Systems). To block IL-2 downstream signal transduction, a mTOR inhibitor Rapamycin (10 nM, Sigma-Aldrich), a STAT3 inhibitor S31-201 (10 µM, Sigma-Aldrich), or Stattic (1 µM, Sigma-Aldrich) was added. To estimate the size of hIOs, surface areas of horizontal cross-sections of hIOs were measured.

Experimental Example 4. Quantitative RT-PCR (qPCR)

Total RNA was extracted from cells using an RNeasy Kit (Qiagen), and reverse-transcribed using a Superscript III cDNA synthesis kit (Invitrogen). qRT-PCR was performed by a method disclosed in a 7500 Fast Real-time PCR system (Applied Biosystems, Foster City, CA, USA) (Cho et al., Oncotarget 6, 23837-23844, 2015). All experiments were performed in triplicate, and CT value of each target gene was calculated using a software provided by the manufacturer. Nucleotide sequences of the used primers are as in Table 1.

TABLE 1

| Gene | Primer (Forward) | SEQ ID No. | Primer (Reverse) | SEQ ID No. |
|---|---|---|---|---|
| GAPDH | GAAGGTGAAGGT CGGAGTC | 1 | GAAGATGGTGAT GGGATTTC | 2 |
| CDX2 | CTGGAGCTGGAG AAGGAGTTTC | 3 | ATTTTAACCTGC CTCTCAGAGAGC | 4 |
| SOX9 | GGAGAGCGAGGA GGACAAGTTC | 5 | TTGAAGATGGCG TTGGGGG | 6 |
| LYZ | AAAACCCCAGGA GCAGTTAAT | 7 | CAACCCTCTTTG CACAAGCT | 8 |
| VIL1 | AGCCAGATCACT GCTGAGGT | 9 | TGGACAGGTGTT CCTCCTTC | 10 |
| CHGA | TGACCTCAACGA TGCATTTC | 11 | CTGTCCTGGCTC TTCTGCTC | 12 |
| MUC2 | TGTAGGCATCGC TCTTCTCA | 13 | GACACCATCTAC CTCACCCG | 14 |
| ISX | CAGGAAGGAAGG AAGAGCAA | 15 | TGGGTAGTGGGT AAAGTGGAA | 16 |
| LGR5 | TGCTCTTCACCA ACTGCATC | 17 | CTCAGGCTCACC AGATCCTC | 18 |
| SI | GGTAAGGAGAAA CCGGGAAG | 19 | GCACGTCGACCT ATGGAAAT | 20 |
| VIM | AGAACGTGCAGG AGGCAGAAGAAT | 21 | TTCCATTTCACG CATCTGGCGTTC | 22 |
| OLFM4 | ACCTTTCCCGTG GACAGAGT | 23 | TGGACATATTCC CTCACTTTGGA | 24 |
| DEFA5 | CCTTTGCAGGAA ATGGACTC | 25 | GGACTCACGGGT AGCACAAC | 26 |

TABLE 1-continued

| Gene | Primer (Forward) | SEQ ID No. | Primer (Reverse) | SEQ ID No. |
|---|---|---|---|---|
| DEFA6 | GCCTAGACACTG ATGACCCC | 27 | GCATGCTGTATT GCGCCTC | 28 |
| KRT20 | TGGCCTACACAA GCATCTGG | 29 | TAACTGGCTGCT GTAACGGG | 30 |
| SLC5A1 | GTGCAGTCAGCA CAAAGTGG | 31 | ATGCACATCCGG AATGGGTT | 32 |
| MUC13 | CGGATGACTGCC TCAATGGT | 33 | AAAGACGCTCCC TTCTGCTC | 34 |
| CREB3L3 | ATCTCCTGTTTG ACCGGCAG | 35 | GTCGTCAGAGTC GGGGTTTG | 36 |
| IL-2Rα | TCTTCCCATCCC ACATCCTC | 37 | TCTGCGGAAACC TCTCTTGC | 38 |
| IL-2Rβ | GGCTTTTGGCTT CATCATCT | 39 | CTTGTCCCTCTC CAGCACTT | 40 |
| IL-2Rγc | ACGGGAACCCAG GAGACAGG | 41 | AGCGGCTCCGAA CACGAAAC | 42 |
| P-GP | GCCAAAGCCAAA ATATCAGC | 43 | TTCCAATGTGTT CGGCATTA | 44 |

Experimental Example 5. Cells and Immunofluorescence Analysis

An immunofluorescence analysis was performed according to a known method (Kwak et al., Biochemical and biophysical research communications 457, 554-560, 2015). In detail, hPSCs and definitive endodermal cells were fixed in 4% paraformaldehyde (PFA) and then permeabilized with PBS containing 0.1% Triton X-100.

hIOs and tissues were fixed, cryo-protected in sucrose, and frozen using an optimal-cutting-temperature (OCT) compound (Sakura Finetek, Tokyo, Japan). Then, frozen sections were cut at a thickness of 10-20 µm using a cryostat microtome at −20° C. and permeabilized with PBS containing 0.1% Triton X-100 for immunofluorescence analysis.

In detail, after being blocked with 4% BSA, cells were incubated with primary antibodies at 4° C. overnight, and then incubated with secondary antibodies for 1 hr at room temperature. The used primary antibodies are as in Table 2. Paraffin sections were deparaffinized, subjected to antigen retrieval, and stained in a similar manner to OCT sections. DAPI was added to visualize nuclei. Slides were examined with an Axiovert 200M microscope (Carl Zeiss, Gottingen, Germany) or a fluorescence microscope (IX51, Olympus, Japan).

TABLE 2

| Antibody | Catalog No. | Company | Dilution |
|---|---|---|---|
| Pluripotency markers | | | |
| anti-OCT4 | sc-9081 | Santa Cruz | 1:100 for IF |
| anti-NANOG | AF1997 | R&D systems | 1:40 for IF |
| anti-SSEA-3 | MAB1434 | Millipore | 1:30 for IF |
| anti-SSEA-4 | MAB1435 | Millipore | 1:30 for IF |

TABLE 2-continued

| Antibody | Catalog No. | Company | Dilution |
|---|---|---|---|
| anti-TRA-1-60 | MAB4360 | Millipore | 1:100 for IF |
| anti-TRA-1-81 | MAB4381 | Millipore | 1:100 for IF |
| In vitro differentiation markers | | | |
| anti-TUJ1 | PRB-435P | Covance | 1:500 for IF |
| anti-NESTIN | MAB5326 | Millipore | 1:100 for IF |
| anti-FOXA2 | 07-633 | Millipore | 1:100 for IF |
| anti-SOX17 | MAB1924 | R&D systems | 1:50 for IF |
| anti-DESMIN | AB907 | Chemicon | 1:50 for IF |
| Intestinal organoid differentiation markers | | | |
| anti-CDX2 | ab15258 | abcam | 1:100 for IF |
| anti-KLF5 | ab137676 | abcam | 1:100 for IF |
| anti-SOX9 | sc-7314 | Santa Cruz | 1:50 for IF |
| anti-Villin | sc-7672 | Santa Cruz | 1:50 for IF |
| anti-Mucin2 | sc-7314 | Santa Cruz | 1:50 for IF |
| anti-Chromogranin A | MA5-14536 | Thermo Scientific | 1:200 for IF |
| anti-Lysozyme | ab76784 | abcam | 1:200 for IF |
| anti-E-Cadherin | 610182 | BD Biosciences | 1:200 for IF |
| anti-E-Cadherin | AF648 | R&D systems | 1:500 for IF |
| anti-α-SMA | A5228 | Sigma | 1:500 for IF |
| Intestine maturation markers | | | |
| anti-alpha 5 Defensin | ab90802 | abcam | 1:50 for IF |
| anti-OLFM4 | ab85046 | abcam | 1:100 for IF |
| anti-MUC13 | ab124654 | abcam | 1:100 for IF |
| anti-Cytokeratin 20 | ab76126 | abcam | 1:400 for IF |
| anti-Ki67 | AB9296 | Chemicon | 1:100 for IF |
| Intestinal transporter markers | | | |
| anti-SI (Sucrase-isomaltase) | HPA011897 | Sigma | 1:100 for IF |
| anti-PEPT1 | sc-20653 | Santa Cruz | 1:100 for IF |
| anti-MDR-1 | MAB4120 | Chemicon | 1:100 for IF |
| Vasculature markers | | | |
| anti-hCD31 | MA5-15336 | Thermo Scientific | 1:400 for IF |
| anti-PECAN-1 | sc-8306 | Santa Cruz | 1:50 for IF |
| anti-MECA-32 | NB100-77668 | Novus Biologicals | 1:400 for IF |
| anti-VEGF | sc-152 | Santa Cruz | 1:50 for IF |
| STAT3 signaling markers | | | |
| anti-STAT3 | #9132 | Cell Signaling | 1:2000 for WB |
| anti-phospho-STAT3(Tyr707) | #9131S | Cell Signaling | 1:2000 for WB |
| anti-AKT | #9272S | Cell Signaling | 1:1000 for WB |
| anti-phospho-AKT(Ser473) | #9271S | Cell Signaling | 1:1000 for WB |
| anti-P70-s6-kinase | #2708 | Cell Signaling | 1:1000 for WB |
| anti-phospho-P70-s6-kinase(Thr389) | #9205 | Cell Signaling | 1:1000 for WB |
| anti-β-Actin | sc-81178 | Santa Cruz | 1:2000 for WB |
| IL-2 receptor antibody | | | |
| anti-IL-2 receptor α | ab61777 | abcam | 1:2000 for WB |
| anti-IL-2 receptor β | ab197934 | abcam | 1:2000 for WB |
| anti-IL-2 receptor γ | ab180698 | abcam | 1:2000 for WB |
| IL-2 receptor blocker | | | |
| anti-IL-2 receptor β | AF-224-NA | R&D systems | 3 ug/ml for cell treatment |
| anti-IL-2 receptor γ | MAB2842 | R&D systems | 100 ng/ml for cell treatment |

*IF: Immunofluorescence
*WB: Western blotting

Experimental Example 6. Human Phospho-Kinase Array

Protein phosphorylation was quantified using a Proteome Profiler Human Phospho-Kinase Array Kit (ARY003, R&D Systems) according to the manufacturer's instructions and a known method (Human molecular genetics 23, 1802-1816 (2014)). Protein extracts were prepared from hIOs which were co-cultured with human T lymphocytes and treated with 1 ng/ml rhIL-2. Non-treated hIOs were used as a control group. The phospho-kinase array membranes were blocked, incubated with 200 μg of total protein from hIOs overnight at 4° C., and then incubated with cocktails of biotinylated detection antibodies for 2 hr at room temperature. Signal was detected with an ECL Plus Western Blotting Detection System (GE Healthcare, Buckinghamshire, UK), and phosphorylated kinase levels were quantified by densitometry with Image Gauge software (Fuji Photo Film GMBH).

Experimental Example 7. Western Blotting

Protein abundance was assessed using Western blot according to a known method. In detail, cells were lysed with RIPA buffer, and debris was removed by centrifugation at 4° C. Then, 20 μg of total protein was electrophoresed using a 4-15% gradient gel (Ready Gel, Bio-Rad Laboratories, Hercules, CA), and transferred to a PVDF membrane.

Experimental Example 8. Measurement of Cytokine Secretion

Stimulated or unstimulated Jurkat T cells were cultured for 2 days. Each culture medium was collected, and levels of human TNFα, IL-1β, and IL-2 were determined using an enzyme-linked immunosorbant assay (ELISA, all from R&D Systems). ELISA was performed according to the manufacturer's instructions and a known method, followed by quantification with a Spectra Max M3 microplate reader (Molecular Devices, Sunnyvale, CA, USA).

Experimental Example 9. Microarray Analysis

Microarray experiments were conducted according to the manufacturer's instructions using a low RNA input linear amplification kit, cRNA cleanup module, and one-color (Cy3) Whole Human Genome Microarray 4X44K (Agilent. Technology, Santa Clara, CA) by a known method. Gene expression data were processed using GeneSpring software (Agilent). The data were normalized using global scale normalization. Differentially expressed genes were selected on the basis of a fold-change greater than 2.

Experimental Example 10. RNA Sequencing and RNA Quantification

For determination of RNA sequence and quantification, only RNA samples with RNA integrity Number (RIN)≥7.5 were first prepared using an Agilent 2100 Bioanalyzer system (Agilent Biotechnologies, Palo Alto, USA). mRNA libraries were prepared using an Illumina TruSeq kit and sequencing was performed on Illumina HiSeq2500 machines (Illumina, San Diego, CA, USA). Sequencing quality was assessed with the FastQC package. If the trimmed read length was less than 50 bp, it was excluded. Thereafter, mapping was performed using HISAT2 (v2.0.5). The human genome information from hg19 was used. The differentially expressed genes (DEGs) between samples were analyzed with Cuffquant and Cuffnorm (Cufflinks v2.2.1).

Experimental Example 11. Bioinformatic Analysis

Microarray data analysis was performed as described in Experimental Example 9. Hierarchical clustering and the heat map were generated using MeV v 4.9.0 software. Gene functions were annotated using GeneCard database (genecards.org). Other bioinformatic analyses were performed using IPA analysis software (Ingenuity systems, Redwood City, CA, USA), PANTHER (Protein ANalysis THrough Evolutionary Relationships, http://www.pantherdb.org) database, and DAVID Bioinformatics Resources 6.7 (david.abcc.ncifcrf.gov/). Differentially phosphorylated proteins were used for analysis and visualization of functional interaction networks. Core pathways in the network were further analyzed using Reactome (Reactome FI software, Version 5.0.0 beta, apps.cytoscape.org/apps/reactomefis). The functionally grouped gene ontology (GO)/pathway was analyzed using Cytoscape software platform (version 3.3.0, http://www.cytoscape.org/what_is_cytoscape.html) with ClueGO plug-in (Version 2.2.5, apps.cytoscape.org/apps/cluego).

Experimental Example 12. P-Glycoprotein (P-Gp)/MDR1 Transport Assay

To reveal P-glycoprotein transporter activity, at least 20 hIOs per group were used in triplicate. hIOs were plated in 4-well plates, washed three times with Hank's balanced salt solution (HBSS with calcium and magnesium, pH=7.4, Invitrogen) containing 25 mM HEPES and incubated at 37° C. for 30 min. The P-gp substrate paclitaxel (10 μM, Sigma-Aldrich) in DMSO was added to hIO cultures and incubated on a shaker (50 rpm, 2 hr) in the presence or absence of verapamil, which is a P-gp inhibitor, in PBS (50 μM, Sigma-Aldrich). After incubation, hIOs were washed three times with HBSS and ruptured with an ultrasonic cell disrupter. Thereafter, the homogenate was centrifuged at 13,000×g for 10 min at 4° C., and the resulting supernatant was collected. The concentration of paclitaxel in each sample was quantitated by LC-ESI/MS/MS analysis using a 3200 QTRAP LC-MS/MS system (Applied Biosystems) equipped with a Turbo V™ Ion Spray source and an Agilent 1200 series HPLC system (Agilent Technologies).

Experimental Example 13. Glucose-Mediated Calcium Imaging with Fluo4-AM Calcium Indicator To reveal the glucose transporter function of mature small, intestine epithelial cells, a glucose-mediated intracellular calcium release-inducing technique was used. Control or matured hIOs were incubated in hIO medium added with Fluo4-AM (5 μM, Molecular Probes) at 37° C. for 1 hr. hIOs were then washed five times with $Ca^{2+}$-free buffer (140 mM NaCl, 5 mM KCl, 10 mM HEPES, 5.5 mM D-Glucose, 2 mM $MgCl_2$) and filled with $C^{2+}$-free buffer, followed by real time imaging with a confocal microscope (FV000 Live, Olympus). 50 mM glucose was used to induce intracellular calcium release, and fluorescence signals were recorded in real time. 15 regions of interest (ROI) were determined to plot a graph.

Experimental Example 14. CFTR Function Analysis Using Forskolin

To examine the function of CFTR present in mature intestine epithelial cells in organoid models, forskolin-induced organoid swelling assay was performed. Control and co-cultured or IL-2-treated hIOs (n=4) were treated with forskolin (25 uM, Merckmillopore), and then morphological observation was performed for 120 min at 20 min intervals through live imaging function of a microscope (IX83, Olympus). CFTR inhibitors (CFTRinh172, GlyH101) were co-treated, and morphological observation was performed for the same time. The size of organoids was calculated every hour, and mean values thereof were used to plot a graph.

Experimental Example 15. PAS/Mucicarmine Staining Experiments

Mature functional goblet cells were detected in mature intestinal organoids using a technique of staining mucin secreted from mature goblet cells. First, control and mature intestinal organoids were fixed in 4% para-formaldehyde, and further fixed in 10%, 20%, and 30% sucrose solutions. Thereafter, the organoids were frozen using OCT and the frozen sections were cut at a thickness of 10 um using a cryostat microtome, and attached onto slide glass, followed by staining.

Experimental Example 16. Hormone Secretion Assay

Secretion of gastric inhibitory polypeptide (GIP) hormone expressed by enteroendocrine cells was examined to examine functionality of mature enteroendocrine cells. First, 15 organoids under different conditions were placed on culture plates, and washed with PBS five times, and hIO culture medium was added, followed by incubation for 48 hr at 37° C. Thereafter, the supernatant was harvested, and quantity of GIP in the culture was measured using a total GIP ELISA kit (Merckmillopore). Then, gDNA of the total amount of hIOs used in the experiment was extracted using a DNeasy kit (Qiagen), and the quantity of GIP hormone relative to DNA was calculated and schematized.

Experimental Example 17. Transplantation 8 to 12-week-old NOD-SCID IL-2Rγnull (NSG) mice were used in all experiments for transplantation (Jackson Laboratories, Bar Harbor, ME, USA). All mice were housed in a standard animal maintenance facility at a constant temperature (20-22° C.) with a 1.2:12 h light: dark schedule. Ethical approval was received for all experiments from the Institutional Animal Care and Use Committee (IACUC) of KRIBB (Approval No: KRIBB-AEC-16206).

Xenografting of hIOs under the kidney capsule was performed by a known method (Nat Med 20, 131.0-1314 (2014)). In detail, mice were anesthetized with 2% isoflurane (Butler Schein, Dublin, OH, USA), and the left side of the mouse was then prepared using isopropyl alcohol and povidone-iodine in the standard manner. A left subcostal incision was made to expose the kidney. Then, hIOs in the collagen plug were then transplanted into the subcapsular space of the kidney. Then, the kidney was returned to the peritoneal cavity and the mice were administered with an IP flush containing Enrofloxacin (5 mg/kg; Daehan New Pharm Co.). The skin was closed with a double layer and mice were kept warm with a heating pad until they had recovered fully from the anesthesia. Mice were euthanized humanely one week after transplantation, and the xenografts were isolated for analysis.

Experimental Example 18. In Vivo Fluorescence Imaging

To monitor the transplanted hIOs, hIOs were incubated with 1,1-dioctadecyl-3,3,3,3-tetramethylindotricarbocyanine iodide (DiR, Invitrogen) in 4-well plates at 37° C. for 15 min. After washing with PBS, hIOs were incubated with fresh medium, and then transplanted under the kidney capsule. To visualize fluorescence in vivo, the recipient mice (n=3) were anesthetized with 2% inhaled isoflurane (Terrell™, Piramal Healthcare, Bethlehem, PA, USA) one day after transplantation and placed into a light-sealed chamber connected to a charge-coupled device camera.

To confirm the exact size of the transplanted hIOs, the kidneys of the recipient mice were isolated one week after transplantation, and placed in a light-sealed chamber connected to a charge-coupled device camera. The fluorescence intensity of each region of interest was measured with In Vivo Imaging System (IVIS Lumina II, Xenogen Corp., Alameda, CA, USA) with emission at 780 nm and excitation at 750 nm.

Experimental Example 19. Statistical Analysis

All results are expressed as mean±standard error (s.e.m) of the mean, and all experiments were repeated at least three times. P values were determined using two-tailed t-tests. All analyses of statistical significance were calculated and compared with the control group unless otherwise stated.

Experimental Example 20. Measurement of Episomal Copy-Number hiPSC lysates prepared using 1×Taq buffer (Takara, Kyoto, Japan) and proteinase K at 55° C. for 3 hr were used for qPCR analysis as described previously. A known concentration of pCXLE-hFbx15-cont2 plasmid was used to create a standard curve. The copy number of EBNA1 and FBXO15 in each hiPSC was calculated from the threshold cycle (Ct) values obtained over six replicates.

Experimental Example 21. STR (Short Tandem Repeat) and Karyotype Analysis

STR analysis was performed by HumanPass, Inc. (Seoul, Korea) using genomic DNA isolated from fibroblasts and the corresponding iPSC lines. Further, G-banding karyotype analysis was performed by GenDix, inc. (Seoul, Korea). Data were expressed as mean±SD (n=3) (***p<0.001 (Unpaired student's t-test).

Experimental Example 22. In Vitro Differentiation Via Embryoid Body (EB) Formation For natural differentiation into three germ layers, hiPSCs were separated by treatment with 1 mg/ml collagenase IV, and plated in a Petri dish containing knockout DMEM EB medium supplemented with 10% knockout serum alternative, 1% non-essential amino acids, 0.1 nM β-mercaptoethanol, and 1 mM L-glutamine. 5 days after suspension culture, embryoid bodies (EBs) were transferred onto a Matrigel-coated LabTek chamber slide (Nunc International, Naperville, Il, USA), and further cultured for 10 days.

Experimental Example 23. In Vivo Differentiation Via Teratoma Formation

A total of $1 \times 10^6$ cells were mixed with Matrigel and injected subcutaneously into the dorso-lateral area of BALB/c nude mice (Orient Bio, Inc., Seongnam, Korea). After 8 to 10 weeks, the resulting teratomas were dissected, fixed in 4% PFA, and embedded in paraffin. Paraffin-embedded teratomas were sectioned and then stained with hematoxylin and eosin solution (Sigma-Aldrich). Animal experiments were approved by the Institutional Animal Care and Use Committee (IACUC) of KRIBB (Approval No: KRIBB-AEC-16206).

Experimental Example 24. Generation and Validation of STAT3 Knockout hESC Lines RNA was transcribed in vitro using the MEGAshortscript T7 kit (Ambion, Invitrogen) according to the manufacturer's manual. Templates for a synthetic guide RNA (sgRNA) were generated by annealing and extension of two complementary oligonucleotides (Supplementary Table S1). Transcribed RNA was purified by a MEGAclear Transcription Clean-Up Kit (Ambion). Purified RNA was quantified by spectrometry. H9 hESCs expressing Cas9 under the control of a tetracycline-responsive element were dissociated into single cells using gentle cell dissociation reagent (STEMCELL Technologies, Cambridge, MA, USA). Cells ($1 \times 10^6$) resuspended in Nucleofector solution were electroporated with 40 µg of in vitro transcribed sgRNA by using an Amaxa P3 Primary Cell 4D-Nucleofector Kit (Lonza, Walkersville, MD, USA). Cells were maintained in the presence of doxycycline. After 3 days, cells were replated as single cells at a very low density on Laminin 521-coated plates in Essential 8 medium (Thermo Fisher Scientific) supplemented with Rho kinase (ROCK) inhibitor (Y-27632, Stemgent, MA, USA). Individual colonies were picked and expanded. Genomic DNA was then extracted using QuickExtract (Epicenter, Madison, WI, USA) according to the manufacturer's instructions. The target region was amplified using Phusion polymerase (New England Biolabs Inc., Ipswich, MA, USA) (Supplementary Table 32) and used for library construction. PCR amplicons were subjected to paired-end read sequencing using Illumina MiSeq (Illumina, San Diego, CA, USA). For T7 endonuclease I (T7E1) assay, 200 ng of DNA heteroduplexes of PCR products obtained from WT and STAT3 KO cells were incubated with 10 U of T7E1 at 37° C. for 15 min in a reaction volume of 20 ul. The reactions were analyzed by 2% agarose gel electrophoresis.

Example 1. Co-Culture with Human T Lymphocytes to Overcome Immature Pattern of Intestinal Gene Expression in hPSC-Derived hIOs As described above, hIO differentiation protocol was used to prepare hIOs, one derived from hESC line and two derived from fully characterized, integration-free hiPSC line (FIG. 1A)-containing hPSCs.

hPSCs were confirmed to be efficiently differentiated into definitive endoderm, hindgut, and hIO that mimics the intestinal tissue by their characteristic morphologies and expression of stage-specific markers (FIGS. 2A, 2B, and 3A) Further, it was observed that the expression of human small intestinal (his) markers, such as intestinal transcription factors (SOX9 (SRY (sex determining region Y)-box9), CDX2 (Caudal Type Homeobox 2) and KLF5 (Kruppel like factor 5)) and intestinal cell type-specific markers, such as VIL (villin 1 for enterocytes), MUC2 (mucin 2 for goblet cells), LYZ (lysozyme for Paneth cells), and CHGA (lysozyme for Paneth cells) was increased with increasing passage of subculture (FIG. 2C).

In the principal component analysis (PCA) from microarray results at each stage, when global gene expression profile of hIO at passage 2 (p2) was compared with that of hIO at passage 0 (p0), it was more similar to hSI control. (FIG. 3B). These results confirmed that hIOs after a series of passages acquired more differentiated phenotypes of intestinal cell type-specific gene expression and morphology, as known previously.

However, hPSC-derived hIOs (p0, p2) still showed reduction in expression of numerous genes associated with intestinal maturation, such as Paneth cell function, digestive function, and host defense by an intestinal stem cell (ISC) marker (e.g., OLFM4) (FIG. 3D).

These results confirmed that matured intestinal organoids showed reduction in expression of numerous genes associated with intestinal maturation, such as Paneth cell function (e.g., DEFA5, DEFA6), digestive function (e.g., DPP4, LCT), and host defense by the intestinal stem cell (ISC) marker (e.g., OLFM4), as known previously, indicating that hPSC-derived hIOs are very similar to the fetal small intestine.

Further, it was confirmed that hIOs stably expanded for 10 passages or more (150 days) while maintaining a particular structure including all types of IEC (intestinal epithelial cells) (FIG. 3A). However, it was confirmed that mRNA levels of small intestine cell type-specific markers (VIL1, LYZ, CHGA, and MUC2) were not further increased between hIOs at passage 2 and hIOs at several passages (p8, p10) (FIG. 3E). In particular, it was confirmed that mRNA levels of intestinal maturation markers such as α-defensin, OLEM4, DEFA5, DPP4 and LCT produced by mature Paneth cells were maintained very low with developmental progression (FIG. 3E).

IECs (intestinal epithelial cells) secrete soluble factors to interact with immune cells in the intestinal mucosa, thereby maintaining homeostasis and promoting maturation of intestinal epithelium. To mimic the in vivo intestinal environment, a co-culture system that enables crosstalk between the hIOs and the immune cells via the soluble factors secreted from each cell was used. In detail, hIOs were placed onto Transwell inserts on which hIOs had been embedded within Matrigel, and PMA/ionophore-stimulated Jurkat T cells which are a source of human T lymphocyte were placed on 12-well plate (FIG. 5A). Co-culture with Jurkat T cells remarkably increased the size of hIO (FIG. 5E), and gene expression of intestinal maturation markers was increased in hIOs organoids co-cultured with NS Jurkat T cells or stimulated Jurkat T cells (FIG. 5C).

Similarly, incubation in a conditioned medium (CM) having Jurkat T cells increased the size of hIOs (FIG. 3F), indicating that hIOs are affected by secreted paracrine factors without direct contact with Jurkat T cells. Further, PCA confirmed that the transcriptome of co-cultured hIOs more closely resembles that of hSI (FIG. 3B).

As a result, hierarchical clustering of samples, based on genes involved in intestinal maturation such as defense response, intestinal markers, and digestive function, revealed that co-cultured hIOs are very similar to mature hSI (FIG. 3D). These results indicate that hPSC-derived hIOs are differentiated into mature intestinal organoids when cultured under experimental conditions used in the present invention.

Example 2. Analysis of Major Secreted Factors During Co-Culture with Human T Lymphocytes To determine major secreted factors in the co-culture system, expression levels of soluble proteins were measured by ELISA. Stimulated Jurkat T lymphocytes released significantly higher amounts of IL-2 than other cytokines, including tumor necrosis factor alpha (TNFα), IL-θ and IL-1β (FIG. 6A). Further, mRNA expression levels of IL-2 receptor beta (IL-2Rβ) and gamma chain (IL-2Rγc) chain were increased in the hIOs after hIO co-culture with stimulated human T lymphocytes (FIG. 6B). Dimerization of the beta (IL-2Rβ) and gamma chain (IL-2Rγc) contributes to IL-2-mediated signaling by formation of medium affinity for IL-2Rbgc receptor. Further, the signaling pathway of hIOs co-cultured with human T lymphocytes was analyzed by performing a phospho-kinase array detecting activities of 43 kinases according to environmental changes. Some of the kinases exhibited a noticeable difference (>1.2-fold change) in their phosphorylation status between the control group and the co-cultured group (FIGS. 8A and 8B). In particular, most highly phosphorylated proteins were found to be involved in the IL-2-mediated signaling pathway such as STAT3, c-Jun, p38α, and ERK1/2 (FIG. 6C). Further, pathway enrichment analysis revealed that the IL-2-mediated signaling pathway was one of the most heavily upregulated pathways in the co-cultured hIOs (adjusted FDR<0.001) (FIG. 6D).

These results suggest that the cytokines are one of important paracrine soluble factors in the co-culture system and play a critical role of in vitro intestinal maturation effect.

Example 3. IL-2 Promoting hIO Growth and Activating STAT3 and mTOR Pathways

To confirm that IL-2 is a potential key factor in the effect of co-culture on the in vitro maturation of hIOs, experiments were performed using recombinant human IL-2 (rhIL-2).

In detail, hPSC-derived hIOs cultured with IL-2 significantly increased in size, and the size increase of the hPSC-derived hIOs was inhibited by the selective blockade of the IL-2 receptor (FIG. 7A). Expression of mature intestinal markers was completely inhibited by blocking the IL-2 signaling (FIG. 7B). Further, it was confirmed that treatment with IL-2 at a concentration of 1 ng/ml to 4 ng/ml significantly increased the size of hIO having a complex 3D intestinal epithelial structure (FIG. 9). Further, phosphoryl at ion events induced by IL-2 treatment were measured by a human phospho-kinase array analysis. As a result, phosphorylation of STAT3 (Y705) was the most substantially altered, and it was 3.3-fold increase after IL-2 treatment (FIGS. 8C, 8D, and 7C).

It was confirmed that differentially phosphorylated proteins in the control and IL-2-treated hIOs were significantly enhanced in the mTOR signaling pathways (adjusted FDR<0.005). When hIOs were co-cultured with human T lymphocytes or treated with IL-2, increased phosphorylation of AKT and 270 S6 kinases in the STAT3 and mTOR signaling pathways was confirmed (FIGS. 7D and 7E).

In particular, it was confirmed that the stimulation of IL-2 on hIO growth was prevented by addition of STAT3 (S31-201 or Stattic) or mTOR (rapamycin)-specific inhibitors, and most of the inhibitor-treated hIOs lost their morphological characteristics (FIG. 7F).

The microvilli length was correlated with a significantly higher expression of brush border enzymes, such as dipeptidyl peptidase IV (DPP4), sucrase isomaltase (SI), and lactase (LCT), in Mat-hIOs compared to Cont-hIOs. qPCR analysis also showed that Mat-hIOs (mature hIOs) contained mature and functional Paneth cells, as evidenced by the increased expression of antimicrobial peptides (DEFA5) secreted by mature Paneth cells, similar to hSI (FIG. 7G).

Most importantly, treatment with the STAT3 inhibitors completely ablated the expression of intestinal cell type-specific maturation markers, including mature intestinal stem cell marker (OLFM4), mature Paneth cell markers (DEFA5), mature goblet cell marker (MUC13), mature enteroendocrine cell markers (CHGA as a general enteroendocrine marker GIP as a marker of enteroendocrine K cells), mature enterocyte markers (SI, DPP4, LCT), and other intestinal markers (CDX2, KRT20) (FIG. 7G). Therefore, treatment with STAT3 inhibitors abrogated the in vitro maturation of hESC-derived hIOs.

These results indicate that cytokines are involved in growth and maturation of hPSC-derived hIOs by activating the STAT3 and mTOR signaling pathways.

It was also confirmed whether another STAT3 activator, colivelin promotes in vitro maturation of hIOs. When various concentrations of colivelin were used, the size of hIO was increased (FIG. 17A). Increased expression of intestinal maturation markers was examined by qPCR. As a result, overall expression was increased by colivelin treatment, as compared with control hIOs (FIG. 7B). Protein expression of proliferation marker (Ki-67) and intestinal maturation markers (OLFM4, MUC13 and KRT20) were increased by colivelin treatment.

Further, IL-2/STAT3 signaling is required for hIO maturation. We also found that treatment with STAT3 activators, such as Colivelin or IL-22, promoted the growth of hIOs with many crypt-like budding structures (FIGS. 18A and 18B).

Example 4. Co-Culture System and Growth Factors Affecting In Vitro Maturation of hIOs Gene expression profiling was performed to examine whether the IL-2-mediated signaling pathway is involved in in vitro maturation of hIOs in addition to its role in promoting the growth of hIOs. In detail, when co-cultured with human T lymphocytes or treated with IL-2, a shift was observed in the gene expression profile of hIOs, similar to expression patterns of the human adult intestinal control (hSI) (FIG. 10A). In particular, co-culture (55.9& of genes shifted towards the profile of hSI) was more effective than the treatment with IL-2 (49.8 of genes shifted towards the profile of hSI).

Further, in order to easily understand the biological meaning of differentially expressed genes (DEGs) related to intestinal maturation, a functional enrichment analysis was performed using ClueGO-in plug of Cytoscape.

As a result, among DEGs which were excessively prominent in mature hSIs and control hIOs, genes associated with key biological processes, including cell-cell adhesion, defense response, innate immune response, regulation of immune system process, positive regulation of response to stimulus, cell surface receptor signaling pathway, cellular response to chemical stimulus, signal transduction, signal transduction, cell communication, and response to cytokine, were significantly ($p<0.05$) expressed in the co-culture system or the IL-2 treatment (highlighted in gray) (FIG. 10B), similar to expression patterns in the human adult intestinal control (hSI) (nodes highlighted in red) (FIG. 10C).

In the co-cultured hIOs, the number of genes involved in the selected biological processes was 2-fold or more the number of genes in the IL-2-treated hIOs (FIG. 10D). Further, expression levels of genes involved in intestinal maturation including intestinal markers, digestive function, and defense function were slightly lower in the IL-2-treated hIOs than in the co-cultured hIOs, but slightly higher than in the control hIOs (FIGS. 10E to 10G).

To examine changes in the expression obtained from the microarray analysis, expression of genes involved in intestinal maturation was examined (FIG. 11A). Expression of an intestine-specific marker CDX2 and a mature intestine ISC marker OLFM4 was upregulated when co-cultured or IL-2-treated, but their expression levels were lower than those of hSI and human adult tissue-derived intestinal organoid (hAT-IO). However, expression of genes involved in regulation of innate immune responses for the host defense mechanism was apparently increased when co-cultured or IL-2 treated.

Expression levels of human α-defensin (DEFA5 and DEFA6) and lysozyme (LYZ) which are Paneth cell-specific components produced in the mature intestine were upregulated in the co-cultured or IL-2-treated hIOs. Expression of DPP4 and LCT involved in the digestive function of the mature intestine was upregulated in the co-cultured or IL-2-treated hIOs. Further, increased expression of the mature intestinal differentiation markers including KRT20, MUC13, SLC5A1, and CREB3L3 was observed in the co-cultured or IL-2-treated hIOs. There was no significant difference in the expression of the genes between the co-cultured or IL-2-treated hIOs and hAT-IOs. qPCR data consistently confirmed that protein expression of OLFM4, MUC13, and KRT20 was detected not in the control but in the co-cultured or IL-2-treated hIOs (FIG. 11B). Protein expression of functional sucrase-isomaltase (SI), MDR1 and peptide transporter 1 (PEPT1) was also detected in the co-cultured or IL-2-treated hIOs, as compared with the control (FIG. 11C).

These results indicate that the co-culture system or cytokine IL-2 treatment may induce in vitro maturation to allow the hPSC-derived immature hIOs having fetal-like characteristics to have adult intestinal characteristics.

Example 5. In Vitro-Matured hIO that Mimics Intestinal Functionality

To confirm that the mature small intestine plays a role in drug absorption and metabolism by regulating expression of transporters and drug-metabolizing enzymes at transcriptional and post-transcriptional levels, expression patterns of various genes related to transporters and metabolizing enzymes were analyzed.

As a result, main intestinal cytochrome p450 enzymes, conjugation enzymes, and uptake (solute carrier (SLC) family) and efflux (ATP-binding cassette (ABC)) transporters were highly expressed in hSI (FIG. 2A). Of 40 enzymes and transporters, 27 (67.5%) were upregulated by at least 2-fold in the co-cultured hIOs, and 25 (62.5 S) were upregulated in IL-2-treated hIOs, as compared with control hIOs. These results were much higher than those of hAT-IO (FIG. 12B). Hierarchical clustering shows that the co-cultured or IL-2-treated hIOs were preferentially clustered with control hSI. In particular, expression of some SLC and ABC transporters and sulfotransferase (SULT) enzyme was relatively low in hAT-IO (FIG. 12B).

Further, to confirm whether in vitro hIO maturation at a gene expression level influences the functional status of hIO, expression of P-glycoprotein (P-gp, MDR1, ABCB1) which is a major efflux transporter that affects the pharmacokinetics of a wide range of drugs and xenobiotics was examined in the co-cultured and IL-2-treated hIOs. As a result, the expression was upregulated in the co-cultured or IL-2-treated hIOs (FIG. 12D). Then, to assess functional quality of in vitro-matured hIOs, the efflux transporter function of hIOs was measured hIOs have a permeable intestinal epithelial barrier, as indicated by the paracellular diffusion pattern of FITC-dextran (FIG. 12C.

To assess the transporter activity of P-gp, paclitaxel which is a prototypic substrate was loaded to the basolateral side (outside) of the co-cultured and IL-2-treated hIOs and control. Following 2 hr-incubation, the concentrations of paclitaxel at the apical side (inside of cells) were increased approximately 2.3-fold ($p<0.001$) in the co-cultured hIOs and 3-fold ($p<0.001$) in the IL-2-treated hIOs, as compared with the control hIOs (FIG. 12D). When P-gp was inhibited by verapamil which is a calcium channel blocker, the concentrations of paclitaxel in the apical side significantly decreased in the co-cultured hIOs and the IL-2-treated hIOs (54.6%±5.8%, $p<0.001$ and 92.8±0.6%, $p<0.001$, respectively), as compared with the control hIOs (27.9%±15.6, $p>0.05$).

To assess glucose responsiveness of mature enterocytes, glucose-mediated calcium cytosolic release was quantified using a fluo-4AM calcium indicator. When glucose-induced calcium ion transients were observed by real-time imaging, calcium response was noticeable, as compared with the control, and high signal amplitudes (2-3 fold, $p<0.001$) were observed. Thus, it was confirmed that glucose responsiveness was superior in the matured hIOs, as compared with the control (FIG. 12F).

To assess CFTR expression of mature enterocytes, forskolin-induced organoid swelling assays were performed. After exposure to forskolin for 120 minutes, the size of organoids was quantified and compared by real-time imaging. Forskolin response was noticeable in the mature organoid experimental group (n=4), as compared with the control, and this swelling effect was completely blocked by treatment with a CFTR inhibitor (CFTR$_{inh}$72, GlyH101) (FIG. 12G), indicating high expression of functional CFTR protein by in vitro-matured hIOs.

Further, to examine functional organoids of the mucous layer and mature mucous-producing goblet cells, PAS/mucicarmine staining was performed. It was confirmed that PAS/mucicarmine-positive mucous layer and mucous-producing goblet cells were well functioned in in vitro-matured hIOs, as compared with the control (FIG. 12H).

To examine hormone secretion of enteroendocrine cells, the amount of GIP hormone was measured in culture supernatants of the control and the co-cultured or IL-2-treated hIOs. First, when GIP gene expression patterns of the control and in vitro-matured hIOs were examined by PCR, the GIP gene expression was greatly increased in the co-cultured or IL-2-treated hIOs, as compared with the control (FIG. 1.21), and consistently, when the amount of the secreted GIP was examined by using a GIP ELISA kit, the amount of GIP was increased about 45-fold in the co-cultured or IL-2-treated hIOs, as compared with the control (FIG. 12J).

These results indicate that not only the drug reactivity by P-gp expression but also each representative function of the intestinal cell are increased in the in vitro-matured hIOs.

Example 6. In Vitro-Matured hIO that Produces Functional Vascular Structure In Vivo To assess the suitability of in vitro-matured hIOs for transplantation by co-culture with human T lymphocytes or by treatment with IL-2, hIOs were injected under the kidney capsule of immunodeficient NSG mice. hIOs were labeled with DiR which is a near-infrared fluorescent lipophilic dye with low cytotoxicity to allow in vivo quantitative detection of the transplanted hIOs. The hIOs were confined inside of the kidney at 1 day post-transplantation (FIG. 14A), and the fluorescent signal was still detectable in the kidney taken after transplantation (FIG. 13A). In vivo IVIS imaging and histological examination of DiR-labeled hIOs revealed that the co-cultured and IL-2-treated hIOs showed significant increase in their sizes for 1 week after the transplantation, as compared with the control ($p<0.01$ and $p<0.05$, DiR fluorescence intensity in the co-cultured and IL-2-treated hIOs) (FIGS. 13A and 138). In the transplanted hIOs, markers of all types of major intestinal cells including enterocytes, enteroendocrine cells, goblet cells, and Paneth cells were detected (FIG. 14B). In particular, expression of mature intestinal differentiation markers was examined in the transplanted in vitro-matured hIOs, and as a result, DEFA5, OLFM4, MUC13, and KRT20-positive cells were consistently detected in vive (FIG. 13C). Further, functional brushborder enzymes such as sucrase-isomaltase (SIM) and functional intestinal transporters such as MDR1 and peptide transporter 1 (PEPT1) were exclusively expressed in the in vitro-matured hIOs after short-term transplantation (FIG. 13D).

Since one of main obstacles in the application of hPSC-derived cells and organoids to the tissue therapy is to provide vessel connection between the host vasculature and the transplanted parenchyma cells, neovascularization of in vivo-transplanted hIOs was measured. In detail, as compared with the control hIOs, more vascular endothelial cells (CD31-positive cells) were detected in the co-cultured or IL-2-treated hIOs, which were derived from laminated human mesenchyme ($\alpha$-smooth muscle actin ($\alpha$-SMA)-positive cells)) (FIG. 13E, top panel). CD31 expression was not detected even in in vitro-matured hIOs before transplantation (FIG. 15A). Moreover, the mesenchyme of the co-cultured and IL-2-treated hIOs showed high expression levels of vascular endothelial growth factor (VEGF), which is known to recruit blood vessels from adjacent tissues, as compared with the control, hIOs (FIG. 13E, middle panel). Actually, it was found that the co-cultured or IL-2-treated hIOs recruited mMECA-32-positive vessels from the host vasculature 1 week post-transplantation (FIG. 13E, bottom panel). Blood vessels including vascular endothelial cells derived from the mesenchyme of adjacent hIOs were rich in lamina propria in the co-cultured or IL-2-treated hIOs, as compared with the control hIOs, and they connected the mouse vasculature (FIG. 13E, arrows in bottom panel, and FIG. 15B)

These results suggest that in vitro-matured hIOs are potentially able to induce in vivo human vascular maturation, and the in vitro-matured hIOs also have normal karyotypes (FIG. 16), and thus may represent an effective alternative source of cells for clinical intestinal transplantation in the future.

Example 7. hIO Maturation Accompanied by STAT3 Activation (Phosphorylation)

As confirmed in the previous Examples, treatment with STAT3 inhibitors alters the morphology with reduced budding and surface area of hIOs, and IL-2 treatment over two passages results in formation of Mat-hIOs. To identify the mechanism of STAT3 which controls the in vitro maturation of hIOs, the STAT3 signaling pathway was examined. Intense phospho-STAT3 imunostaining for detecting phosphorylation at the tyrosine 705 (Y705) residue was visualized in Mat-hIOs compared to Cont-hIOs. As a result, STAT3 signaling activation was confirmed in the epithelial maturation of hIOs. The phosphorylation was blocked in the presence of Stattic and S3I-201 which are STAT3 inhibitors (FIG. 19).

Example 8. Maturation of hIOs Differentiated from STAT3 Knockout HESC Line

To investigate the role of STAT3 in the in vitro maturation of hPSC-derived hIOs, we attempted to generate STAT3 KO hESC lines. For the ecient generation of insertion/deletion (in/del) mutations mediated by CRISPR/Cas9, we designed a single sgRNA targeting the region immediately downstream of the start codon in the second exon of the STAT3 gene (FIG. 20A). The in vitro transcribed sgRNA was transfected into hESC line expressing Cas9 under the control of a tetracycline-responsive element (TRE) via electroporation in the presence of doxycycline (Dox). At 72 h post-transfection, cells were dissociated and replated as single cells at a very low density in hESC medium supplemented with Rho kinase (ROCK) inhibitor to obtain single cell-derived clones. After picking and expanding individual clones, we confirmed the disruption of the STAT3 targeted locus by deep sequencing (FIG. 20A). As a result, two frameshifted clones were isolated, and a single nucleotide insertion (+G in STAT3 KO clone #1) and deletion (−G in STAT3 KO clone #2) were confirmed. In addition, the T7E1 assay clearly showed enzymatically digested products, which mean the successful introduction of in/del mutations in the targeted region (FIG. 20B). We also observed the complete absence of STAT3 protein expression in two selected STAT3 KO hESC lines (KO #1 and KO #2) by Western blotting analysis (FIG. 20C).

Thus, we concluded that STAT3 KO hESC lines were successfully generated by CRISPR-Cas9 genome editing. We subsequently examined whether STAT3 KO hESC lines could maintain pluripotent characteristics by examining the expression of pluripotency markers. Similar to WT hESCs, two STAT3 KO hESC lines expressed OCT4 and NANOG and immunostained positive for OCT4, NANOG, TRA-1-81, SSEA3, TRA-1-60, and SSEA4 (FIGS. 20D and 20E), demonstrating that STAT3 KO did not affect the pluripotency of hESCs. STAT3 KO hESC lines were induced to differentiate into hIOs using a conventional stepwise differentiation protocol to derive fetal-like Cont-hIOs from hPSCs (FIG. 20F).

WT and STAT3 KO hESC lines were efficiently differentiated into DE, hindgut, and hIOs with adequate lineage-characteristic morphologies (FIG. 20G). We assessed the expression of intestinal transcription factors, including SOX9, CDX2, and KLF5, and intestinal cell type-specific markers, including villin 1 for enterocytes (VIL), chromogranin A for enteroendocrine cells (CHGA), lysozyme for Paneth cells (LYZ), and mucin 2 for goblet cells (MUC2), showing that Cont-hIOs, regardless of whether they were derived from WT or STAT3 KO hESC lines, contained all intestinal epithelial cell types (FIG. 20H).

To investigate the role of STAT3 in the in vitro maturation of hPSC-derived hIOs, we examined whether hIOs derived from these edited hESC lines could acquire intestinal maturation characteristics by assessing their morphologies and expression of intestinal maturation markers. Two passages after the induction of in vitro maturation by IL-2 treatment or co-culture with PMA/ionophore-stimulated Jurkat T lymphocytes, phenotypes of maturation were observed in WT hESC-derived hIOs (WT hIOs), which demonstrated an increased hIO size and an average number of buds per hIO (FIGS. 21A and 21B). The increase of the surface area of the hIOs indicated that the cell proliferation of the hIOs was enhanced, and the increase of the budding number showed that the number of intestinal stem cells and the differentiation capacity into intestinal epithelial cell types were enhanced.

Concomitantly, the WT Mat-hIO epithelium exhibited positive staining for well-known intestinal maturation-related proteins, such as DEFA5 and OLFM4, and functional brush-border enzymes, such as DPP4 and LCT. However, marked phenotypic differences were observed in the epithelium of STAT3 KO hESC-derived hIOs (STAT3 KO hIOs) even after in vitro maturation, which was also reflected in the reduced hIO size and the average number of buds per hIO (FIG. 21c).

We also examined the expression of DEFA5, OLFM4, DPP4, and LCT, which did not appear in the epithelium of STAT3 KO Mat-hIOs, even though the markers of all the intestinal epithelial cell types were found in the epithelium of STAT3 KO Mat-h Os. These results were further confirmed by qPCR analysis of intestinal maturation markers (FIG. 21D). After in vitro maturation by IL-2 treatment, STAT3 KO Mat-hIOs showed significantly lower expression levels of OLFM4, KRT20, MUC13, CREB3L3, CDX2, SI, DPP4, and LCT, similar to Cont-hIOs, compared to WT Mat-hIOs. To discriminate impaired in vitro maturation of hIOs from cell death, we performed co-staining with apoptotic cell death marker, cleaved caspase-3, and intestinal epithelial cell markers, OLFM1 or LYZ, respectively. The expression levels of OLFM4 and LYZ were significantly decreased in STAT3 KO hIOs and STAT3 inhibitor-treated hIOs compared to WT Mat-hIOs. However, the expression level of cleaved caspase-3 was not altered in STAT3 KO hIOs or STAT3 inhibitor-treated hIOs.

These results suggest that STAT3 KO severely impairs the in vitro maturation of the hIO epithelium, regardless of cell survival.

Based on the above description, it will be understood by those skilled in the art that the present invention may be implemented in a different specific form without changing the technical spirit or essential characteristics thereof. Therefore, it should be understood that the above embodiment is not limitative, but illustrative in all aspects. The scope of the invention is defined by the appended claims rather than by the description preceding them, and therefore all changes and modifications that fall within metes and bounds of the claims, or equivalents of such metes and bounds are therefore intended to be embraced by the claims.

Effect of the Invention

In vitro-matured intestinal organoids according to a preparation method of the present invention may solve the problem of requiring in vivo environment for the maturation of immature intestinal organoids, and the matured intestinal organoids of the present invention may be usefully applied to artificial organs, drug screening, cell therapy, etc.

What is claimed is:

1. A method of preparing an in vitro-matured human intestinal organoid, the method comprising
preparing an immature intestinal organoid by differentiating stem cells in a first medium, and
culturing the immature intestinal organoid in a second medium containing T-lymphocytes, Interleukin 2 (IL-2), or a combination thereof, wherein the first medium and the second medium are different.

2. The method of claim 1, wherein the stem cells comprise embryonic stem cells or induced pluripotent stem cells (iPSCs).

3. The method of claim 1, wherein the matured intestinal organoid has increased expression of one or more markers of the following (a) to (f), as compared with an immature intestinal organoid:
(a) intestinal maturation-related intestinal stem cell markers, CDX2 and OLFM4 (Olfactomedin-4);
(b) digestive function-related markers, DPP4 (Dipeptidyl peptidase-4) and LCT (lactase);
(c) immune function and host defense function-related markers, DEFA5 (human-defensins 5), DEFA6 (human-defensins 56), and LYZ (lysozyme);
(d) transporter system-related markers, SLC5A1 (solute carrier family 5 member 1), P-glycoprotein 1 (p-gp, multidrug resistance protein 1 (MDR1), and ATP-binding cassette sub-family B member 1 (ABCB1));
(e) mature intestinal differentiation markers, KRT20 (Keratin 20), MUC13 (Mucin 13), and CREB3L3 (Cyclic AMP-responsive element-binding protein 3); and
(f) STAT3 and mTOR signaling markers, phosphorylated STAT3 (signal transducer and activator of transcription 3), phosphorylated AKT (protein kinase B (PKB)), and phosphorylated P70S6 kinase (Ribosomal protein S6 kinase beta-1 (S6K1)).

4. The method according to claim 3, wherein the mature intestinal organoids have increased expression of DEFA5, OLFM4, MUC13 and KRT20.

5. The method of claim 1, wherein the T-lymphocytes are stimulated with phorbol myristate acetate and calcium ionophore.

6. A method of preparing an artificial intestine, the method comprising preparing intestinal organoids matured according to the method of claim 1.

7. A method of maturing a human intestinal organoid in vitro, the method comprising
    culturing an immature intestinal organoid obtained by differentiating stem cells in a medium containing Interleukin 2 (IL-2),
    wherein the intestinal organoid is not co-cultured with immune cells.

8. The method of claim 7, wherein the stem cells comprise embryonic stem cells or induced pluripotent stem cells (iPSCs).

9. The method of claim 7, wherein the matured intestinal organoid has increased expression of one or more markers of the following (a) to (f), as compared with an immature intestinal organoid:
    (a) intestinal maturation-related intestinal stem cell markers, CDX2 and OLFM4 (Olfactomedin-4);
    (b) digestive function-related markers, DPP4 (Dipeptidyl peptidase-4) and LCT (lactase);
    (c) immune function and host defense function-related markers, DEFA5 (human-defensins 5), DEFA6 (human-defensins 56), and LYZ (lysozyme);
    (d) transporter system-related markers, SLC5A1 (solute carrier family 5 member 1), P-glycoprotein 1 (p-gp, multidrug resistance protein 1 (MDR1), and ATP-binding cassette sub-family B member 1 (ABCB1));
    (e) mature intestinal differentiation markers, KRT20 (Keratin 20), MUC13 (Mucin 13), and CREB3L3 (Cyclic AMP-responsive element-binding protein 3); and
    (f) STAT3 and mTOR signaling markers, phosphorylated STAT3 (signal transducer and activator of transcription 3), phosphorylated AKT (protein kinase B (PKB)), and phosphorylated P70S6 kinase (Ribosomal protein S6 kinase beta-1 (S6K1)).

10. A method of producing a functional human intestinal organoid, comprising
    culturing an immature intestinal organoid obtained by differentiating stem cells, in a medium containing T-lymphocytes, Interleukin-2, or a combination thereof,
    wherein the resulting functional intestinal organoid comprises mature functional goblet cells and/or mature functional enteroendocrine cells.

11. The method according to claim 10, wherein the method excludes treating the immature intestinal organoid with Interleukin 22 (IL-22).

12. The method of claim 10, wherein the stem cells comprise embryonic stem cells or induced pluripotent stem cells (iPSCs).

13. The method of claim 10, wherein the matured intestinal organoid has increased expression of one or more markers of the following (a) to (f), as compared with immature intestinal organoid:
    (a) intestinal maturation-related intestinal stem cell markers, CDX2 and OLFM4 (Olfactomedin-4);
    (b) digestive function-related markers, DPP4 (Dipeptidyl peptidase-4) and LCT (lactase);
    (c) immune function and host defense function-related markers, DEFA5 (human-defensins 5), DEFA6 (human-defensins 56), and LYZ (lysozyme);
    (d) transporter system-related markers, SLC5A1 (solute carrier family 5 member 1), P-glycoprotein 1 (p-gp, multidrug resistance protein 1 (MDR1), and ATP-binding cassette sub-family B member 1 (ABCB1));
    (e) mature intestinal differentiation markers, KRT20 (Keratin 20), MUC13 (Mucin 13), and CREB3L3 (Cyclic AMP-responsive element-binding protein 3); and
    (f) STAT3 and mTOR signaling markers, phosphorylated STAT3 (signal transducer and activator of transcription 3), phosphorylated AKT (protein kinase B (PKB)), and phosphorylated P70S6 kinase (Ribosomal protein S6 kinase beta-1 (S6K1)).

14. The method of claim 10, wherein the T-lymphocytes are stimulated with phorbol myristate acetate and calcium ionophore.

* * * * *